US012746197B2

(12) United States Patent
Wagner et al.

(10) Patent No.: US 12,746,197 B2
(45) **Date of Patent: *Sep. 29, 2026**

(54) LONG ACTING INJECTABLE FORMULATION COMPRISING RISPERIDONE AND BIODEGRADABLE POLYMERS

(71) Applicant: MedinCell S.A., Jacou (FR)

(72) Inventors: Avia Merenlender Wagner, Binyamina (IL); Anna Elgart Valitsky, Kfar-Saba (IL); Eran Harary, Netanya (IL)

(73) Assignee: MEDINCELL S.A., Jacou (FR)

(*) Notice: Subject to any disclaimer, the term of this patent is extended or adjusted under 35 U.S.C. 154(b) by 2 days.

This patent is subject to a terminal disclaimer.

(21) Appl. No.: 18/281,392

(22) PCT Filed: Mar. 17, 2022

(86) PCT No.: PCT/EP2022/057009

§ 371 (c)(1),
(2) Date: Sep. 11, 2023

(87) PCT Pub. No.: WO2022/195018

PCT Pub. Date: Sep. 22, 2022

(65) Prior Publication Data

US 2024/0148641 A1 May 9, 2024

Related U.S. Application Data

(60) Provisional application No. 63/270,174, filed on Oct. 21, 2021, provisional application No. 63/208,860, filed on Jun. 9, 2021, provisional application No. 63/162,272, filed on Mar. 17, 2021.

(30) Foreign Application Priority Data

Mar. 17, 2021 (WO) .................. PCT/IB2021/052248

(51) Int. Cl.

| | |
|---|---|
| ***A61K 9/00*** | (2006.01) |
| ***A61K 31/519*** | (2006.01) |
| ***A61K 47/10*** | (2017.01) |
| ***A61K 47/34*** | (2017.01) |
| ***A61P 25/18*** | (2006.01) |

(52) U.S. Cl.

CPC .......... *A61K 9/0019* (2013.01); *A61K 31/519* (2013.01); *A61K 47/10* (2013.01); *A61K 47/34* (2013.01); *A61P 25/18* (2018.01)

(58) Field of Classification Search

None

See application file for complete search history.

(56) References Cited

U.S. PATENT DOCUMENTS 9,023,897 B2 5/2015 Gaudriault
2013/0331402 A1* 12/2013 Lewyn-Briscoe ... A61K 31/519 514/259.41
2019/0015415 A1* 1/2019 Konsoula ................ A61P 25/18
2019/0099495 A1 4/2019 Gaudriault
2019/0160171 A1 5/2019 Gaudriault
2020/0085728 A1* 3/2020 Gutierro Aduriz .. A61K 31/519
2021/0038724 A1 2/2021 Gaudriault
2024/0156722 A1* 5/2024 Rech ...................... A61K 47/20

FOREIGN PATENT DOCUMENTS

WO WO-2020154315 A1 * 7/2020 ........... A61K 31/519
WO WO-2021/048817 A1 3/2021

OTHER PUBLICATIONS

Eedekens et al. (Schizophrenia Research 70 91-100) (Year: 2004).*
Cetin et al. "Safety and efficacy of long-acting risperidone in schizophrenia: A 12-week, open-label study in stable patients switched from typical and atypical oral antipsychotics". European Neuropsychopharmacology, vol. 15, Supplement 2, pp. S134-S135 (Year: 2005).*
U.S. Office Action for U.S. Appl. No. 18/585,349, dated Aug. 14, 2024.
Andreasen et al., "Remission in Schizophrenia: Proposed Criteria and Rationale for Consensus," American Journal of Psychiatry, vol. 162, No. 3, 2005, pp. 441-449.
Cilurzo et al., "Injectability Evaluation: An Open Issue," AAPS PharmSciTech, vol. 12, No. 2, 2011, pp. 604-609.
Eerdekens et al., "Pharmacokinetics and tolerability of long-acting risperidone in schizophrenia," Schizophrenia Research, vol. 70, 2004, pp. 91-100.
Prescribing information for Perseris®, revised Dec. 2022, 43 pages total.
Prescribing information for Risperdal Consta®, revised Feb. 2021, 18 pages total.
Prescribing information for Rykindo®, revised Jan. 2023, 51 pages total.
Rainer, "Risperidone long-acting injection; a review of its long term safety and efficacy," Neuropsychiatric Disease and Treatment, vol. 4, No. 5, 2008, pp. 919-927.
"Teva and MedinCell Announce Positive Results for Registration Trial of Investigational Extended-Release Subcutaneous Injectable Risperidone for Patients With Schizophrenia", Jan. 7, 2021, 6 pages; retrieved from the internet on Dec. 3, 2021, https://www.businesswire.com/news/home/20210107005469/en/Teva-and-MedinCell-Announce-Positive-Results-for-Registration-Trial-of-Investigational-Extended-Release-Subcutaneous-Injectable-Risperidone-for-Patients-with-Schizophrenia.

(Continued)

*Primary Examiner* — Susan T Tran
(74) *Attorney, Agent, or Firm* — Birch, Stewart, Kolasch & Birch, LLP

(57) ABSTRACT

The present invention is directed to methods of treating psychiatric diseases and disorders comprising administering to a subject in need thereof at a frequency of no more than once every 28 days an injectable formulation comprising risperidone, triblock and diblock copolymers wherein the concentration of the risperidone is 250-400 mg/mL and injection volume is 1 mL or less.

14 Claims, 4 Drawing Sheets

(56) References Cited

OTHER PUBLICATIONS

Bepo—MedinCell, Mar. 2, 2021, Retrieved from the Internet: URL:https://web.archive.org/web/2021030213 3553/https://www.medincell.com/bepo/ [retrieved from the internet on Dec. 3, 2021.

Ivaturi et al., "Exposure-response analysis after subcutaneous administration of RBP-7000, a once-a-month long-acting Atrigel formulation of risperidone: E-R analysis of RBP-7000, a long acting risperidone formulation", British Journal of Clinical Pharmacology., vol. 83, No. 7, Jul. 1, 2017, pp. 1476-1498.

"Prescribing Information Perseris (risperidone for extended-release injectable suspension for subcutaneaous use)", Dec. 1, 2019, pp. 1-37, Retrieved from the Internet: URL:https://www.perseris.com/Downloads/USPI, Dec. 3, 2021.

Search Report and Written Opinion in International Application No. PCT/EP2022/057009 dated Jun. 22, 2022, 20 pages.

Search Report and Written Opinion in International Application No. PCT/IB2021/052248 dated Dec. 14, 2021, 18 pages.

* cited by examiner

LONG ACTING INJECTABLE FORMULATION COMPRISING RISPERIDONE AND BIODEGRADABLE POLYMERS

RELATED APPLICATIONS

This application claims the benefit of U.S. Provisional Application Nos. 63/162,272, filed Mar. 17, 2021, 63/208,860, filed Jun. 9, 2021, and 63/270,174 filed Oct. 21, 2021, and International Application No. PCT/IB2021/052248 filed Mar. 17, 2021, the entireties of which are incorporated by reference herein.

FIELD OF THE INVENTION

The present invention relates to methods of treating psychiatric diseases and disorders responsive to risperidone with high-concentration, low-volume risperidone pharmaceutical compositions comprising a triblock copolymer and a diblock copolymer.

BACKGROUND OF THE PRESENT INVENTION

Schizophrenia is a debilitating psychotic disorder, with a complex etiology. It is characterized by positive symptoms (eg, delusions, hallucinations, and grossly disorganized or catatonic behavior) and negative symptoms (eg, affective flattening, alogia, and avolition). Cognitive deficits including impairment of executive functioning and attention, difficulties with short- and long-term memory are common.

Risperidone is an atypical antipsychotic, a serotoninergic (5-HT2A receptor) and dopaminergic (D2, D3 and D4 receptor) antagonist. The substance also binds to alpha-1-adrenergic receptors, histaminergic H1 receptors and, to a lesser extent, alpha-2-adrenergic receptors. It does not have affinity for cholinergic receptors. Risperidone has been approved by the FDA since 1994 for the treatment of schizophrenia in adults and adolescents aged 13 to 17, and has been marketed under the name Risperdal®. Currently available in oral and injectable versions, risperidone is approved for a number of other indications, including treatment for dementia, anxiety, bipolar disorders, autism spectrum disorder (ASD), and manic or psychotic episodes.

Risperidone is used in first-line treatment of schizophrenia due to its safety profile and recommendation for medium and long-term treatment. Premature discontinuation of antipsychotic drug therapy is a common phenomenon. Even among patients who do not explicitly discontinue drug therapy, non-adherence to long-term oral medication regimen is one of the most significant therapeutic issues in the therapy of schizophrenia and related disorders. As a result, many of these patients do not experience the full benefit of antipsychotic drug therapy and suffer frequent relapses or exacerbations that require rehospitalization, often in the context of psychiatric emergency (Rainer M K, 2008. Risperidone long-acting injection: a review of its long term safety and efficacy. Neuropsychiatr Dis Treat 4(5):919-27). Thus, the use of a long-acting injectable (LAI) antipsychotic agent may improve prognosis and increase acceptance by Health Care Professionals (HCP) and acceptance and compliance in patients with schizophrenia.

LAI antipsychotic products have been approved by the FDA. Risperdal Consta®, is an injectable risperidone product for biweekly intramuscular (IM) administration. Risperdal Consta® is a microparticle formulation provided at doses 12.5 mg, 25 mg, 37.5 mg, and 50 mg risperidone/vial with a syringe having 2 mL of diluent. The product requires multiple reconstitution steps and oral supplementation at the start of treatment. Intramuscular injections are typically painful and anxiety inducing, in particular to the target population.

Perseris®, an injectable risperidone product for monthly subcutaneous administration, is provided in two syringes, one with PLGA polymer (liquid syringe) and a second with risperidone (powder syringe), which requires significant mixing and resuspension prior to administration. Perseris® is provided in two dose strengths, 90 mg (0.6 mL) and 120 mg (0.8 mL), comparable to 3 mg/day and 4 mg/day, respectively.

U.S. Pat. No. 9,023,897 and US patent publication US2019/160171 describe pharmaceutical formulations with biodegradable triblock and diblock copolymers, which are useful for the delivery of a variety of actives.

A challenge in treating psychiatric diseases or disorders using risperidone include, for example, the ability to subcutaneously inject a long-acting formulation having a high dose of active agent in a low injection volume, with an injectable viscosity. Another challenge is the development of a long-acting, subcutaneous injectable formulation having no or low initial burst of active agent.

There is a need for long-acting risperidone formulations that have the potential to improve patient prognosis, improve patient quality of life, enhance patient and HCP acceptance and patient compliance, lessen patient anxiety at administration, delay relapses, and that offer flexibility for patients and HCP in selecting dose strengths, dosing regimens, and ease of administration. Additionally, a formulation that improves the chances of a patient with schizophrenia to maintain stability and improve post-stabilization would be of considerable benefit to the patient and health care systems. The compositions and methods disclosed herein meet those needs and others.

SUMMARY OF THE INVENTION

Provided herein are compositions and methods for treating a psychiatric disease or disorder in a subject, comprising subcutaneously administering to the subject a risperidone formulation for once a month or once every two months administration that improves patient outcomes and exhibits one or more of the following features:

- Achieves therapeutic levels within 24 hours, thereby obviating the need for oral or parenteral supplementation, or a loading or booster dose;
- extends the time to relapse;
- decreases the rate of relapse;
- decreases total Positive and Negative Syndrome Scale (PANSS) score over time;
- increases a patient's chance to maintain stability and to improve post stabilization;
- ready to use (RTU) flowable formulation in a prefilled syringe with a short (5/8 inch, 16 mm), low gauge (21G) needle;
- allows direct dosing to once monthly (Q1M) or once every two months (Q2M) from oral risperidone;
- flexibility for patient and HCP to adjust doses as needed (ie, switching between doses, ie, 50 mg to 75 mg or 75 mg to 100 mg etc);
- flexibility for patient and HCP to switch between dosing regimens, as needed (ie, switching between Q1M to Q2M or between Q2M and Q1M);

flexibility for patient and HCP to switch a patient from an orally administered antipsychotic, ie risperidone, to the risperidone formulation (Q1M or Q2M) disclosed herein the day after the last dose of the oral therapy;

flexibility for patient and HCP to switch a patient from a parenterally administered antipsychotic to the risperidone formulation (Q1M or Q2M) disclosed herein at the next dosing;

flexibility to select administration site (abdomen or upper arm) independently at each dosing for optimal compliance and comfort.

Furthermore, the presentation of the once every two months (Q2M) doses is intended to specifically address the unmet medical need for improved convenience and compliance, one of the biggest obstacles to success with pharmacotherapy in the treatment of schizophrenia. The treatment further increased the proportion of patients maintaining stability, for example maintaining stability up to 6 months, maintaining stability up to 9 months, maintaining stability up to 12 months, maintaining stability up to 15 months and longer. Unexpectedly, patients continue improving post stabilization, as assessed by PANSS (ie, reduction in score), for example for up to 6 months post stabilization, up to 9 months post stabilization, up to 12 months post stabilization, up to 15 months post stabilization and longer.

The methods disclosed herein obviate the need for supplemental or loading doses of risperidone therapy (e.g., oral or parenteral) to reach therapeutic doses. An aspect of the invention provides a method of switching a subject from a daily oral risperidone therapy to a long acting injectable risperidone formulation, said method comprising:

i. orally administering a final administration of the daily oral risperidone therapy, after which no further oral risperidone therapy is administered; and ii. the next day subcutaneously administering to the subject a long acting injectable risperidone formulation comprising (a) risperidone, or a pharmaceutically acceptable salt thereof, at a concentration of about 250-400 mg/mL, equivalent to risperidone;

(b) a biodegradable triblock copolymer having the formula:

poly(lactic acid)$_v$-poly(ethylene glycol)$_w$-poly(lactic acid)$_x$, wherein v and x are the number of repeat units ranging from 24 to 682 and w is the number of repeat units ranging from 4 to 273 and v=x or v #x;

(c) a biodegradable diblock copolymer having the formula:

methoxy-poly(ethylene glycol)$_y$-poly(lactic acid)$_z$, wherein y and z are the number of repeat units, wherein y is the number of repeat units ranging from 3 to 50 and z is the number of units ranging from 7 to 327; and wherein the ratio of the biodegradable triblock copolymer of (b) and the biodegradable diblock copolymer of (c) is 1:3 to 1:8 or 1:1 to 1:19 or 3:2 to 1:19, in said formulation, which is insoluble in an aqueous environment;

thereby switching the subject from a daily oral risperidone therapy to a long acting injectable risperidone formulation.

A further aspect of the invention provides a method of switching a subject from a long acting injectable antipsychotic to a long acting injectable risperidone formulation without the need for supplemental oral risperidone therapy, the method comprising:

i. administering a final dose the long acting injectable antipsychotic; and ii. at the next dosing, subcutaneously administering the long acting injectable risperidone formulation;

wherein the long acting injectable risperidone formulation comprises:

a. risperidone, or a pharmaceutically acceptable salt thereof, at a concentration of about 250-400 mg/mL, equivalent to risperidone;

b. a biodegradable triblock copolymer having the formula: poly(lactic acid)$_v$-poly(ethylene glycol)$_w$-poly (lactic acid)$_x$, wherein v and x are the number of repeat units ranging from 24 to 682 and w is the number of repeat units ranging from 4 to 273 and v=x or v≠x;

c. a biodegradable diblock copolymer having the formula: methoxy-poly(ethylene glycol)$_y$-poly(lactic acid)$_z$, wherein y and z are the number of repeat units, wherein y is the number of repeat units ranging from 3 to 50 and z is the number of units ranging from 7 to 327; and wherein the ratio of the biodegradable triblock copolymer of (b) and the biodegradable diblock copolymer of (c) is 1:3 to 1:8 or 1:1 to 1:19 or 3:2 to 1:19, in said formulation, which is insoluble in an aqueous environment; and wherein said method is performed without administering to the subject a supplemental oral risperidone therapy.

In further aspects, a subject can switch between doses of long acting injectable risperidone formulation once monthly and once every 2 months by administering the first dose of the new dosing regimen on the next scheduled date of administration in the original dosing regimen. The dose administration schedule may be revised to reflect the change. Accordingly, the present invention provides a method of switching a subject from a once monthly long acting injectable risperidone formulation to a once bimonthly (i.e., once every two months) long acting injectable risperidone formulation without the need for supplemental oral risperidone therapy, said method comprising:

i. subcutaneously administering a final dose of the once monthly long acting injectable risperidone formulation; and ii. one month later subcutaneously administering the once bimonthly (i.e., once every two months) long acting injectable risperidone formulation;

wherein each of the once monthly and once bimonthly (i.e., once every two months) long acting injectable risperidone formulations comprise (a) risperidone, or a pharmaceutically acceptable salt thereof, at a concentration of about 250-400 mg/mL, equivalent to risperidone;

(b) a biodegradable triblock copolymer having the formula: poly(lactic acid) poly(ethylene glycol)$_w$-poly(lactic acid)$_x$, wherein v and x are the number of repeat units ranging from 24 to 682 and w is the number of repeat units ranging from 4 to 273 and v=x or v≠x;

(c) a biodegradable diblock copolymer having the formula: methoxy-poly(ethylene glycol)$_y$-poly(lactic acid)$_z$, wherein y and z are the number of repeat units, wherein y is the number of repeat units ranging from 3 to 50 and z is the number of units ranging from 7 to 327; and wherein the ratio of the biodegradable triblock copolymer of (b) and the biodegradable diblock copolymer of (c)

is 1:3 to 1:8 or 1:1 to 1:19 or 3:2 to 1:19, in said formulation, which is insoluble in an aqueous environment; and wherein said method is performed without administering to the subject a supplemental oral risperidone therapy.

In a further aspect, the invention provides a method of switching a subject from a once bimonthly (i.e., once every two months) long acting injectable risperidone formulation to a once monthly long acting injectable risperidone formulation without the need for supplemental oral risperidone therapy, said method comprising:

i. subcutaneously administering a final dose of the once bimonthly (i.e., once every two months) long acting injectable risperidone formulation; and ii. two months later subcutaneously administering the once monthly long acting injectable risperidone formulation;

wherein the once monthly and once bimonthly (i.e., once every two months) long acting injectable risperidone formulations comprise (a) risperidone, or a pharmaceutically acceptable salt thereof, at a concentration of about 250-400 mg/mL, equivalent to risperidone;

(b) a biodegradable triblock copolymer having the formula: poly(lactic acid) poly(ethylene glycol)$_w$-poly(lactic acid)$_x$, wherein v and x are the number of repeat units ranging from 24 to 682 and w is the number of repeat units ranging from 4 to 273 and v=x or v≠x;

(c) a biodegradable diblock copolymer having the formula: methoxy poly(ethylene glycol)$_y$-poly(lactic acid)$_z$, wherein y and z are the number of repeat units, wherein y is the number of repeat units ranging from 3 to 50 and z is the number of units ranging from 7 to 327; and wherein the ratio of the biodegradable triblock copolymer of (b) and the biodegradable diblock copolymer of (c) is 1:3 to 1:8 or 1:1 to 1:19 or 3:2 to 1:19, in said formulation, which is insoluble in an aqueous environment; and wherein said method is performed without administering to the subject a supplemental oral risperidone therapy.

In another aspect the invention provides a method of treating a psychiatric disease or disorder in a subject, comprising subcutaneously administering to the subject a long acting injectable risperidone-polymer formulation wherein the administration is once every two months, wherein administration results in a mean exposure of the TAM (AUC0-tau) that is equivalent to that of oral risperidone (2 mg/day to 5 mg/day) administered over an equivalent dosing period.

In another aspect the invention provides a method of treating a psychiatric disease or disorder in a subject, comprising subcutaneously administering to the subject a long acting injectable risperidone-polymer formulation wherein the risperidone formulation comprises risperidone and a polymer and the administration is selected from the subject's upper arm and/or abdomen.

An additional aspect of the invention provides a method of switching a risperidone dose in a subject administered once monthly or once bimonthly (i.e., once every two months) long acting injectable risperidone formulation from an initial dose of a long acting injectable risperidone formulation to a subsequent dose of a long acting injectable risperidone formulation, without the need for supplemental oral risperidone therapy, said method comprising:

i. subcutaneously administering a final administration of the initial dose of the long acting injectable risperidone formulation; and ii. at the next dosing subcutaneously administering the subsequent dose of the long acting injectable risperidone formulation;

wherein the initial dose and the subsequent dose of the long acting injectable risperidone formulations are different doses of a long acting injectable risperidone formulation that comprises (a) risperidone, or a pharmaceutically acceptable salt thereof, at a concentration of about 250-400 mg/mL, equivalent to risperidone;

(b) a biodegradable triblock copolymer having the formula:

poly(lactic acid)$_v$-poly(ethylene glycol)$_w$-poly(lactic acid)$_x$, wherein v and x are the number of repeat units ranging from 24 to 682 and w is the number of repeat units ranging from 4 to 273 and v=x or v≠x;

(c) a biodegradable diblock copolymer having the formula:

methoxy-poly(ethylene glycol)$_y$-poly(lactic acid)$_z$, wherein y and z are the number of repeat units, wherein y is the number of repeat units ranging from 3 to 50 and z is the number of units ranging from 7 to 327; and wherein the ratio of the biodegradable triblock copolymer of (b) and the biodegradable diblock copolymer of (c) is 1:3 to 1:8 or 1:1 to 1:19 or 3:2 to 1:19, in said formulation, which is insoluble in an aqueous environment; and wherein said method is performed without administering to the patient any supplemental oral risperidone therapy.

A still further aspect is a method of administering risperidone to a subject undergoing long acting injectable risperidone therapy wherein said subject has missed a dose of a long acting injectable risperidone formulation, said method comprising subcutaneously administering a dose of a once monthly or once bimonthly (i.e., once every two months) long acting injectable risperidone formulation;

wherein the long acting injectable risperidone formulation comprises (a) risperidone, or a pharmaceutically acceptable salt thereof, at a concentration of about 250-400 mg/mL, equivalent to risperidone;

(b) a biodegradable triblock copolymer having the formula: poly(lactic acid)$_v$-poly(ethylene glycol)$_w$-poly(lactic acid)$_x$, wherein v and x are the number of repeat units ranging from 24 to 682 and w is the number of repeat units ranging from 4 to 273 and v=x or v≠x;

(c) a biodegradable diblock copolymer having the formula: methoxy-poly(ethylene glycol)$_y$-poly(lactic acid)$_z$, wherein y and z are the number of repeat units, wherein y is the number of repeat units ranging from 3 to 50 and z is the number of units ranging from 7 to 327; and wherein the ratio of the biodegradable triblock copolymer of (b) and the biodegradable diblock copolymer of (c) is 1:3 to 1:8 or 1:1 to 1:19 or 3:2 to 1:19, in said formulation, which is insoluble in an aqueous environment; and wherein said method is performed without administering to the subject any supplemental oral risperidone therapy.

An additional aspect of the invention provides a prefilled syringe (PFS) for subcutaneously administering a long acting injectable risperidone formulation, said prefilled syringe comprising the long acting injectable risperidone formulation wherein said formulation comprises (a) risperidone, or a pharmaceutically acceptable salt thereof, at a concentration of about 250-400 mg/mL, equivalent to risperidone;

(b) a biodegradable triblock copolymer having the formula: poly(lactic acid)$_v$-poly(ethylene glycol)$_w$-poly(lactic acid)$_x$, wherein v and x are the number of repeat units ranging from 24 to 682 and w is the number of repeat units ranging from 4 to 273 and v=x or v≠x;

(c) a biodegradable diblock copolymer having the formula: methoxy-poly(ethylene glycol)$_y$-poly(lactic acid)$_z$, wherein y and z are the number of repeat units, wherein y is the number of repeat units ranging from 3 to 50 and z is the number of units ranging from 7 to 327; and wherein the ratio of the biodegradable triblock copolymer of (b) and the biodegradable diblock copolymer of (c) is 1:3 to 1:8 or 1:1 to 1:19 or 3:2 to 1:19, in said formulation, which is insoluble in an aqueous environment; and a needle having a gauge number equal to or greater than 21 and/or a length equal to or shorter than ⅝ inch.

A further aspect of the invention provides a kit comprising the prefilled syringe as defined above;

a needle having a gauge number equal to or greater than 21 and/or a length equal to or shorter than ⅝ inch; and optionally instructions for use.

A further aspect of the invention provides a method of treating a psychiatric disease or disorder in a subject, comprising subcutaneously administering to the subject a long acting injectable risperidone-polymer formulation wherein the administration is once every two months, wherein administration results in a mean exposure of the TAM (AUC0-tau) that is equivalent to that of oral risperidone (2 mg/day to 5 mg/day) administered over an equivalent dosing period.

A further aspect of the invention provides a method of treating a psychiatric disease or disorder in a subject, comprising subcutaneously administering to the subject a long acting injectable risperidone-polymer formulation wherein the risperidone formulation comprises risperidone and a polymer and the administration is selected from the subject's upper arm and/or abdomen.

In some aspects, the disclosure is directed to methods of treating a psychiatric disease or disorder in a subject, comprising subcutaneously administering to the subject at a frequency of no more than once every 28 days 1 mL or less of a long acting injectable risperidone formulation comprising:

a) risperidone, or a pharmaceutically acceptable salt thereof, at a concentration of about 250-400 mg/mL, equivalent to risperidone;

b) a biodegradable triblock copolymer having the formula:

poly(lactic acid)$_v$-poly(ethylene glycol)$_w$-poly(lactic acid)$_x$ wherein v and x are the number of repeat units ranging from 24 to 682 and w is the number of repeat units ranging from 4 to 273 and v=x or v≠x;

c) a biodegradable diblock copolymer having the formula: methoxy-poly(ethylene glycol)$_y$-poly(lactic acid)$_z$, wherein y and z are the number of repeat units, wherein y is the number of repeat units ranging from 3 to 50 and z is the number of repeat units ranging from 7 to 327;

wherein the ratio of the biodegradable triblock copolymer of (b) and the biodegradable diblock copolymer of (c) is 1:3 to 1:8 or 1:1 to 1:19 or 3:2 to 1:19, in said formulation, which is insoluble in an aqueous environment;

wherein the risperidone formulation provides a therapeutically effective amount of risperidone for at least 28 days.

In some embodiments, the formulation is subcutaneously administered to the subject once monthly (Q1M) wherein the formulation provides a therapeutically effective amount of risperidone for at least one month. In some embodiments, the formulation is subcutaneously administered to the subject once every two months (Q2M) wherein the formulation provides a therapeutically effective amount of risperidone for at least two months.

In some embodiments, the formulation is subcutaneously administered to the subject at an intermediate duration between Q1M and Q2M, for example once every six weeks (Q6W) wherein the formulation provides a therapeutically effective amount of risperidone for about six weeks.

In particular, the active principle of the injectable formulations disclosed herein is risperidone present in a concentration of 250 mg/mL or greater, for example, about 250 mg/mL to 400 mg/mL, or about 300 mg/mL to about 400 mg/mL or a pharmaceutically acceptable salt thereof in an amount equivalent to 250 mg/mL to 400 mg/mL risperidone. In some embodiments, risperidone is present in a concentration of 360 mg/mL or is a pharmaceutically acceptable salt thereof in an amount equivalent to about 360 mg/mL risperidone. With the injectable formulations of the invention, the active principle has a release duration of 21-90 days (about 3 weeks to about 3 months) or 30-90 days (about 1 month to about 3 months). In some aspect, the release duration is about 28-31 days (about 4 weeks to about 1 month). In some aspect, the release duration is about 56-62 days (about 8 weeks to about 2 months to about 9 weeks). In some aspects, the release duration is about 84-94 days (about 12 weeks to about 13 weeks or about 12 weeks to about 3 months).

In some embodiments, administration of the long acting injectable risperidone formulation provides a total active moiety (TAM) plasma level comparable to a 2-5 mg (2 mg, 3 mg, 4 mg, or 5 mg) daily oral administration.

In some embodiments the long acting injectable risperidone formulation is administered to a subject at a frequency of no more than once every 28 days. In some embodiments in which the long acting injectable risperidone formulation is administered once monthly, the formulation comprises from about 50 mg to about 125 mg risperidone, e.g., 50, 75, 100, or 125 mg of risperidone. In some embodiments, the once monthly dose comprises 50 mg of risperidone. In some embodiments, the once monthly dose comprises 75 mg of risperidone. In some embodiments, the once monthly dose comprises 100 mg of risperidone. In some embodiments, the once monthly dose comprises 125 mg of risperidone. In some embodiments, the volume of the risperidone formulation for a Q1M dose up to 125 mg is 0.5 mL or less, specifically from about 0.1 mL to about 0.5 mL or from about 0.14 mL to about 0.35 mL. In some embodiments, the volume of the risperidone formulation for a 50 mg dose is about 0.1 mL, for a 75 mg dose is about 0.2 mL, for a 100 mg dose is about 0.3 mL and for a 125 mg dose is about 0.4 mL. In some embodiments, the volume of the risperidone formulation for a 50 mg dose is about 0.14 mL, for a 75 mg dose is about 0.21 mL, for a 100 mg dose is about 0.28 mL and for a 125 mg dose is about 0.35 mL.

In some embodiments in which the long acting injectable risperidone formulation is administered once every two months, the formulation comprises from about 100 mg to about 250 mg risperidone, e.g., 100, 150, 200, or 250 mg risperidone. In some embodiments, the once every two months dose comprises 100 mg of risperidone. In some embodiments, the once every two months dose comprises 150 mg of risperidone. In some embodiments, the once every two months dose comprises 200 mg of risperidone. In some embodiments, the once every two months dose comprises 250 mg of risperidone. In some embodiments, the volume of the risperidone formulation for a Q2M dose up to 250 mg is 1.0 mL or less, specifically from about 0.2 mL to about 1.0 mL, or from about 0.2 mL up to about 0.7 mL. In some embodiments, the volume of the risperidone formulation for a 100 mg dose is about 0.3 mL, for a 150 mg dose is about 0.4 mL, for a 200 mg dose is about 0.6 mL and for a 250 mg dose is 0.7 mL. In some embodiments, the volume of the risperidone formulation for a 100 mg dose is about 0.28 mL, for a 150 mg dose is about 0.42 mL, for a 200 mg dose is about 0.56 mL and for a 250 mg dose is 0.70 mL.

In some embodiments in which the long acting injectable risperidone formulation is administered once every six weeks (Q6W), wherein each dose comprises from about 75 mg to about 200 mg risperidone.

Other aspects and embodiments are set forth below, or will readily arise from the following description of the preferred embodiments.

DETAILED DESCRIPTION OF THE INVENTION

Definitions

Figure 1:
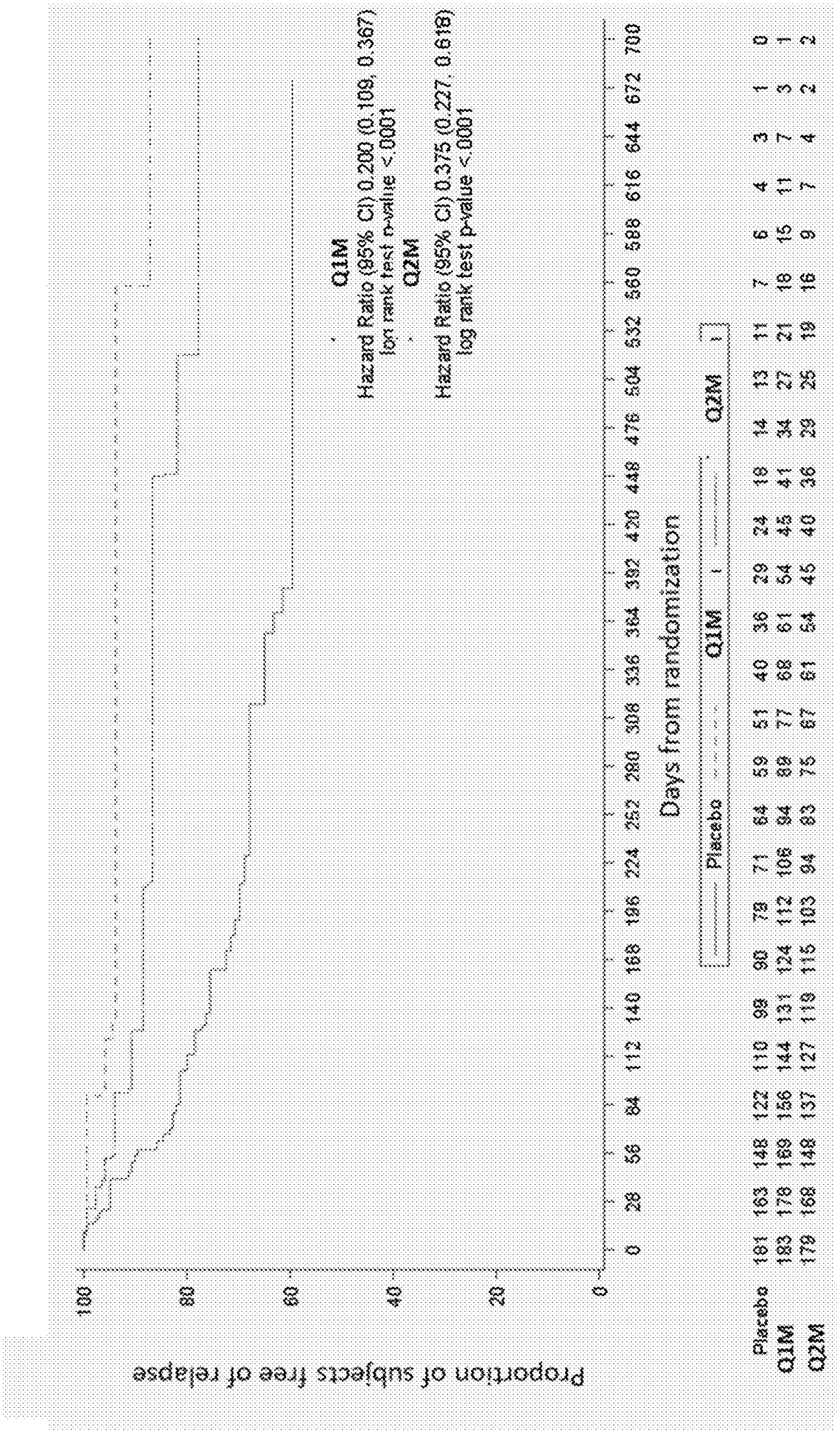
FIG. 1: Primary Efficacy Endpoint, time to impending relapse (ITT analysis set) results shown as Kaplan-Meier Survival Curve. Risperidone formulation decreased the risk to relapse by 80.0% and 62.5% for Q1M (short dashed line) and Q2M (long dashed line) respectively, compared to placebo (solid line) for the entire study duration.

As used herein the term "biodegradable" means that the triblock and diblock copolymers will after a period of time erode or degrade in vivo to form smaller non-toxic components.

The term "parenteral administration" encompasses intramuscular, intraperitoneal, intra-abdominal, subcutaneous, intravenous and intraarterial. It also encompasses intradermal, intracavernous, intravitreal, intracerebral, intrathecal, epidural and intraosseous administration. In some embodiments, the formulations disclosed herein are administered subcutaneously. In specific embodiments, the risperidone formulation disclosed herein is administered by a healthcare professional as an abdominal or upper arm subcutaneous injection.

The term "about" should be considered as disclosing the range defined by the absolute values of the two endpoints. For example, the expression "from about 300 to about 400" also discloses the values 300 and 400. When used to modify a single number, the term "about" may refer to plus or minus 10% of the indicated value and includes the indicated number. For example, "about 15%" may indicate a range of 13.5% to 16.5%, and "about 1" means from 0.9 to 1.1.

The term "subject" encompasses all members of the Kingdom Animalia, with a human being preferred.

The active principle, ie, active pharmaceutical ingredient, API, according to the invention is risperidone and pharmaceutically acceptable salts thereof.

As used herein, "psychiatric disease or disorder" refers to a mental illness, regardless of etiology. Certain psychiatric diseases and disorders known to be responsive to risperidone include, for example, schizophrenia, schizoaffective disorder, schizophreniform disorder, bipolar disorder for example bipolar 1 disorder, and irritability associated with autism (IAA), for example in adults or in children on the autism spectrum.

As used herein "risperidone formulation", "long acting injectable risperidone formulation(s)", "extended release injectable suspension", "pharmaceutical composition(s)", "pharmaceutical formulation(s)", "biodegradable drug formulation(s)" and "biodegradable drug delivery composition(s)" refer to a risperidone formulation described herein that provides a therapeutic concentration of risperidone in plasma to a patient in need thereof over a period of one month or two months, and may be used interchangeably. A "long acting injectable risperidone therapy" refers to the treatment of a subject with the risperidone formulation disclosed herein.

A "long acting injectable antipsychotic" as used herein refers to a long acting injectable product comprising an antipsychotic drug substance which is approved (by a regulatory agency, eg, FDA and/or EMA) for parenteral administration (e.g. intramuscular, subcutaneous). Non-limiting examples include PERSERIS®, Risperdal® Consta®, Abilify Maintena®.

As used herein, "administered at a frequency of no more than once every 28 days" means administration of the long acting injectable risperidone formulation once every 28 days or more, and up to once every two months.

As used herein, the terms "once monthly" or "q1m" or "Q1M" or "once every month" mean one time per month and they may be used interchangeably. In some embodiments, "once monthly", or "q1m" or "Q1M" or "once every month" mean once every 4 weeks (Q4W), once every 28-31 days, such as, for example, once every 28 days, once every 29 days, once every 30 days, or once every 31 days. A "once monthly", "q1m", "Q1M" or "once every month" administration may be made on any day of the month, such as, for example, the 1st day, 2nd day, 3rd day, and so on. A subsequent administration of a "once monthly", "q1 m", "Q1M" or "once every month" formulation is then made one month, for example 28 days or 28-31 days, later.

As used herein, the terms "once bimonthly" or "q2m" or "Q2M" or "once every two months" mean one time every two months and they may be used interchangeably. In some embodiments, "once bimonthly" or "q2m" or "Q2M" or "once every two months" mean once every 8 weeks (Q8W), or once every 56-62 days, such as, for example, once every 56 days, once every 57 days, once every 58 days, once every 59 days, once every 60 days, once every 61 days, or once every 62 days. A "once bimonthly" or "q2m" or "Q2M" or "once every two months" administration may be made on any day of the month, such as, for example, the 1st day, 2nd day, 3rd day, and so on. A subsequent administration of a once "once bimonthly" or "q2m" or "Q2M" or "once every two months" formulation is then made two months, for example 56 days or 56-62 days later.

A "once every six weeks" or "Q6W" administration may be used interchangeably and mean once every 42 days, or about once every 42 days such as, for example, once every 41 days, once every 42 days, or once every 43 days. A "once every six weeks" or "Q6W" administration be made on any day of the month, such as, for example, the 1st day, 2nd day, 3rd day, and so on. A subsequent administration of a "once every six weeks" or "06W" formulation is then made six weeks later, for example 42 days or about 42 days later.

In one aspect of the methods disclosed herein, the dosing regimen may be retained (eg. Q1M followed by Q1M) or may switched from administration to administration (eg. Q1M to Q2M or Q2M to Q1M).

The term "implant" means that the drug delivery compositions are injectable, are in situ forming, are biodegradable and turn into solid (or semi solid) implants in situ. Thus, the formulations that are disclosed herein are flowable liquids that can be easily injected through a syringe, as recited herein (i.e. subcutaneously), without excessive force.

As used herein "repeat units" are the fundamental recurring units of a polymer. For example, lactic acid (LA) is the repeat unit in poly(lactic acid) and ethylene oxide (EO) is the repeat unit in poly(ethylene glycol).

By "end-capped polyethylene glycol" (cPEG) refers to PEG's in which one terminal hydroxyl group is reacted and includes alkoxy-capped PEG's, urethane-capped PEG's ester-capped PEG's and like compounds. The capping group is a chemical group which does not contain a chemical function susceptible to react with cyclic esters like lactide, glycolide, caprolactone and the like or other esters and mixtures thereof. The reaction of an end-capped PEG polymer with lactide generates a diblock cPEG-PLA copolymer. As an example, mPEG-PLA refers to a methoxy capped PEG-polylactide diblock copolymer.

The abbreviation "PEG" refers to poly(ethylene glycol), poly(ethylene oxide) or poly(oxy ethylene) and the terms are used interchangeably herein. A PEG polymer includes repeats of ethylene glycol, also known as ethylene oxide (EO).

The abbreviation of "PLA" refers to polylactide, polylactic acid or poly(lactic acid) and the terms are used interchangeably herein. A PLA polymer includes repeats of lactic acid (LA).

The abbreviation "T" or "TB" refers to a triblock copolymer(s), while the abbreviation "D" or "DB" refers to a diblock copolymer(s).

The term "diblock" as used herein refers, for example, to an end-capped PEG-polyester copolymer, preferably to an end-capped PEG-poly(lactic acid) copolymer. "mPEG" refers to methoxy-polyethylene glycol. The PEG in the diblock copolymer may be capped with known capping entities other than a methoxy group. Examples of end-capped polyethylene glycols include alkoxy capped PEG's such as methoxyPEG or ethoxyPEG, urethane-capped PEG's, ester-capped PEG's, amine-capped PEG's and amide-capped PEG's.

This list of end-capped PEG's is not exhaustive and a person skilled in the art would recognize additional end-capped PEG's, which are not listed.

The term "triblock" refers, for example, to a polyester-PEG-polyester copolymer, preferably poly(lactic acid)-PEG-poly(lactic acid) copolymer.

In some embodiments of the risperidone formulation, the diblock copolymer comprises a methoxy capped PEG and poly(D,L-lactic acid) and may be referred to as "mPEG-PDL" or "mPEG-PDLLA" and the triblock copolymer comprises poly(D,L-lactic acid)-PEG-poly(D,L-lactic acid) and may be referred to as "PDL-PEG-PDL" or "PDLLA-PEG-PDLLA".

The biodegradable drug delivery compositions used in the methods of the present disclosure are described in U.S. Pat. No. 9,023,897, the entirety of which is incorporated by reference herein.

The structure of the biodegradable triblock/diblock copolymers of the invention may also be represented as follows:

$A_v$-$B_w$-$A_x$, which refers to the triblock copolymer poly (lactic acid)$_v$-poly(ethylene oxide)$_w$-poly(lactic acid)$_x$, is also identified herein as PaRb, where "a" is the PEG size in kDa and "b" is the molar ratio LA/EO (v+x/w).

$C_y$-$A_z$, which refers to the diblock mPEG-PLA copolymer: methoxy-poly(ethylene glycol)$_y$-poly(lactic acid)$_z$, is also identified herein as dPaRb, where "a" is the PEG size in kDa and "b" is the molar ratio LA/EO (z/y). The methoxy group, or other capping group, will cap one of the two hydroxyl groups of the PEG. The poly(lactic acid) chain will extend only from the free hydroxyl group.

The letters v, w, x, y and z represent the repeat unit number. The number of repeat units (degree of polymerization (DP)) of y and z in the diblock composition may vary. Thus, y can, for example, range from 3 to 50, 7 to 43 or 3 to 45 and z can range from 32 to 123 or 7 to 327. For example, y can be 25 and z can be 123, y can be 34.5 and z can be 123 or y can be 45 and z can be 32. The degree of polymerization for PEG (DP-PEG) is calculated by dividing the PEG molecular weight of the capped PEG by the EO unit molecular weight (44 Da). The degree of polymerization for PLA (DP-PLA) is calculated by multiplying DP-PEG by the LA/EO ratio.

The LA/EO ratio refers to the molar ratio of lactic acid units to ethylene oxide units that is present in each of the block copolymers present in the biodegradable drug delivery composition. It is determined experimentally by NMR. The LA/EO molar ratio of the triblock copolymer can range from 0.5 to 8. The LA/EO molar ratio of the triblock copolymer can range from 0.5 to 3.5. In another aspect the LA/EO molar ratio in the triblock can range from 0.5 to 2.5 in the pharmaceutical formulations described herein. In yet another aspect the LA/EO ratio in the triblock can range from 0.5 to 22.3.

The LA/EO ratio in the diblock can range from 2 to 6. In another aspect the LA/EO ratio in the diblock can range from 3 to 5 in the pharmaceutical formulations described herein. In another aspect the LA/EO ratio in the diblock can range from 0.8 to 13.

The degree of polymerization or DP is the number of repeat units in an average polymer chain at time tin a polymerization reaction. For example, the degree of polymerization for PEG is about 45 to 170 or it can be 4 to 273 or 3 to 50, while for PLA it can range from about 84 to 327 or it can be 24 to 682 or 7 to 327.

The methods disclosed herein use a biodegradable drug composition comprising a triblock copolymer and a diblock copolymer. The biodegradable triblock copolymer has the formula: $A_v$-$B_w$-$A_x$, wherein A is a poly(lactic acid) and B is poly(ethylene glycol) and v and x are the number of repeat units of the poly(lactic acid) and range from 24 to 682; and w is the degree of polymerization (number of repeat units) for the poly(ethylene glycol) and ranges from 4 to 273, and v=x or v≠x. The degree of polymerization for DP-PEG is calculated by dividing the PEG molecular weight by the EO unit molecular weight (44 Da). v+x equals the degree of polymerization (number of repeat units) for PLA. DP-PLA is calculated by multiplying DP-PEG by the LA/EO ratio.

The size of the PEG in the triblock copolymer can range from 194 Da to 12,000 Da. The triblock copolymer may be combined with a biodegradable diblock copolymer having the formula: $C_y$-$A_z$, wherein A is a polyester (i.e., PLA) and C is an end-capped polyethylene glycol and y and z are the number of repeat units ranging from 7 to 371 or from 3 to 327. This combination has a ratio of triblock copolymer to diblock copolymer ranging from 1:3 to 1:8 or 1:1 to 1:19 or 3:2 to 1:19. In some aspects, the ratio of triblock copolymer to diblock copolymer is 3:2 to 1:5. In some aspects, the ratio of triblock copolymer to diblock copolymer is 3:2 to 1:4.5. In some aspects, the ratio of triblock copolymer to diblock copolymer is 3:2 to 1:4. In some aspects, the ratio of triblock copolymer to diblock copolymer is 3:2 to 1:3.5. In some aspects, the ratio of triblock copolymer to diblock copolymer is 3:2 to 1:3. In some aspects, the ratio of triblock copolymer to diblock copolymer is 3:2 to 1:2.5. In some aspects, the ratio of triblock copolymer to diblock copolymer is 3:2 to 1:2. In some aspects, the ratio of triblock copolymer to diblock copolymer is or 3:2 to 1:1.5. In some aspects, the ratio of triblock copolymer to diblock copolymer is 3:2 to 1:1. In some embodiments, the ratio of triblock copolymer to diblock copolymer is 3:2, 3:1, 2:1, 1:1, 1:1.5, 1:2, 1:2.5, 1:3, 1:3.5, 1:4, 1:4.5 or 1:5. In some embodiments, the ratio of triblock copolymer to diblock copolymer is about 1: 1.5.

In various embodiments of the methods, compositions and kits disclosed herein, the triblock copolymers having the formula $A_v$-$B_w$-$A_x$ wherein each of v and x is independently the number of repeat units ranging from about 24 to 682, or about 25 to 420, or about 25 to 400, or about 30 to 200, 35 to 120, or about 40 to 100 and w is the number of repeat units ranging from 4 to 273, or about 4 to 115, or about 20 to 75; and the diblock copolymers having the formula $C_y$-$A_z$ wherein y is 3 to 50, or about 8 to 50 and z is 7 to 327, or about 25 to 300, or about 50 to 200. Accordingly, in specific embodiments of the methods, compositions and kits disclosed herein, the triblock copolymers having the formula $A_v$-$B_w$-$A_x$ wherein each of v and x is independently the number of repeat units ranging from about 40 to 100 and w is the number of repeat units ranging from about 20 to 75; and the diblock copolymers having the formula $C_y$-$A_z$ wherein y is about 8 to 50 and z is about 50 to 200.

In some embodiments, the psychiatric disease or disorder is schizophrenia, schizoaffective disorder, irritability associated with autism, or bipolar disorder. In other embodiments, the psychiatric disease or disorder is schizophrenia or bipolar disorder. In other embodiments, the psychiatric disease or disorder is schizophrenia. In other embodiments, the psychiatric disease or disorder is schizoaffective disorder. In yet other embodiments, the psychiatric disease or disorder is bipolar disorder, for example bipolar 1 disorder. In some embodiments, the psychiatric disease or disorder is irritability in children or adolescents and/or adults on the autism spectrum also known as irritability associated with autism (IAA).

In some aspects, the psychiatric disease is dementia. In some aspects, the psychiatric disease is bipolar disorder. In some aspects, the psychiatric disease is depression. In some aspects, the psychiatric disease is a manic disorder. In some aspects, the psychiatric disease is a psychotic episode.

"Method of treating" as used herein refers to alleviating symptoms of the psychiatric disease or disorder. In certain preferred embodiments, the psychiatric disease or disorder is schizophrenia. In some embodiments, method of treating includes a delay in time to relapse compared to a subject not receiving the pharmaceutical formulation e.g., as compared to the subject receiving a placebo. In some embodiments, method of treatment includes a reduced impending relapse rate as estimated using the Kaplan-Meier method. In some embodiments, method of treatment includes a reduced Observed Rate of Impending Relapse. In some embodiments, method of treatment includes improving post stabilization, as assessed by PANSS. In some embodiments, method of treatment includes decreased risk of relapse. In some embodiments, method of treatment includes maintaining stability. In some embodiments, method of treatment includes improving quality of life, for example as measured by the SQLS scores.

In some embodiments, the method of treating schizophrenia includes maintaining stability including meeting all of the following criteria for at least 4 consecutive weeks: outpatient status; PANSS total score ≤80; minimal presence of specific psychotic symptoms on the PANSS, as measured by a score of ≤4 on each of the following items: conceptual disorganization, suspiciousness, hallucinatory behavior, and unusual thought content; Clinical Global Impression of Severity (CGI-S) score (moderately ill); and Clinical Global Impression-Severity of Suicidality (CGI-SS) score (mildly suicidal) on Part 1 and (minimally worsened) on Part 2. The percentage will be calculated as the number of patients who maintained stability at endpoint divided by the number of patients in the given treatment group. In some embodiments, method of treatment includes Achieving Remission. All remission criteria can be derived from PANSS items.

In some aspects, the disclosed methods result in a reduction in the risk to relapse compared to placebo in subjects having schizophrenia. In some embodiments, the risk to relapse is reduced by at least 50% compared to placebo in subjects having schizophrenia.

In some embodiments in which the long acting injectable risperidone formulation is administered once monthly, the risk to relapse is reduced by 60-80% compared to placebo in subjects having schizophrenia. In some embodiments in which the long acting injectable risperidone formulation is administered once monthly, the risk to relapse is reduced by 80% compared to placebo in subjects having schizophrenia.

In some embodiments in which the long acting injectable risperidone formulation is administered once every two months, the risk to relapse is reduced by 50-65% compared to placebo in subjects having schizophrenia. In some embodiments in which the long acting injectable risperidone formulation is administered once every two months, the risk to relapse is reduced by 62.5% compared to placebo in subjects having schizophrenia.

In other aspects, the disclosed methods result in a lower rate of relapse compared to placebo in subjects having schizophrenia.

In yet other aspects, the disclosed methods extend the time to relapse compared to placebo in subjects having schizophrenia. In some embodiments, the time to relapse is extended by at least 2-fold compared to placebo in subjects having schizophrenia.

In some embodiments in which the long acting injectable risperidone formulation is administered once monthly, the time to relapse is extended by at least 2.5 to 5-fold compared to placebo in subjects having schizophrenia. In some embodiments in which the long acting injectable risperidone formulation is administered once monthly, the time to relapse is extended by 5-fold compared to placebo in subjects having schizophrenia.

In some embodiments in which the long acting injectable risperidone formulation is administered once every two months, the time to relapse is extended by at least 2.5 to 5-fold compared to placebo in subjects having schizophrenia. In some embodiments in which the long acting injectable risperidone formulation is administered once every two months, the time to relapse is extended by 2.7-fold compared to placebo in subjects having schizophrenia.

In some aspects, the present disclosure is directed to methods of treating a psychiatric disease or disorder in a subject by subcutaneous administration of a long acting injectable risperidone formulation. In particularly preferred embodiments, the subject is a human. In some embodiments, the subject is a human adult, aged 18 years or older or aged 18 years to 65 years. In some embodiment, the subject is a human adolescent, aged 13 years to 17 years.

The methods disclosed herein comprise subcutaneous administration of a high concentration, low volume formulation of risperidone to a subject in need thereof, for example a subject afflicted with a psychiatric disease or disorder. In some embodiments, the subcutaneous administration is into the upper arm of the subject or the abdomen of the subject. In some embodiments, the subcutaneous administration is to the abdomen of the subject. In other embodiments, the subcutaneous administration is to the upper arm of the subject, particularly to the back of the upper arm. The administration site (abdomen or upper arm) may be switched, i.e., interchanged from administration to administration without affecting the efficacy or safety of any method of the disclosure. Thus, in some embodiments of the disclosed methods, a subcutaneous administration of the long acting injectable risperidone formulation to the upper arm is followed by, at the next dosing, a subcutaneous administration of the long acting injectable risperidone formulation to the abdomen. In some aspects a subcutaneous administration of the long acting injectable risperidone formulation to the abdomen is followed by, at the next dosing, a subcutaneous administration of the long acting injectable risperidone formulation to the upper arm. As used here, the phrase "at the next dosing" refers to the next dosing event at which the long acting injectable risperidone formulation is administered.

Subcutaneous administration of the risperidone formulation of the invention typically results in the in situ formation of a solid or semi-solid implant. In these embodiments, the solid or semi-solid formulation is excisable (i.e., can be removed from the subject) following administration into the subject. A healthcare professional (HCP) with skill in the art will be able to determine whether to excise and the preferred manner and time to excise.

In some aspects of the methods of the invention, the administration is with a frequency of no more than once every 21 days. In these aspects, the administration results in treating of the psychiatric disease or disorder for at least 21 days. In some embodiments, the administration is with a frequency of no more than once every 28 days. In these aspects, the administration results in treating of the psychiatric disease or disorder for at least 28 days. In some embodiments, the administration is with a frequency of no more than once every 30 days. In these aspects, the administration results in treating of the psychiatric disease or disorder for at least 30 days. In other embodiments, the administration is with a frequency of no more than once every 42 days. In these aspects, the administration results in treating of the psychiatric disease or disorder for at least 42 days. In other embodiments, the administration is with a frequency of no more than once every 56 days. In these aspects, the administration results in treating of the psychiatric disease or disorder for at least 56 days. In other embodiments, the administration is with a frequency of no more than once every 60 days. In these aspects, the administration results in treating of the psychiatric disease or disorder for at least 60 days.

According to the methods of the invention, the subject is administered 1 mL or less of a pharmaceutical formulation, as described herein. In some embodiments, the subject is administered 1 mL of the pharmaceutical formulation. In other embodiments, the subject is administered 0.9 mL or less of the pharmaceutical formulation. In other embodiments, the subject is administered 0.8 mL or less of the pharmaceutical formulation. In other embodiments, the subject is administered 0.7 mL or less of the pharmaceutical formulation. In other embodiments, the subject is administered 0.6 mL or less of the pharmaceutical formulation. In other embodiments, the subject is administered 0.5 mL or less of the pharmaceutical formulation. In other embodiments, the subject is administered 0.4 mL or less of the pharmaceutical formulation. In other embodiments, the subject is administered 0.3 mL or less of the pharmaceutical formulation. In other embodiments, the subject is administered 0.2 mL or less of the pharmaceutical formulation. In other embodiments, the subject is administered 0.1 mL or less of the pharmaceutical formulation. In some embodiments, the subject is administered 0.1, 0.2, 0.3, 0.4, 0.5, 0.6, 0.7, 0.8, 0.9, or 1 mL of the pharmaceutical formulation. In some embodiments, the subject is administered 0.1, 0.11, 0.12, 0.13, 0.14, 0.15, 0.16, 0.17, 0.18, 0.19, 0.2, 0.21, 0.22, 0.23, 0.24, 0.25, 0.26, 0.27, 0.28, 0.29, 0.3, 0.31, 0.32, 0.33, 0.34, 0.35, 0.36, 0.37, 0.38, 0.39, 0.4, 0.41, 0.42, 0.43, 0.44, 0.45, 0.46, 0.47, 0.48, 0.49, 0.5, 0.51, 0.52, 0.53, 0.54, 0.55, 0.56, 0.57, 0.58, 0.59, 0.6, 0.61, 0.62, 0.63, 0.64, 0.65, 0.66, 0.67, 0.68, 0.69, 0.7, 0.71, 0.72, 0.73, 0.74, 0.75, 0.76, 0.77, 0.78, 0.79, 0.8, 0.81, 0.82, 0.83, 0.84, 0.85, 0.86, 0.87, 0.88, 0.89, 0.9, 0.91, 0.92, 0.93, 0.94, 0.95, 0.96, 0.97, 0.98, 0.99, or 1 mL of the pharmaceutical formulation. In some embodiments, the pharmaceutical formulation comprises 250 mg/mL to 400 mg/mL of risperidone or a salt thereof, equivalent to 250 mg/mL to 400 mg/mL risperidone. In some embodiments, the pharmaceutical formulation comprises 300 mg/mL to 400 mg/mL or 300 mg/mL, 310 mg/mL, 320 mg/mL, 330 mg/mL 340 mg/mL, 350 mg/mL, 360 mg/mL, 370 mg/mL, 380 mg/mL, 390 mg/mL or 400 mg/mL of risperidone or a salt thereof, equivalent to 300 mg/mL, 310 mg/mL, 320 mg/mL, 330 mg/mL 340 mg/mL, 350 mg/mL, 360 mg/mL, 370 mg/mL, 380 mg/mL, 390 mg/mL or 400 mg/mL risperidone.

In some aspects, the disclosure is directed to methods of administering a therapeutically effective dose of risperidone to a subject for a time period of at least 28 days and up to two months comprising subcutaneously administering to the subject, 1 mL or less of a long acting injectable risperidone formulation comprising (a) risperidone, or a pharmaceutically acceptable salt thereof, at a concentration of about 250-400 mg/mL, equivalent to risperidone;

(b) a biodegradable triblock copolymer having the formula: poly(lactic acid)$_v$-poly(ethylene glycol)$_w$-poly(lactic acid)$_x$, wherein v and x are the number of repeat units ranging from 24 to 682 and w is the number of repeat units ranging from 4 to 273 and v=x or v≠x;

(c) a biodegradable diblock copolymer having the formula: methoxy-poly(ethylene glycol)$_y$-poly(lactic acid)$_z$, wherein y and z are the number of repeat units, wherein y is the number of repeat units ranging from 3 to 50 and z is the number of units ranging from 7 to 327; and wherein the ratio of the biodegradable triblock copolymer of (b) and the biodegradable diblock copolymer of (c) is 1:3 to 1:8 or 1:1 to 1:19 or 3:2 to 1:19, in said formulation, which is insoluble in an aqueous environment;

wherein the frequency of the administration is at least once in 28 days and up to two months; and wherein the administration results in the systemic administration of the risperidone for the time period.

In some embodiments of such methods, the frequency of the administration is no greater than once every 28 days, or is once monthly or once every two months. In some embodiments of such methods, the time period is one month. In other embodiments, the time period is two months.

In some embodiments, provided herein is a method of treating a risperidone naïve patient with the long acting injectable risperidone formulation disclosed herein, the method comprising a) establishing patient tolerability with oral daily risperidone;

b) administering subcutaneously to the patient a once monthly or a once every two month long acting injectable risperidone formulation the day after the last dose of oral therapy;

c) wherein the long acting injectable risperidone formulation comprises:

i) risperidone, or a pharmaceutically acceptable salt thereof, at a concentration of about 250-400 mg/mL, equivalent to risperidone;

ii) a biodegradable triblock copolymer having the formula: poly(lactic acid)$_v$-poly(ethylene glycol)$_w$-poly(lactic acid)$_x$ wherein v and x are the number of repeat units ranging from 24 to 682 and w is the number of repeat units ranging from 4 to 273 and v=x or v≠x;

iii) a biodegradable diblock copolymer having the formula: methoxy-poly(ethylene glycol)$_y$-poly(lactic acid)$_z$, wherein y and z are the number of repeat units, wherein y is the number of repeat units ranging from 3 to 50 and z is the number of repeat units ranging from 7 to 327;

wherein the ratio of the biodegradable triblock copolymer of (b) and the biodegradable diblock copolymer of (c) is 1:3 to 1:8 or 1:1 to 1:19 or 3:2 to 1:19, in said formulation, which is insoluble in an aqueous environment;

thereby treating a risperidone naïve patient.

A risperidone naïve patient is a patient who has not previously been administered risperidone.

In some aspects, the disclosure is directed to methods of switching a subject from a daily oral risperidone therapy to a long acting injectable risperidone formulation for example, switching from oral daily risperidone to either a once monthly injection or a once every two month injection the day after the last dose of oral therapy. In some embodiments, such methods comprise:

i. orally administering a final administration of the daily oral risperidone therapy, after which no further oral risperidone therapy is administered; and ii. the next day subcutaneously administering to the subject a long acting injectable risperidone formulation comprising (a) risperidone, or a pharmaceutically acceptable salt thereof, at a concentration of about 250-400 mg/mL, equivalent to risperidone;

(b) a biodegradable triblock copolymer having the formula: poly(lactic acid)$_v$-poly(ethylene glycol)$_w$-poly(lactic acid)$_x$, wherein v and x are the number of repeat units ranging from 24 to 682 and w is the number of repeat units ranging from 4 to 273 and v=x or v≠x;

(c) a biodegradable diblock copolymer having the formula: methoxy-poly(ethylene glycol)$_y$-poly(lactic acid)$_z$, wherein y and z are the number of repeat units, wherein y is the number of repeat units ranging from 3 to 50 and z is the number of units ranging from 7 to 327; and wherein the ratio of the biodegradable triblock copolymer of (b) and the biodegradable diblock copolymer of (c) is 1:3 to 1:8 or 1:1 to 1:19 or 3:2 to 1:19, in said formulation, which is insoluble in an aqueous environment;

thereby switching the subject from a daily oral risperidone therapy to a long acting injectable risperidone formulation.

As used herein, the daily oral risperidone therapy refers to risperidone (e.g., a pharmaceutical composition comprising risperidone active ingredient) that is orally administered to the subject once per day. In some embodiments the daily oral risperidone therapy is 2 mg/day to 6 mg/day, or 2 mg/day to 5 mg/day, or 2 mg/day, 3 mg/day, 4 mg/day, 5 mg/day or 6 mg per day.

In some embodiments of the methods of switching a subject from a daily oral risperidone therapy to a long acting injectable risperidone formulation, the method comprises a once monthly administration of the long acting injectable risperidone formulation. In some embodiments, the long acting injectable risperidone formulation comprises from about 50 mg to about 125 mg risperidone.

In other embodiments of the methods of switching a subject from a daily oral risperidone therapy to a long acting injectable risperidone formulation, the method comprises a once every two months administration of the long acting injectable risperidone formulation. In some embodiments, the long acting injectable risperidone formulation comprises from about 100 mg to about 250 mg risperidone.

For example, the long acting injectable risperidone formulation may be initiated as follows: a patient treated with a 2 mg/day oral dose of risperidone may be switched to a 50 mg once monthly or a 100 mg once every two months dose of the LAI risperidone formulation disclosed herein, a patient treated with a 3 mg/day oral dose of risperidone may be switched to a 75 mg once monthly or a 150 mg once every two months dose of the LAI risperidone formulation disclosed herein, a patient treated with a 4 mg/day oral dose of risperidone may be switched to a 100 mg once monthly or a 200 mg once every two months dose of the LAI risperidone formulation disclosed herein and a patient treated with a 5 mg/day oral dose of risperidone may be switched to a 125 mg once monthly or a 250 mg once every two months dose of the LAI risperidone formulation disclosed herein.

In some aspects, the disclosure is directed to methods of switching a subject from a parenteral, i.e. intramuscular or subcutaneous long acting injectable antipsychotic product to the long acting injectable risperidone formulation disclosed herein. Advantageously, such switches may be accomplished without the need for supplemental risperidone therapy, ie, oral or parenteral. For example, the methods of the disclosure allow for switching a subject to the long acting injectable risperidone formulation disclosed herein without the need for a loading dose of risperidone. In some embodiments, provided herein is a method for switching a patient from an intramuscular or subcutaneous long acting injectable antipsychotic to the long acting injectable risperidone formulation disclosed herein without the need for a loading dose of oral or parenteral risperidone.

In some aspects, the disclosure is directed to methods of switching a subject from a long acting injectable antipsychotic to a long acting injectable risperidone formulation without the need for supplemental risperidone therapy. In some embodiments, such methods comprise:

i. administering a final dose of the long acting injectable antipsychotic; and ii. at the next dosing subcutaneously administering the long acting injectable risperidone formulation;

wherein the long acting injectable risperidone formulation comprises a. risperidone, or a pharmaceutically acceptable salt thereof, at a concentration of about 250-400 mg/mL, equivalent to risperidone;

b. a biodegradable triblock copolymer having the formula: poly(lactic acid)$_v$, poly(ethylene glycol)$_w$-poly(lactic acid)$_x$, wherein v and x are the number of repeat units ranging from 24 to 682 and w is the number of repeat units ranging from 4 to 273 and v=x or v≠x;

c. a biodegradable diblock copolymer having the formula: methoxy-poly(ethylene glycol)$_y$-poly(lactic acid)$_z$, wherein y and z are the number of repeat units, wherein y is the number of repeat units ranging from 3 to 50 and z is the number of units ranging from 7 to 327; and wherein the ratio of the biodegradable triblock copolymer of (b) and the biodegradable diblock copolymer of (c) is 1:3 to 1:8 or 1:1 to 1:19 or 3:2 to 1:19, in said formulation, which is insoluble in an aqueous environment; and wherein said method is performed without administering to the subject a supplemental oral risperidone therapy.

As used in this context, the phrase "at the next dosing" refers to the dosing event at which the next dose of the long acting injectable antipsychotic would be administered if the long acting injectable antipsychotic were not being discontinued. In some embodiments the long acting injectable anti-psychotic is an intramuscular long acting injectable product (e.g. Risperdal® Consta®, Abilify Maintena®) In some embodiments, the long acting injectable antipsychotic is a subcutaneous long acting injectable product (e.g. PERSERIS®). In some embodiments, the long acting injectable antipsychotic comprises an approved antipsychotic, for example risperidone, 9-OH-risperidone (paliperidone) or aripiprazole. In some embodiments, wherein the long acting injectable anti-psychotic is not risperidone, a salt thereof or a metabolite thereof, the subject has been assessed for risperidone tolerance.

In some aspects, the disclosure is directed to methods of switching a subject from a once monthly long acting injectable risperidone formulation to a once bimonthly (i.e., once every two months) long acting injectable risperidone formulation without the need for supplemental oral or parenteral risperidone therapy. In some embodiments, such methods comprise:

i. subcutaneously administering a final dose of the once monthly long acting injectable risperidone formulation; and ii. one month (ie. 28-31 days) later subcutaneously administering the once every two months long acting injectable risperidone formulation;

wherein each of the once monthly and once every two months long acting injectable risperidone formulations comprise (a) risperidone, or a pharmaceutically acceptable salt thereof, at a concentration of about 250-400 mg/mL, equivalent to risperidone;

(b) a biodegradable triblock copolymer having the formula: poly(lactic acid)$_v$-poly(ethylene glycol)$_w$-poly(lactic acid)$_x$, wherein v and x are the number of repeat units ranging from 24 to 682 and w is the number of repeat units ranging from 4 to 273 and v=x or v≠x;

(c) a biodegradable diblock copolymer having the formula: methoxy-poly(ethylene glycol)$_y$-poly(lactic acid)$_z$, wherein y and z are the number of repeat units, wherein y is the number of repeat units ranging from 3 to 50 and z is the number of units ranging from 7 to 327; and wherein the ratio of the biodegradable triblock copolymer of (b) and the biodegradable diblock copolymer of (c) is 1:3 to 1:8 or 1:1 to 1:19 or 3:2 to 1:19, in said formulation, which is insoluble in an aqueous environment; and wherein said method is performed without administering to the subject a supplemental oral risperidone therapy.

In other aspects, the disclosure is directed to methods of switching a subject from a once bimonthly (i.e., once every two months) long acting injectable risperidone formulation to a once monthly long acting injectable risperidone formulation without the need for supplemental oral or parenteral risperidone therapy. In some embodiments, such methods comprise:

i. subcutaneously administering a final dose of the once bimonthly (i.e., once every two months) long acting injectable risperidone formulation and ii. two months later subcutaneously administering the once monthly long acting injectable risperidone formulation;

wherein each of the once monthly and once bimonthly (i.e., once every two months) long acting injectable risperidone formulations comprise (a) risperidone, or a pharmaceutically acceptable salt thereof, at a concentration of about 250-400 mg/mL, equivalent to risperidone;

(b) a biodegradable triblock copolymer having the formula: poly(lactic acid)$_v$-poly(ethylene glycol)$_w$-poly(lactic acid)$_x$, wherein v and x are the number of repeat units ranging from 24 to 682 and w is the number of repeat units ranging from 4 to 273 and v=x or v≠x;

(c) a biodegradable diblock copolymer having the formula: methoxy-poly(ethylene glycol)$_y$-poly(lactic acid)$_z$, wherein y and z are the number of repeat units, wherein y is the number of repeat units ranging from 3 to 50 and z is the number of units ranging from 7 to 327; and wherein the ratio of the biodegradable triblock copolymer of (b) and the biodegradable diblock copolymer of (c) is 1:3 to 1:8 or 1:1 to 1:19 or 3:2 to 1:19, in said formulation, which is insoluble in an aqueous environment; and wherein said method is performed without administering to the subject a supplemental oral risperidone therapy.

For the methods disclosed above, the administration schedule should be adjusted accordingly where needed.

In other aspects, the disclosure provides methods of changing the risperidone dose administered to a subject administered a once monthly or once bimonthly (i.e., once every two months) long acting injectable risperidone formulation from an initial dose to a subsequent dose, without the need for supplemental risperidone therapy, such as, for example, a loading dose of oral or parenteral risperidone.

In some embodiments, the disclosure provides methods of switching the risperidone dose administered to a subject from an initial dose to a subsequent dose, without the need for supplemental oral risperidone therapy, said method comprising:

i. subcutaneously administering a final administration of the initial dose of the long acting injectable risperidone formulation; and ii. at the next dosing subcutaneously administering the subsequent dose of the long acting injectable risperidone formulation;

wherein the initial and the subsequent doses of long acting injectable risperidone formulations are different doses of a risperidone formulation that comprises (a) risperidone, or a pharmaceutically acceptable salt thereof, at a concentration of about 250-400 mg/mL, equivalent to risperidone;

(b) a biodegradable triblock copolymer having the formula: poly(lactic acid)$_v$-poly(ethylene glycol)$_w$-poly(lactic acid)$_x$, wherein v and x are the number of repeat units ranging from 24 to 682 and w is the number of repeat units ranging from 4 to 273 and v=x or v≠x;

(c) a biodegradable diblock copolymer having the formula: methoxy-poly(ethylene glycol)$_y$-poly(lactic acid)$_z$, wherein y and z are the number of repeat units, wherein y is the number of repeat units ranging from 3 to 50 and z is the number of units ranging from 7 to 327; and wherein the ratio of the biodegradable triblock copolymer of (b) and the biodegradable diblock copolymer of (c) is 1:3 to 1:8 or 1:1 to 1:19 or 3:2 to 1:19, in said formulation, which is insoluble in an aqueous environment; and wherein said method is performed without administering to the patient any supplemental oral risperidone therapy.

In some embodiments, when utilizing the once monthly formulations, the initial dose of the long acting injectable risperidone formulation comprises a higher dose of risperidone than the subsequent dose of long acting injectable risperidone formulation. In some embodiments, the initial dose of the long acting injectable risperidone formulation comprises about 125 mg and the subsequent dose of the long acting injectable risperidone formulation comprises about 50 mg, 75 mg or about 100 mg risperidone. In some embodiments, the initial dose of the long acting injectable risperidone formulation comprises about 100 mg risperidone and the subsequent dose of the long acting injectable risperidone formulation comprises about 50 mg or 75 mg risperidone. In another example, when utilizing the once every two months formulations, the initial dose of the long acting injectable risperidone formulation comprises about 250 mg and the subsequent dose of the long acting injectable risperidone formulation comprises about 100 mg, 150 mg or about 200 mg risperidone. In some embodiments, the initial dose of the long acting injectable risperidone formulation comprises about 200 mg risperidone and the subsequent dose of the long acting injectable risperidone formulation comprises about 100 mg or 150 mg risperidone.

In other embodiments when utilizing the once monthly formulations, the initial dose of the long acting injectable risperidone formulation comprises a lower dose of risperidone than the subsequent dose of long acting injectable risperidone formulation. In some embodiments, the initial dose of the long acting injectable risperidone formulation comprises about 50 mg risperidone and the subsequent dose of the long acting injectable risperidone formulation comprises about 75 mg, 100 mg or 125 mg risperidone. In some embodiments, the initial dose of the long acting injectable risperidone formulation comprises about 75 mg risperidone and the subsequent dose of the long acting injectable risperidone formulation comprises about 100 mg or 125 mg risperidone. In another example when utilizing the once every two months formulations, the initial dose of the long acting injectable risperidone formulation comprises about 100 mg and the subsequent dose of the long acting injectable risperidone formulation comprises about 150 mg, 200 mg or about 250 mg risperidone. In some embodiments, the initial dose of the long acting injectable risperidone formulation comprises about 150 mg risperidone and the subsequent dose of the long acting injectable risperidone formulation comprises about 200 mg or 250 mg risperidone.

Depending on the dosing regimen of the initial dose, the subsequent dose of the long acting injectable risperidone formulation is administered one month (i.e., 28-31 days) after administration of the initial dose of the long acting injectable risperidone formulation. In other embodiments, the subsequent dose of the long acting injectable risperidone formulation is administered two months (i.e. 56-62 days) after administration of the initial dose of the long acting injectable risperidone formulation. Optionally, the dosing regimen might also be changed simultaneously (from a once bimonthly (i.e., once every two months) long acting injectable risperidone formulation to a once monthly long acting injectable risperidone formulation or vice versa).

In some aspects, the disclosure provides methods of administering risperidone to a subject undergoing long acting injectable risperidone therapy wherein said subject has missed a dose of the long acting injectable risperidone therapy.

As used herein, the term "missed a dose" means that the subject has not received a dose of long acting injectable risperidone formulation within the time period recommended for the particular long acting injectable risperidone therapy. For example, a subject who is receiving once monthly long acting injectable risperidone therapy, a missed dose would occur when more than one month elapses since the last administration of the once monthly long acting injectable risperidone formulation. For a subject who is on a once every two months regimen, i.e. receiving once every two months long acting injectable risperidone formulation, a missed dose would occur when more than two months elapses since the last administration of the once every two months long acting injectable risperidone formulation.

In some embodiments, such methods comprise subcutaneously administering a dose of a once monthly or once bimonthly (i.e., once every two months) long acting injectable risperidone formulation;

wherein the long acting injectable risperidone formulation comprises
- (a) risperidone, or a pharmaceutically acceptable salt thereof, at a concentration of about 250-400 mg/mL, equivalent to risperidone;
- (b) a biodegradable triblock copolymer having the formula: poly(lactic acid)$_v$-poly(ethylene glycol)$_w$-poly(lactic acid)$_x$, wherein v and x are the number of repeat units ranging from 24 to 682 and w is the number of repeat units ranging from 4 to 273 and v=x or v≠x;
- (c) a biodegradable diblock copolymer having the formula: methoxy-poly(ethylene glycol)$_y$-poly(lactic acid)$_z$, wherein y and z are the number of repeat units, wherein y is the number of repeat units ranging from 3 to 50 and z is the number of units ranging from 7 to 327; and wherein the ratio of the biodegradable triblock copolymer of (b) and the biodegradable diblock copolymer of (c) is 1:3 to 1:8 or 1:1 to 1:19 or 3:2 to 1:19, in said formulation, which is insoluble in an aqueous environment; and wherein said method is performed without administering to the subject any supplemental oral risperidone therapy.

In the methods of the disclosure, administration of the long acting injectable risperidone formulation can be restarted without administering to the subject any supplemental oral risperidone therapy, such as, for example, a loading dose of oral risperidone.

According to the methods of the invention, the administered pharmaceutical formulations comprise risperidone, or a pharmaceutically acceptable salt thereof. In some embodiments, the pharmaceutical formulation comprises risperidone as risperidone base. In other embodiments, the pharmaceutical formulation comprises risperidone as a pharmaceutically acceptable salt of risperidone. In yet other embodiments, the pharmaceutical formulation comprises risperidone as a mixture of risperidone base and a pharmaceutically acceptable salt of risperidone.

The pharmaceutically effective amount of risperidone may vary depending on the extent of the subject's medical condition and the time required to deliver the risperidone. The methods of the invention are particularly directed to formulations having the risperidone (or salt thereof) at a concentration of at least 250 mg/mL, equivalent to risperidone, in a 1 mL or less delivery volume. While there is no critical upper limit on the amount of risperidone (or salt thereof), the formulation should be of a viscosity suitable for injection through a syringe needle such that it can effectively treat the psychiatric disease or disorder without exposing the subject to a risperidone overdose risk. In some embodiments the methods comprise administration of the risperidone formulation from a prefilled syringe. In some embodiments, the prefilled syringe is a single dose prefilled syringe. The single dose prefilled syringe may contain from 25 mg to about 500 mg risperidone or the equivalent of a pharmaceutically acceptable salt, or from about 50 mg to about 250 mg risperidone or the equivalent of a pharmaceutically acceptable salt. In some embodiments, the needle that is used to administer the formulations of the invention is no less than 21 gauge. In some embodiments, the needle that is used to administer the formulations is from 21 to 23 gauge, or 21 gauge, or 23 gauge. In some embodiments, the needle that is used to administer the formulations of the invention is no greater than ⅝ inch in length. In some embodiments, the needle that is used to administer the formulations of the invention is between 12 mm and 20 mm long, or about 12.7 mm (½ inch) 13 mm, 14 mm, 15 mm, 16 mm (⅝ inch), 17 mm, 18 mm, 19 mm, or 20 mm. In some embodiments, the needle that is used to administer the formulations of the invention is 21 gauge and 16 mm (⅝ inch) long.

Thus, in some embodiments of the methods of the invention, the long acting injectable risperidone formulation is administered from a prefilled syringe fitted with a needle having a gauge number equal to or greater than 21 and/or a length equal to or shorter than ⅝ inch. In some embodiments, the long acting injectable risperidone formulation is administered from a prefilled syringe fitted with a needle having a gauge number equal to or greater than 21, such as, for example, 21 gauge, 22 gauge, 23 gauge, and the like. In other embodiments, the long acting injectable risperidone formulation is administered from a prefilled syringe fitted with a needle having a length equal to or shorter than ⅝ inch (i.e., 16 mm), such as, 16 mm, 15 mm, 14 mm, 13 mm, 12 mm, and the like. In some embodiments of the methods of the invention, the long acting injectable risperidone formulation is administered from a prefilled syringe fitted with a safety needle having a gauge number equal to or greater than 21 and a length equal to or shorter than ⅝ inch.

"Therapeutically effective amount of risperidone" is an amount of total active moiety (TAM), sum of risperidone and 9-OH-risperidone plasma concentrations, corrected by molecular weight, according to the following formula:

$$[\text{Active Moiety}](\text{ng/mL})=[\text{risperidone}](\text{ng/mL})+[\text{9-OH-risperidone}](\text{ng/mL})\ 410/426))$$

that is effective in mitigating at least some of the symptoms of the psychiatric disease or disorder in the affected subject. A therapeutically effective amount of risperidone may be, for example, a plasma level of >10 ng/mL within about 6 hours post administration (Eerdekens, et al., Pharmacokinetics and tolerability of long-acting risperidone in schizophrenia. Schizophr Res 70(1):91. 2004).

The concentration of risperidone, or a pharmaceutically acceptable salt thereof, used in the biodegradable drug delivery composition of the invention is at least 250 mg/mL equivalent to risperidone, preferably at least 300 mg/mL equivalent to risperidone. In some embodiments, the concentration of risperidone or a pharmaceutically acceptable salt thereof used in the biodegradable drug delivery composition of the invention is 250-300 mg/mL equivalent to risperidone. In other embodiments, the concentration of risperidone or a pharmaceutically acceptable salt thereof used in the biodegradable drug delivery composition of the invention is 300-400 mg/mL equivalent to risperidone. In other embodiments, the concentration of risperidone or a pharmaceutically acceptable salt thereof used in the biodegradable drug delivery composition of the invention is 300-350 mg/mL equivalent to risperidone. In other embodiments, the concentration of risperidone or a pharmaceutically acceptable salt thereof used in the biodegradable drug delivery composition of the invention is 350-400 mg/mL equivalent to risperidone Concentrations of risperidone, or the equivalent amount of a risperidone salt, in the formulations can range from about 250 mg/mL to 400 mg/mL, 260 mg/mL to 400 mg/mL, 270 mg/mL to 400 mg/mL, 280 mg/mL to 400 mg/mL, 290 mg/mL to 400 mg/mL, 300 mg/mL to 400 mg/mL, 310 mg/mL to 440 mg/mL, 315 mg/mL to 440 mg/mL, 320 mg/mL to 400 mg/mL, 330 mg/mL to 400 mg/mL, 340 mg/mL to 400 mg/mL, 350 mg/mL to 400 mg/mL, 360 mg/mL to 400 mg/mL, 370 mg/mL to 400 mg/mL, 380 mg/mL to 400 mg/mL, 390 mg/mL to 400 mg/mL, 260 mg/mL to 340 mg/mL, 270 mg/mL to 340 mg/mL, 280 mg/mL to 340 mg/mL. In some embodiments, the formulation comprises about 25% to about 35% risperidone or about 25%, 26%, 27%, 28%, 29%, 30%, 31%, 32%, 33%, 34% or 35%, or the equivalent amount of a risperidone salt of the total weight percentage of the formulation. In various embodiments, concentrations of risperidone, or the equivalent amount of a risperidone salt, in the formulations are (in mg/mL) 250, 251, 252, 253, 254, 255, 256, 257, 258, 259, 260, 261, 262, 263, 264, 265, 266, 267, 268, 269, 270, 271, 272, 273, 274, 275, 276, 279, 280, 281, 282, 283, 284, 285, 286, 287, 288, 289, 290, 291, 292, 293, 294, 295,296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, or 400.

In some aspects, the concentration of risperidone, or the equivalent amount of a risperidone salt, in the formulations is greater than 400 mg/mL, for example (in mg/mL), 410, 420, 430, 440, 450, 460, 470, 480, 490, or 500.

The length of the polyester chain is defined by its polyester to ethylene oxide molar ratio, which is between 0.5 to 8 or 0.5 to 3.5 or 0.5 to 2.5 or 0.5 to 22.3 for the triblock copolymer and 3 to 5 or 2 to 6 or 0.8 to 13 for the diblock copolymer. Thus, for example, if polylactic acid is used the chain length is defined by the lactic acid/ethylene oxide molar ratio. In some embodiments, the polyester chain is defined by its polyester to ethylene oxide molar ratio in the triblock, which is 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9 or 10.

In some embodiments, the polyester chain is defined by its polyester to ethylene oxide molar ratio in the diblock, which is 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9 or 10.

The mass of the end-capped polyethylene glycol in the diblock copolymer can range from 164 Da to 2,000 Da or from 100 Da to 2 kDa or from 100 Da to about 2,200 Da. It can range in the lower 100 to 300 Da range or in the 1 kDa to 2 kDa range. In some embodiments, the size of the end-capped polyethylene glycol chain ranges from (Da) 200, 300, 400, 500, 600, 700, 800, 900, 1000, 1100, 1200, 1300, 1400, 1500, 1600, 1700, 1800, 1900, 2000, 2100 or 2200.

The size of the polyethylene glycol chain in the triblock copolymer ranges from 200 Da to 12 kDa in the biodegradable drug delivery composition or it can range from 400 Da to 12 kDa or 194 Da to 12 kDa. In some embodiments, the size of the polyethylene glycol chain ranges from (Da) 200, 300, 400, 500, 600, 700, 800, 900, 1000, 1100, 1200, 1300, 1400, 1500, 1600, 1700, 1800, 1900, 2000, 2100, 2200, 2300, 2400, 2500, 26900, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, or 5000.

The triblock copolymer is present in the risperidone formulation in an amount of 3.0% to 45% (w/w %) of the total weight of the formulation. In another aspect the triblock copolymer is present in the risperidone formulation in an amount of 6% to 10% (w/w %) of the total weight of the formulation. In yet another aspect the triblock copolymer is present in the risperidone formulation in an amount of 20% to 40% (w/w %) of the total weight of the formulation. In some embodiments, the triblock copolymer is present in the risperidone formulation in an amount of 3% to 20% (w/w %) of the total weight of the formulation. In another aspect the triblock copolymer is present in the risperidone formulation in an amount of 5% to 17% (w/w %) of the total weight of the formulation. In another aspect the triblock copolymer is present in the risperidone formulation in an amount of 7% to 12% (w/w %) of the total weight of the formulation. In another aspect the triblock copolymer is present in the risperidone formulation in an amount of 5% to 15% (w/w %) of the total weight of the formulation. In yet another aspect the triblock copolymer is present in the risperidone formulation in an amount of about 3%, 3.5%, 4%, 4.5%, 5%, 5.5%, 6%, 6.5%, 7%, 7.5%, 8%, 8.5%, 9%, 9.5%, 10%, 10.5%, 11%, 11.5%, 12%, 12.5%, 13%, 13.5%, 14%, 14.5%, 15%, 15.5%, 16%, 16.5%, 17%, 17.5%, 18%, 18.5%, 19%, 19.5%, 20% (w/w %) of the total weight of the formulation. In some embodiments, the triblock copolymer is present in the risperidone formulation in an amount of about 10% (w/w) of the total weight of the formulation. In some embodiments, the triblock copolymer is a poly(D,L-lactide)-co-poly(ethylene glycol)-co-poly(D,L-lactide).

The diblock copolymer can be present in the risperidone formulation (biodegradable drug composition) in an amount of 8% to 50% (w/w %) of the total weight of the composition. In another aspect the diblock copolymer is present in the risperidone formulation in an amount of 10% to 20% (w/w %) of the total weight of the formulation. In yet another aspect the diblock copolymer is present in the risperidone formulation in an amount of 20% to 40% (w/w %) of the total weight of the formulation. In some aspects, the diblock copolymer can be present in the risperidone formulation in an amount of 6% to 30% (w/w %) of the total weight of the formulation. In another aspect the diblock copolymer is present in the risperidone formulation in an amount of 8% to 30% (w/w %) of the total weight of the formulation. In some aspects of the methods of the invention, the diblock copolymer is present in an amount of about 8% to 25% (w/w %) of the total weight of the formulation. In another aspect the diblock copolymer is present in an amount of 10% to 25% (w/w %) of the total weight of the formulation. In some aspects of the methods of the invention, the diblock copolymer is present in an amount of about 10% to 20% (w/w %) of the total weight of the formulation. In yet another aspect the diblock copolymer is present in an amount of 6%, 6.5%, 7%, 7.5%, 8%, 8.5%, 9%, 9.5%, 10%, 10.5%, 11%, 11.5%, 12%, 12.5%, 13%, 13.5%, 14%, 14.5%, 15%, 15.5%, 16%, 16.5%, 17%, 17.5%, 18%, 18.5%, 19%, 19.5%, 20%,20.5%, 21%, 21.5%, 22%, 22.5%, 23%, 23.5%, 24%, 24.5%, 25%, 25.5%, 26%, 26.5%, 27%, 27.5%, 28%, 28.5%, 29%, 29.5%, 30% (w/w %) of the total weight of the formulation. In some embodiments, the diblock copolymer is present in the risperidone formulation in an amount of about 15% (w/w) of the total weight of the formulation. In some embodiments, the diblock copolymer is methoxy-poly(ethylene glycol)-co-poly(D,L-lactide).

The copolymers are present in the pharmaceutical risperidone formulations in an amount of 20% to 50% (w/w %) of the total weight of the composition. In another aspect the total weight of the copolymers present in the biodegradable drug composition is 30% to 50% (w/w %) of the total weight of the composition. In yet another aspect the copolymers are present in the biodegradable drug composition at 40% to 50% (w/w %) of the total weight of the composition.

In preferred aspects, the total amount of the triblock copolymers and the diblock copolymers ie, poly(D,L-lactide)-co-poly(ethylene glycol)-co-poly(D,L-lactide) and methoxy-poly(ethylene glycol)-co-poly(D,L-lactide) are dissolved in solvent, ie DMSO and are present in the risperidone formulation (biodegradable drug composition or pharmaceutical formulations) in an amount of 20% to 45% (w/w %) of the total weight of the formulation. In other preferred aspects, the total amount of the triblock copolymer and diblock copolymer present in the risperidone formulations used herein is 20% to 30% (w/w %). In some embodiments of the methods of the invention, the triblock and diblock copolymers are present in a total amount of about 25% to about 45% (w/w %) of the total weight of the formulation. In yet another aspect the copolymers are present in the biodegradable drug formulation at about 20%, 20.5%, 21%, 21.5%, 22%, 22.5%, 23%, 23.5%, 24%, 24.5%, 25%, 25.5%, 26%, 26.5%, 27%, 27.5%, 28%, 28.5%, 29%, 29.5%, 30%, 30.5%, 31%, 31.5%, 32%, 32.5%, 33%, 33.5%, 34%, 5%, 35%, 35.5%, 36%, 36.5%, 37%, 37.5%, 38%, 38.5%, 39%, 39.5%, 40%, 40.5%, 41%, 41.5%, 42%, 42.5%, 43%, 43.5%, 44%, 44.5%, or 45% (w/w %) of the total weight of the formulation. In yet another embodiment, the copolymers ie, poly(D,L-lactide)-co-poly(ethylene glycol)-co-poly(D,L-lactide) and methoxy-poly(ethylene glycol)-co-poly(D,L-lactide) are present in the biodegradable drug formulation at about 25% (w/w %) of the total weight of the formulation.

The ratio of the biodegradable triblock copolymer (b) and the biodegradable diblock copolymer (c) in the risperidone formulation is 1:3 to 1:8 or 1:1 to 1:19 or 3:2 to 1:19 in the pharmaceutical formulations of the invention.

In one embodiment, the ratio of the biodegradable triblock copolymer and the biodegradable diblock copolymer in the risperidone formulation is selected from 3:2, 1:1, 1:2 1:3, 1:4, 1:5, 1:6, 1:7 and 1:8 or 1:1, 1:2, 1:3, 1:4, 1:5, 1:6, 1:7, 1:8, 1:9, 1:10, 1:11, 1:12, 1:13, 1:14, 1:15, 1:16, 1:17, 1:18 and 1:19. In some embodiments, the ratio of the biodegradable triblock copolymer and the biodegradable diblock copolymer in the risperidone formulation is about 1:1.5.

In some embodiments, the ratio of the biodegradable triblock copolymer and the biodegradable diblock copolymer is 3:2. In other embodiments, the ratio of the biodegradable triblock copolymer and the biodegradable diblock copolymer is 1:4. In yet other embodiments, the ratio of the biodegradable triblock copolymer and the biodegradable diblock copolymer is 2:3.

The pharmaceutical formulations used in the methods of the disclosure can further comprise a pharmaceutically acceptable carrier, adjuvant or vehicle. An acceptable carrier can be saline, buffered saline and the like. The adjuvant can be formulated simultaneously when mixing the drug. In this regard the adjuvants that can be used are alum, aluminum phosphate, calcium phosphate, MPL™, CpG motifs, modified toxins, saponins, endogenous stimulatory adjuvants such as cytokines, Freunds complete and incomplete adjuvants, ISCOM type adjuvants, muramyl peptides and the like.

The pharmaceutical formulations used in the methods of the invention include an organic solvent. In preferred embodiments, the organic solvent is a water-soluble organic solvent. The organic solvent that can be used in the methods described herein are selected from the group of: benzyl alcohol, benzyl benzoate, diethylene glycol dimethyl ether (Diglyme), diethylene glycol monoethyl ether (DEGMEE), dimethyl isosorbide (DMI), dimethyl sulfoxide (DMSO), ethyl acetate, ethyl benzoate, ethyl lactate, ethylene glycol monoethyl ether acetate, glycerol formal, methyl ethyl ketone, methyl isobutyl ketone, N-ethyl-2-pyrrolidone, N-methyl-2-pyrrolidinone (NMP), pyrrolidone-2, tetraglycol, triacetin, tributyrin, tripropionin (tripro), or triethylene glycol dimethyl ether (triglyme) and mixtures thereof. A preferred organic solvent is the water soluble organic solvent DMSO.

The organic solvent is present in an amount of 40% to 74% (w/w %) of the total composition. In another aspect the organic solvent used in the preparation of the biodegradable drug delivery composition is present in an amount of 50% to 60% (w/w %) of the total composition. In yet another aspect the solvent used in the preparation of the biodegradable drug delivery composition is present in an amount of 60% to 70% (w/w %) of the total composition. The organic solvent can be present in an amount of 15% to 45% or 40% to 74% (w/w %) of the total formulation. In another aspect the organic solvent used in the preparation of the pharmaceutical formulations is present in an amount of 40% to 50% (w/w %) of the weight of the total formulation.

In some embodiments, the organic solvent is DMSO. Triglycerides such as triacetin or tripropionin may also be included with the DMSO. The amount of DMSO that can be used in the pharmaceutical formulations and the methods disclosed herein can be from 35% to 55% (w/w %), preferably from 35% to 45% (w/w %). In another embodiment, the organic solvent is dimethyl sulfoxide (DMSO) and is present in an amount of about 45% (w/w %) of the weight of the total formulation. In one aspect the solvent, ie, DMSO may further include a triglyceride such as triacetin, tripropionin or mixtures thereof, in an amount of 10% to 15% (w/w %) of the weight of the total formulation.

In the biodegradable drug delivery compositions, also referenced herein inter alia as pharmaceutical formulations, of the present disclosure, the amount of risperidone is released gradually over an extended period of time. This slow release can be continuous or discontinuous, linear or non-linear and can vary due to the composition of the triblock copolymer and diblock copolymer. Thus, the higher the lactic acid content of the triblock and diblock copolymers in comparison with the polyethylene glycol content, as well as the amount of triblock and diblock copolymers present in the biodegradable drug composition the longer the release of the active principle or drug. In other words, the higher the LA/EO molar ratio and the greater weight percentage of the triblock and diblock copolymers, the longer it will take for the active principle to be released from the drug composition. Volume may also affect release, with active principle released over a longer period of time from a larger volume than from a smaller volume, see data in example 2, below.

In one aspect, the biodegradable drug delivery composition delivers, ie, releases the risperidone, ie therapeutic levels to the subject, for at least 21 days, and in specific embodiments for at least 28 days or for at least 56 days. In one aspect, the biodegradable drug delivery composition can deliver the risperidone for 21 days up to about 90 days. In another aspect, the biodegradable drug delivery composition can deliver the risperidone for about 21 to 30 days or for about 28 to 31 days. In another aspect, the biodegradable drug delivery composition can deliver the risperidone for at least 28, 29 or 30 days. In another aspect, the biodegradable drug delivery composition can deliver the risperidone for about 56 to 63 days. In another aspect, the biodegradable drug delivery composition can deliver the risperidone for at least 56, 57, 58 59 or 60 days. In one aspect, the biodegradable drug delivery composition can deliver the risperidone for at least 90 days.

In the methods disclosed herein, the administration results in an effective amount of risperidone being released from the formulation to treat the subject's psychiatric disease or disorder for an extended period of time. In some embodiments, the administration is effective in treating the subject's psychiatric disease or disorder for a duration of 21 days to 90 days. In some embodiments, the administration is effective in treating the subject's psychiatric disease or disorder for 28 days to 90 days. In other embodiments, the administration is effective in treating the subject's psychiatric disease or disorder for 28 or 31 days to 56 or 62 days. In some embodiments, the administration is effective in treating the subject's psychiatric disease or disorder for 28 days or for 31 days. In other embodiments, the administration is effective in treating the subject's psychiatric disease or disorder for 42 days. In other embodiments, the administration is effective in treating the subject's psychiatric disease or disorder for 56 days or for 62 days. In other embodiments, the administration is effective in treating the subject's psychiatric disease or disorder for 84 days or for 90 days. The dosing may be repeated after each period of, for example 28 or 56 days.

In most preferred aspects of the methods of the invention, the release of risperidone from the pharmaceutical formulation is such that therapeutically effective levels of risperidone are achieved within 24 hours of subcutaneous administration. With therapeutically effective levels of risperidone achieved within 24 hours of subcutaneous administration, alternative, immediate release risperidone formulations (for example, immediate release oral formulations or immediate release injectable formulations) are not required to ensure adequate risperidone levels in a subject. That is, a "loading dose" or supplemental oral dose of risperidone or supplement parenteral dose of risperidone is not required in the methods of the invention. Thus, in some embodiments, the methods are implemented in the absence of a loading dose or supplemental oral risperidone or supplemental parenteral risperidone or other antipsychotic drug. One such embodiment is administration of the pharmaceutical formulation disclosed herein to a subject following a missed dose. As no loading dose is required, a patient who missed a dose (i.e. a Q1M or Q2M dose depending on the individual's regimen) is able to receive the pharmaceutical formulation as soon as possible following the missed dose event.

Using the methods of the invention, a therapeutically effective amount of the risperidone will have been released by a target date. Thus, with an amount of a "once monthly formulation," about 50 w %, or about 50 w % to about 80 w %, for example, 50, 55, 60, 65, 70, 75, or 80 w %, of the risperidone (or salt thereof) will have been cumulatively released by 28 days or 29, 30 or 31—days post administration, preferably with a near linear release profile. The term "cumulatively released" as used herein, refers to the total amount of risperidone (by weight) released by a particular point in time, as a percentage of the total amount of risperidone in the formulation. Cumulative release can be measured by, for example, the in vitro release (IVR) methods known in the art and described herein. Thus, for example, with an amount of a "once every two months formulation," about 75 w %, or about 75 w % to about 98 w %, for example, 75, 70, 85, 90, 91, 92, 93, 94, 95, 96, 97, or about 98 w %, of the risperidone (or salt thereof) will have been cumulatively released by 56 days or 57, 58, 59, 60, 61 or 62—days post administration, preferably with a near linear release profile. Thus, provided herein is a sustained release of risperidone over the desired time, ie, at least 28 days and up to two months.

In some embodiments, less than about 15 w % of the risperidone in the formulation is cumulatively released at 24 hours post administration. In other embodiments, about 7 w % to about 15 w %, for example, 7, 8, 9, 10, 11, 12, 13, 14, or 15 w % of the risperidone in the formulation is cumulatively released at 24 hours post administration.

In some embodiments, about 50 w % to about 80 w %, for example, 50, 55, 60, 65, 70, 75, or 80 w % of the risperidone (or salt thereof) in the formulation is cumulatively released at 28 days or at 28-31 days post administration. In some embodiments, about 50 w % to about 80 w %, for example, 50, 55, 60, 65, 70, 75, or 80 w % of the risperidone (or salt thereof) in the formulation is cumulatively released at 28 days post administration.

In some embodiments, about 70 w % to about 98 w %, for example, 75, 70, 85, 90, 91, 92, 93, 94, 95, 96, 97, or about 98 w %, of the risperidone (or salt thereof) in the formulation is cumulatively released at 56 days or at 56-62 days post administration. In some embodiments, about 70 w % to about 98 w %, for example, 75, 70, 85, 90, 91, 92, 93, 94, 95, 96, 97, or about 98 w %, of the risperidone (or salt thereof) in the formulation is cumulatively released at 56 days post administration.

The pharmaceutical formulations used in the methods of the disclosure are injectable liquids at room temperature and can be injected through a syringe without excessive force. The compositions are also in situ forming and biodegradable, turning into solid or semi solid implants when injected into the animal which enables the release of risperidone over time.

In some aspects of the methods of the invention, the pharmaceutical formulation is administered from a pre-filled syringe (PFS). A PFS is a syringe which contains an appropriate amount of the pharmaceutical formulation and which is ready for subcutaneous administration, preferably by a health care professional. The ready to use PFS disclosed herein provides a significant development in the field of subcutaneously administered LAI in that no laborious or time consuming pre-administration reconstitution is required. In some embodiments of the methods of the invention, the pharmaceutical formulation is administered from a single pre-filled syringe. In other embodiments, the pharmaceutical formulation is administered from more than one pre-filled syringe, for example, from 2, 3, 4, 5, or 6 or more pre-filled syringes.

According to the disclosure, the volume of the pharmaceutical formulation in the pre-filled syringe is 1 mL or less. In some embodiments, the volume of the pharmaceutical formulation in the pre-filled syringe is between 0.1 mL and 0.9 mL. In some embodiments, the volume of the pharmaceutical formulation in the pre-filled syringe is between 0.1 mL and 0.8 mL. In some embodiments, the volume of the delivered dose of risperidone formulation in the pre-filled syringe is between 0.14 mL and 0.7 mL. In some embodiments, the volume of the pharmaceutical formulation in the pre-filled syringe is between 0.1 mL and 0.5 mL. In some embodiments, the volume of the pharmaceutical formulation in the pre-filled syringe is about 0.1 mL. In some embodiments, the volume of the pharmaceutical formulation in the pre-filled syringe is about 0.2 mL. In some embodiments, the volume of the pharmaceutical formulation in the pre-filled syringe is about 0.3 mL. In some embodiments, the volume of the pharmaceutical formulation in the pre-filled syringe is about 0.4 mL. In some embodiments, the volume of the pharmaceutical formulation in the pre-filled syringe is about 0.5 mL. In some embodiments, the volume of the pharmaceutical formulation in the pre-filled syringe is about 0.6 mL. In some embodiments, the volume of the pharmaceutical formulation in the pre-filled syringe is about 0.7 mL. In some embodiments, the volume of the pharmaceutical formulation in the pre-filled syringe is about 0.8 mL. In some embodiments, the volume of the pharmaceutical formulation in the pre-filled syringe is about 0.9 mL. In some embodiments, the volume of the pharmaceutical formulation in the pre-filled syringe is about 1.0 mL. Volume in the PFS refers to the delivered volume, ie, the volume administered to a subject, an extra volume might be needed in the PFS to cover the dead volume of the syringe coupled to the needle.

In some embodiments, the amount of risperidone in the pharmaceutical formulation is 50 mg in a volume of about 0.14 mL. In some embodiments, the amount of risperidone in the pharmaceutical formulation is 100 mg in a volume of about 0.28 mL. In some embodiments, the amount of risperidone in the pharmaceutical formulation is 125 mg in a volume of about 0.35 mL. In some embodiments, the amount of risperidone in the pharmaceutical formulation is 150 mg in a volume of about 0.42 mL. In some embodiments, the amount of risperidone in the pharmaceutical formulation is 200 mg in a volume of about 0.56 mL. In some embodiments, the amount of risperidone in the pharmaceutical formulation is 250 mg in a volume of about 0.7 mL. In some embodiments, the amount of risperidone in the pharmaceutical formulation is 300 mg in a volume of about 0.84 mL. In some embodiments, the amount of risperidone in the pharmaceutical formulation is 50 mg in a volume of about 0.1 mL. In some embodiments, the amount of risperidone in the pharmaceutical formulation is 100 mg in a volume of about 0.2 mL. In some embodiments, the amount of risperidone in the pharmaceutical formulation is 125 mg in a volume of about 0.3 mL. In In some embodiments, the amount of risperidone in the pharmaceutical formulation is 150 mg in a volume of about 0.4 mL. In some embodiments, the amount of risperidone in the pharmaceutical formulation is 200 mg in a volume of about 0.6 mL. In some embodiments, the amount of risperidone in the pharmaceutical formulation is 250 mg in a volume of about 0.7 mL. These doses provide a therapeutic level of risperidone comparable to 2 mg/day (50 mg once a month or 100 mg once every two months), 3 mg/day (75 mg once a month or 150 mg once every two months), 4 mg/day (100 mg once a month or 200 mg once every two months) and 5 mg/day (125 mg once a month or 250 mg once every two months) of oral risperidone.

In some embodiments of the methods and compositions PFS and kits disclosed herein, the long acting injectable risperidone formulation comprises 30% risperidone, 45% (w/w) DMSO, 10% (w/w) triblock copolymer, 15% (w/w) diblock copolymer, 25% (w/w) total copolymers. In some embodiments, the ratio of triblock copolymer to diblock copolymer may be 3:2 to 2:3.

In some embodiments of the methods and compositions, PFS and kits disclosed herein, the risperidone formulation disclosed herein is an extended release injectable suspension.

In some embodiments of the of the methods and compositions, PFS and kits disclosed herein, the long acting injectable risperidone formulations are those comprising 25% (w/w) triblock copolymer and diblock copolymer of the total weight percentage of the formulation.

In some embodiments of the of the methods and compositions, PFS and kits disclosed herein, the long acting injectable risperidone formulations are those comprising 45% DMSO of the total weight percentage of the formulation.

In other embodiments of the of the methods and compositions, PFS and kits disclosed herein, the long acting injectable risperidone formulations are those comprising about 30% risperidone or the equivalent of a pharmaceutically acceptable salt thereof of the total weight percentage of the formulation.

Many psychiatric disorders are chronic conditions that require continuous treatment to moderate symptoms and prevent relapse. Thus, the methods disclosed herein are capable of being implemented over extended periods of time. In some embodiments, the methods are implemented over a period of at least 6 months. In other embodiments, the methods are implemented over a period of at least 12 months. In other embodiments, the methods are implemented over a period of at least 15 months. In other embodiments, the methods are implemented over a period of at least 24 months.

In patients with severe renal or hepatic impairment, the methods may be implemented by titrating with oral risperidone to at least 2 mg once daily prior to initiating treatment with the long acting injectable risperidone formulations disclosed herein. If tolerated, the patient may be switched to the 50 mg once monthly dose of the long acting injectable risperidone formulation.

Further provided is a prefilled syringe for subcutaneously administering a long acting injectable risperidone formulation, said prefilled syringe comprising i. a long acting injectable risperidone formulation wherein said formulation comprises a) risperidone, or a pharmaceutically acceptable salt thereof, at a concentration of about 250-400 mg/mL, equivalent to risperidone;

b) a biodegradable triblock copolymer having the formula:

poly(lactic acid)$_v$-poly(ethylene glycol)$_w$-poly(lactic acid)$_x$ wherein v and x are the number of repeat units ranging from 24 to 682 and w is the number of repeat units ranging from 4 to 273 and v=x or v≠x;

c) a biodegradable diblock copolymer having the formula:

methoxy-poly(ethylene glycol)$_y$-poly(lactic acid)$_z$, wherein y and z are the number of repeat units, wherein y is the number of repeat units ranging from 3 to 50 and z is the number of units ranging from 7 to 327; wherein the ratio of the biodegradable triblock copolymer of (b) and the biodegradable diblock copolymer of (c) is 1:3 to 1:8 or 1:1 to 1:19 or 3:2 to 1:19, in said formulation, which is insoluble in an aqueous environment, and ii. a needle having a gauge number equal to or greater than 21 and/or a length equal to or shorter than ⅝ inch.

Further provided is a kit comprising:

i. a prefilled syringe comprising a long acting injectable risperidone formulation wherein said formulation comprises a) risperidone, or a pharmaceutically acceptable salt thereof, at a concentration of about 250-400 mg/mL, equivalent to risperidone;

b) a biodegradable triblock copolymer having the formula:

poly(lactic acid)$_v$-poly(ethylene glycol)$_w$-poly(lactic acid)$_x$ wherein v and x are the number of repeat units ranging from 24 to 682 and w is the number of repeat units ranging from 4 to 273 and v=x or v≠x;

c) a biodegradable diblock copolymer having the formula:

methoxy-poly(ethylene glycol)$_y$-poly(lactic acid)$_z$, wherein y and z are the number of repeat units, wherein y is the number of repeat units ranging from 3 to 50 and z is the number of units ranging from 7 to 327; wherein the ratio of the biodegradable triblock copolymer of (b) and the biodegradable diblock copolymer of (c) is 1:3 to 1:8 or 1:1 to 1:19 or 3:2 to 1:19, in said formulation, which is insoluble in an aqueous environment;

ii. a needle having a gauge number equal to or greater than 21 and/or a length equal to or shorter than ⅝ inch; and iii. instructions for use.

In some embodiments, the kit is a single use kit, ie containing a single dose prefilled syringe and a 21 gauge, ⅝-inch needle. In some embodiments, the kit is provided in a tray, which may be a blister tray. In some embodiments, further provided is a means for physically protecting the prefilled syringe from for example, light, including ambient light. In non-limiting embodiments, the means is a carton, a box, a bag or aluminum foil wrap. In some embodiments, the means is a carton. In some embodiments the needle is a safety needle. The safety needle may include a safety shield and/or a needle sheath, and may be packaged in a separate sterile pouch. The PFS may be any syringe suitable for administration of a drug polymer suspension. In some embodiments, the syringe is a glass syringe or a polymer syringe. In some embodiments, the syringe comprises a white to off-white opaque suspension. In specific embodiments, each prefilled syringe contains a sterile, white to off-white opaque viscous suspension, for subcutaneous use and 50 mg, 75 mg, 100 mg, 125 mg, 150 mg, 200 mg, or 250 mg risperidone. In some embodiments, the PFS is a glass syringe comprising a cap with a collar covering the needle hub. The syringe may further include a syringe barrel label which includes the dose and an expiration date. In various embodiments, the risperidone solution is viscous and instructions for use include a step of holding the syringe at or near the collar and flicking the syringe forcefully, for example with a downward whipping motion, about three times to move any (air) bubble from the syringe to the cap region of the syringe. Such bubble may appear to be partially opaque. When the bubble is at the cap, the cap may be removed from a vertically held syringe by bending and snapping the cap off. The needle may be attached to the needle hub inside of the collar. Further provided is a kit comprising the Risperidone formulation in a vial and a syringe for administration.

In some embodiments of the methods disclosed herein, the long acting injectable risperidone formulation in the prefilled syringes of the invention is stable at room temperature (20 to 25° C.) for up to 30 days. In some embodiments the formulation is stable at room temperature for at least 90 days. In other embodiments, the long acting injectable risperidone formulation in the prefilled syringes of the invention is stable at 25° C./60% RH for up to 6 months. The long acting injectable risperidone formulation may be returned to refrigerated storage (2 to 8° C.) within 90 days as long as unopened. In other embodiments, the long acting injectable risperidone formulation in the prefilled syringes of the invention is stable and may be stored at 2 to 8° C. for at least 12 months, at least 24 months, at least 30 months or at least 36 months. In some embodiments, the risperidone formulation is a solid at refrigerated temperatures (2 to 8° C.) and liquid at room temperature (20 to 25° C.). In other embodiments, the long acting injectable risperidone formulation in the prefilled syringes of the invention is stable after 3 cycles of 2 days at −20° C. followed by 2 days at 25° C./60% RH. In other embodiments, the long acting injectable risperidone formulation in the prefilled syringes of the invention is stable after 2 weeks at −20° C. followed by 2 weeks at 2 to 8° C. In other embodiments, the long acting injectable risperidone formulation in the prefilled syringes of the invention is stable after at least 30 days at 20 to 25° C. followed by up to 36 months at 2 to 8° C. and up to 30 days at 20 to 25° C.

In some embodiments, provided is a method of treating a psychiatric disease or disorder in a subject, comprising subcutaneously administering to the subject at a frequency of no more than once every 28 days 1 mL or less of a long acting injectable risperidone formulation comprising:

a) risperidone, or a pharmaceutically acceptable salt thereof, at a concentration of about 250-400 mg/mL, equivalent to risperidone;

b) a biodegradable triblock copolymer having the formula: poly(lactic acid)v-poly(ethylene glycol)w,-poly (lactic acid)x wherein v and x are the number of repeat units ranging from 24 to 682 and w is the number of repeat units ranging from 4 to 273 and v=x or v≠x;

c) a biodegradable diblock copolymer having the formula: methoxy-poly(ethylene glycol)$_y$-poly(lactic acid)$_z$, wherein y and z are the number of repeat units, wherein y is the number of repeat units ranging from 3 to 50 and z is the number of repeat units ranging from 7 to 327;

wherein the ratio of the biodegradable triblock copolymer of (b) and the biodegradable diblock copolymer of (c) is 1:3 to 1:8 or 1:1 to 1:19 or 3:2 to 1:19, in said formulation, which is insoluble in an aqueous environment;

wherein the long acting injectable risperidone formulation is stored unopened at room temperature (20° C.-25° C.) for up to 90 days prior to administration or is stored unopened and refrigerated at (2° C.-8° C.) for up to 36 months prior to administration.

In some embodiments, the long acting injectable risperidone formulation is allowed to come to room temperature for at least 30 minutes prior to administration.

Methods for preparing the pharmaceutical formulations used in the methods of the invention are disclosed in, for example U.S. Pat. No. 9,023,897, incorporated by reference herein.

Some mPEG-OH may include a small amount of OH-PEG-OH. By following the methods of disclosed herein, the final product may be mPEG-PLA which includes a small amount of PLA-PEG-PLA.

For the foregoing embodiments, each embodiment disclosed herein is contemplated as being applicable to each of the other disclosed embodiments. For instance, the elements recited in the method embodiments can be used in the prefilled syringe or kit embodiments described herein and vice versa.

Disclosures of the publications cited throughout are hereby incorporated by reference in their entireties into this application in order to more fully describe the state of the art as of the date of the invention described herein.

The following examples are for illustrative purposes, and are intended to be non-limiting. Those of skill in the art will readily recognize a variety of features which can be changed or modified to yield essentially the same results.

EXAMPLES

Example 1. In Vitro Release (IVR) Model

The in vitro model set-up was based on the USP II dissolutest technique, where the in vitro release of the drug formulations are followed up in tubes containing an aqueous buffer maintained at +37° C. under constant agitation. Approximately 100 or 170 mg of the formulations were injected using a 0.5-mL syringe mounted with a 23G needle inside a Falcon® tube prefilled with 50 mL of Krebs Ringer-Tris buffer (KRT, pH 7.4), and immediately incubated at +37° C. under constant orbital agitation rate (180 rpm). The depots freely formed instantly upon contact with the buffer due to the insolubility of the copolymers in water, which is intended to mimic the implant formation in the subcutaneous tissue in vivo.

The in vitro release for each formulation was performed in duplicate. At predetermined time-points, the release buffer was sampled and refreshed. Special care was given to avoid losing depot fragments (when present) during buffer replacement. When an IVR was stopped, the amount of active agent in the remaining depot was determined by HPLC to assess the mass balance and ascertain that the remaining amount of active agent in the depot correlated with the cumulative release. Briefly, the remaining depot was solubilized in 10 mL of acetonitrile. The solution was mixed using a vortex mixer until complete dissolution and then, 10 mL of ultra-pure water were added. The mixture was shaken once again prior to HPLC analysis.

Preparation of stock solutions, standard and quality control samples

A stock solution was prepared by dissolving risperidone in acetonitrile/$H_2O$ mixture (50/50 v/v) in order to achieve a 200 μg/mL solution of risperidone. This "mother solution" was stored at +2-8° C. and showed stability over a minimum of 5 months. Starting from this mother solution, calibration standards were prepared by dilution in the same sample solvent mixture as above. Six dilutions were performed to obtain calibration standards of 1, 5, 10, 25, 50, 100 and 200 μg/mL.

Additional working solutions containing 0.10, 0.25, 0.50 and 0.75 μg/mL were prepared likewise by further diluting the standard 10 μg/mL. These further diluted samples were specifically used to investigate the limit of detection (LOD) and the limit of quantification (LOQ) of the chromatographic method.

A series of three accuracy standards (10, 100 and 200 μg/mL) were also independently prepared by dilution of the starting mother solution (200 μg/mL) using the same sample solvent as described above. These standards were used to assess the level of accuracy of the developed method.

Instruments and Chromatographic Conditions

HPLC equipment of a Waters 269S Separation Module equipped with a Waters 2487 Dual wavelength UV detector set at 280 nm (corresponding to the maximum absorption wavelength of risperidone) was used. The separation column (150 mm×4.6 mm) was packed with Kinetex C18 of 5-μm particle size. The following Table 1 summarizes the mobile phase gradient used in this study. A flow rate of 1 mL/min was used, and the column temperature was set to +30° C. The injection volume of the sample was 10 μL.

TABLE 1

| Time (min) | Acetonitrile (%) | $H_2O/CH_3COONH_4$ (%) |
|---|---|---|
| 0 | 25 | 75 |
| 7 | 70 | 30 |
| 7.5 | 95 | 5 |
| 9 | 25 | 75 |
| 12 | 25 | 75 |

According to the above conditions, the retention time of risperidone is 5.5 min. Linearity was assessed throughout the analysis of the standards (1, 5, 10, 25, 50, 100 and 200 μg/mL). Calibration was set based on each standard peak area. The curve of best fit was determined using linear regression analysis and gave a $R^2$>0.9999. The accuracy was determined by calculating the relative standard deviation (RSD) between the mean assayed concentration of three accuracy standards, namely 10, 100 and 200 μg/mL. The RSD was <0.1% for all accuracy standards, and the recovery ranged between 99.7 to 101.9% of the target concentration. The LOD was calculated to be 0.1 μg/mL (corresponding to three times the average baseline noise). The LOQ was assessed as the lowest concentration that allowed a 90% recovery of the target drug concentration. LOQ was found to be 0.5 μg/mL.

Injectability was measured according to a standardized operating procedure. The method was inspired from the previous work of Cilurzo et al. The apparatus used for injectability measurements was a Friction Tester FTPlus (Lloyd Instruments) connected with the Nexygen Plus software. Briefly, the injectability test was carried out by fixing the crosshead speed to 1.1 mL/min, using a 1-mL CODAN syringe mounted with a 23G or 25G needle. The syringe was prefilled with at least 0.5 mL of the formulation to be tested. The Dynamic Glide Force (DGF) (i.e. the average force in Newton (N) required to sustain the movement of the plunger to expel the formulation out of the syringe) was then measured in each study. Cilurzo et al, demonstrated "this parameter is representative of a manual syringe delivery to patient." (Cilurzo, F, et al., Injectability Evaluation: An Open Issue. AAPS PharmSciTech. 2011 2: 604-609).

Example 2. Risperidone Formulations

The long acting injectable risperidone formulation comprises an amount of risperidone of at least 250 mg/mL, for example, at least 300 mg/mL and up to about 400 mg/mL for an injection volume of <1 mL.

Preparation of Risperidone Particles

Particles of risperidone may be prepared using supermicronization, micronization or milled sourcing. The particle size distribution (PSD) of the risperidone particles in the formulations may be as follows:

D10 Not more than (NMT) 20 μm;

D50 NMT 40 μm;

D90 NMT 70 μm.

D50 refers to the median diameter of the particles, for example 50% of the particles have a diameter greater than 40 um and 50% of the particles have a diameter equal to or less than 40 um. The particle size distribution of the microparticles is determined by conventional methods such as dynamic or static light-scattering of an aqueous dispersion.

Dose Adjustment by Volume Injection

A 2-fold increase in injection volume resulted in a non-proportional increase in the release kinetics as evidenced by a shift of the 75% cumulative release between 125 mg and 250 mg depot. A depot of 250 mg would release its risperidone cargo over a longer period of time than would a 125 mg depot.

Exemplary formulations are shown in Table 2. Given percentages are weight percentages from total formulation composition.

TABLE 2

| Formulations: | RSP mg/mL | TB (PaRb)* | % TB | DB (dPaRb)** | % DB | % total copolymer | Ratio TB:DB | % DMSO |
|---|---|---|---|---|---|---|---|---|
| F1L | 120 | P1R4 | 24 | dP0.35R5.5 | 16 | 40 | 3:2 | 50 |
| F2L | 180 | P1R4 | 24 | dP0.35R5.5 | 16 | 40 | 3:2 | 45 |
| F3L | 240 | P1R4 | 24 | dP0.35R5.5 | 16 | 40 | 3:2 | 40 |
| F3 | 300 | P2R3. | 8 | dP2R3 | 12 | 20 | 2:3 | 55 |
| F8 | 360 | P2R3. | 8 | dP0.35R5.5 | 12 | 20 | 2:3 | 50 |
| F11 | 360 | P1R4 | 18 | dP0.35R5.5 | 12 | 30 | 3:2 | 40 |
| F15 | 360 | P1R4 | 10 | dP0.35R5.5 | 15 | 25 | 2:3 | 45 |
| F24 | 360 | P1R6 | 10 | dP0.35R5.5 | 15 | 25 | 2:3 | 45 |
| F25 | 360 | P1R6 | 10 | dP0.35R8 | 15 | 25 | 2:3 | 45 |
| F28 | 480 | P1R4 | 8 | dP0.35R5.5 | 12 | 20 | 2:3 | 40 |
| F29 | 360 | P1R6 | 20 | dP2R3 | 5 | 25 | 4:1 | 45 |
| F30 | 360 | P1R6 | 17.5 | dP2R3 | 7.5 | 25 | 2.5:1 | 45 |
| F32 | 360 | P1R6 | 10 | dP1R3.5 | 15 | 25 | 2:3 | 45 |
| F33 | 360 | P1R6 | 10 | dP1R5 | 15 | 25 | 2:3 | 45 |
| F34 | 360 | P1R6 | 7.5 | dP1R5 | 17.5 | 25 | 1:2.5 | 45 |
| F36 | 360 | P1R6 | 15 | dP0.35R8 | 10 | 25 | 3:2 | 45 |
| F37 | 360 | P1R6 | 10 | dP2R3.5 | 15 | 25 | 2:3 | 45 |
| F39 | 360 | P1R6 | 11 | dP2R3 | 16.5 | 27.5 | 2:3 | 42.5 |
| F78 | 360 | P1R6 | 10 | dP2R3 | 15 | 25 | 2:3 | 45 |
| F79 | 341 | P1R6 | 17.07 | dP2R3 | 11.38 | 28.45 | 3:2 | 43.1 |
| F80 | 429 | P1R6 | 15.32 | dP2R3 | 10.22 | 25.54 | 3:2 | 38.71 |
| F81 | 288 | P1R6 | 4.79 | dP2R3 | 19.17 | 23.96 | 1:4 | 52.08 |
| F82 | 341 | P1R6 | 5.59 | dP2R3 | 22.76 | 28.45 | 1:4 | 43.1 |
| F83 | 367 | P1R6 | 13.12 | dP2R3 | 8.74 | 21.86 | 3:2 | 47.53 |
| F84 | 429 | P1R6 | 5.11 | dP2R3 | 20.43 | 25.54 | 1:4 | 38.7 |
| F85 | 401 | P1R6 | 4.79 | dP2R3 | 19.11 | 23.89 | 1:4 | 42.66 |
| F86 | 288 | P1R6 | 14.38 | dP2R3 | 9.58 | 23.96 | 3:2 | 52.08 |
| F89 | 360 | P1R6 | 5 | dP2R3 | 22.5 | 27.5 | 1:4.5 | 42.5 |
| F90 | 360 | P1R6 | 10 | dP2R3 | 17.5 | 27.5 | 1:1.75 | 42.5 |
| F93 | 360 | P1R6 | 5.5 | dP2R3 | 24.5 | 30 | 1:4.5 | 40 |

RSP = risperidone

*PaRb represents a triblock (TB) copolymer where a is the size of the PEG chain in kDa and b is the lactic acid/ethylene oxide (LA/EO) molar ratio;

**dPaRb represents a diblock (DB) copolymer where a is the size of the mPEG chain in kDa and b is the lactic acid/ethylene oxide (LA/EO) molar ratio.

Cumulative release of the formulations shown in Table 2 is provided in Tables 3 and 4. "Mean" refers to % of total release.

TABLE 3

| Time | F81 | | F82 | | F83 | | F84 | | F85 | | F86 | |
|---|---|---|---|---|---|---|---|---|---|---|---|---|
| (days) | Mean | SD | Mean | SD | Mean | SD | Mean | SD | Mean | SD | Mean | SD |
| 0.08 | 1.6 | 0.1 | 1.5 | 0.1 | 1.7 | 0.1 | 1.1 | 0.1 | 1.3 | 0.1 | 1.7 | 0.1 |
| 0.17 | 2.8 | 0.2 | 2.2 | 0.1 | 2.9 | 0.2 | 1.9 | 0.1 | 2.4 | 0.1 | 2.7 | 0.1 |
| 0.25 | 4.2 | 0.3 | 3.2 | 0.2 | 4.2 | 0.2 | 2.8 | 0.1 | 3.4 | 0.2 | 3.8 | 0.1 |
| 1 | 12.5 | 0.3 | 9.8 | 0.2 | 12.4 | 0.5 | 10.8 | 0.1 | 10.9 | 0.2 | 13.7 | 0.3 |
| 2 | 17.6 | 0.5 | 16.2 | 0.4 | 17.9 | 0.3 | 16.5 | 0.3 | 16 | 0.6 | 20.6 | 0.3 |
| 3 | 20.8 | 0.7 | 22.1 | 0.3 | 22.2 | 0.1 | 20.6 | 0.4 | 19.4 | 0.4 | 24.6 | 0.4 |
| 6 | 27.6 | 1 | 32.5 | 0.2 | 31.3 | 0.7 | 28.5 | 0.5 | 26.3 | 0.6 | 33 | 0.6 |
| 10 | 34.2 | 1 | 41.3 | 0.2 | 40.6 | 1.4 | 36.1 | 0.4 | 33.2 | 0.8 | 41.1 | 0.7 |
| 14 | 39.5 | 0.8 | 47.2 | 0.1 | | | 41.3 | 0.5 | 38.5 | 1 | 47.1 | 0.7 |
| 17 | 43.5 | 1 | 51 | 0.2 | 51.9 | 0.9 | 45.1 | 0.6 | 42.5 | 1.1 | 51.5 | 0.5 |
| 21 | 47.3 | 0.9 | 54.3 | 0.2 | 56.2 | 0.9 | 48.3 | 0.7 | 46.1 | 1.2 | 55.4 | 0.4 |
| 24 | 52.2 | 1 | 58.5 | 0.3 | 62 | 1.1 | 52.8 | 0.6 | 51 | 1.3 | 60.5 | 0.6 |
| 28 | 56.5 | 1.2 | 61.8 | 0.3 | 66.5 | 1.2 | 56.2 | 0.6 | 55 | 1.3 | 64.9 | 0.6 |
| 31 | 59.9 | 1.2 | 65 | 0.3 | 70.3 | 1.2 | 60.1 | 0.6 | 58.2 | 1.2 | 68.8 | 0.6 |
| 34 | 64.7 | 1.2 | 68.4 | 0.4 | 74.9 | 1.2 | 63.8 | 0.6 | 62.7 | 1.2 | 73.2 | 0.6 |
| 42 | 73 | 1.2 | 74 | 0.4 | 81.8 | 1.2 | 70.1 | 0.6 | 70.1 | 1.2 | 80 | 0.6 |
| 49 | 79.5 | 0.9 | 78.6 | 0.5 | 87.2 | 1.1 | 75.3 | 0.6 | 75.9 | 1.1 | 85.4 | 0.5 |
| 56 | 85.4 | 0.9 | 83.1 | 0.4 | 92.1 | 1.1 | 80.3 | 0.6 | 81.5 | 0.9 | 90.8 | 0.3 |
| 63 | 89.7 | 0.9 | 86.5 | 0.4 | 95.6 | 0.3 | 84.1 | 0.7 | 85.3 | 0.9 | 94.5 | 0.2 |
| 70 | 93.4 | 0.8 | 89.5 | 0.4 | 98.1 | 0.3 | 87.3 | 0.6 | 88.8 | 0.8 | 97.5 | 0.2 |
| 77 | 96.1 | 0.6 | 92 | 0.4 | | | 89.9 | 0.6 | 91.3 | 0.7 | | |
| 84 | | | 94.1 | 0.7 | | | 92.8 | 0.5 | 93.8 | 0.6 | | |
| 91 | | | 95.9 | 0.7 | | | 94.7 | 0.5 | 95.6 | 0.5 | | |
| 105 | | | 98.9 | 0.8 | | | 97.7 | 0.6 | 98 | 0.3 | | |
| 119 | | | | | | | 99.6 | 0.6 | | | | |

TABLE 4

| Time | F89 | | F90 | | F93 | |
|---|---|---|---|---|---|---|
| (days) | Mean | SD | Mean | SD | Mean | SD |
| 0.08 | 1.4 | 0 | 1.3 | 0 | 1.3 | 0 |
| 0.17 | 2.1 | 0.1 | 2 | 0 | 2.4 | 0.1 |
| 0.25 | 3 | 0.1 | 2.9 | 0.1 | 3.3 | 0.2 |
| 1 | 9 | 0.5 | 8.9 | 0.2 | 8.9 | 0.2 |
| 2 | 15.1 | 1 | 15.1 | 0.6 | 14.8 | 0.1 |
| 3 | 20.3 | 0.9 | 20.8 | 0.8 | 20.5 | 0.2 |
| 6 | 30.3 | 0.9 | 32.2 | 0.5 | 32 | 0.6 |
| 10 | 38.6 | 1 | 41.4 | 0.5 | 40.5 | 0.6 |
| 14 | 44 | 1.1 | 47.6 | 0.6 | 46.9 | 0.4 |
| 17 | 47.4 | 1.1 | 51.4 | 0.6 | 50.6 | 0.4 |
| 21 | 52.2 | 1.1 | 55.8 | 0.5 | 54.9 | 0.3 |
| 24 | 55.3 | 0.9 | 58.9 | 0.5 | 57.9 | 0.4 |
| 28 | 59.2 | 1.1 | 62.4 | 1 | 61.1 | 0.4 |
| 31 | 61.6 | 1.1 | 64.8 | 1 | 63.3 | 0.4 |
| 34 | 64.6 | 1.2 | 67.8 | 0.9 | 66.4 | 0.5 |
| 42 | 69.1 | 1.1 | 72.1 | 0.8 | 71 | 0.5 |
| 49 | 72.7 | 1 | 75.7 | 0.8 | 74.7 | 0.6 |
| 56 | 76.3 | 1 | 79.4 | 0.7 | 78.6 | 0.8 |
| 63 | 79.2 | 0.9 | 82.3 | 0.6 | 81.5 | 0.8 |
| 70 | 82.2 | 0.9 | 85.4 | 0.5 | 84.7 | 0.7 |
| 77 | 84.7 | 0.9 | 88.1 | 0.4 | 89 | 2.9 |
| 84 | 87.1 | 0.7 | 91 | 0.2 | 92.5 | 4.7 |
| 91 | 89.3 | 0.7 | 92.8 | 0 | 94.7 | 5.3 |
| 105 | 92.2 | 0.7 | 95.5 | 0.2 | 95.8 | 5.9 |
| 119 | 93.8 | 0.7 | 96.9 | 0.1 | 96.8 | 5.8 |
| | 94.4 | 0.6 | | | 97.3 | 5.8 |

Example 3: In Vivo Excision Study

The possibility to excise the compositions from the subcutaneous (sc) space was tested. Without wishing to be bound to any particular theory, a health care professional (HCP) may consider post-administration implant excision in case of adverse events.

Compositions were subcutaneously injected into the interscapular and flank area of rats, dogs, mini-swine and pigs.

In one study, the feasibility of locating and excising the sc injected implant for long-acting release of risperidone by clinically relevant imaging techniques ultrasound and MRI in mini-swine. Two *Sus scrofa* Yucatan mini-swine were injected sc with 50 and 150 mg risperidone formulation, corresponding to 140- and 420-μL volumes, respectively, in the flank of the animal. In addition, the animals were injected sc with 3 vehicle formulations (non-API control formulation) having a volume range of 70 to 840 μL for a total of 5 implants per animal (2 risperidone, 3 vehicle)

MRI (Magnetom Sonata Syngo 1.5 T; Siemens), ultrasound (FujiFilm Vevo MD apparatus for 15, 30, and 50 MHz frequencies), and Siemens Acuson SC2000 apparel (for 9 MHz frequency) imaging modalities were used to locate the implants at 4 hours post-injection and on days 1, 3, 6, 14, 20, 27, and 35. Excision of an implant was performed on day 14 post-injection, and PK samples were collected prior and up to 72 hours after, to validate complete removal.

MRI was a useful visual support for the depth and size of the implant throughout the study. Ultrasound imaging at 4 hours post-dosing was challenging and the implants with volumes of 70 to 140 μL were difficult to locate. On days 1 to 6, the echogenicity of the depot was variable but viewable using lower frequencies (9 and 15 MHz). On days 14 to 35, ultrasound images using both 9- and 15 MHz probes were clear, aiding in locating the small-injected volumes. Higher frequency (30 and 50 MHz) probes did not assist in locating the implant. A risperidone implant was excised surgically on day 14 post-injection, after imaging and palpation at the location of the site of injection. No trace of the implant could be imaged, and plasma levels of risperidone dropped immediately post-excision. The excision site healed within a few days post-surgery, and the animals' recovery, monitored for up to 2 weeks post-excision, was good. Overall, locating the sc implant by clinically relevant imaging techniques such as ultrasound using 9 and 15 MHz probes, and MRI was proven to be feasible. Excision was successful and thorough, allowing removal of risperidone from systemic circulation, if needed.

The following examples 4-8 provide details of the human clinical studies assessing the Risperidone formulation. All subjects were administered the formulation using a sterile 1 mL syringe and a 21 G×⅝ inch (16 mm) sterile stainless steel safety needle. PFS were used in the Phase 1 BA and Phase 3 Safety studies. The Risperidone formulation in PFS is a ready-to-use, white to off-white, opaque, injectable suspension of 30% (w/w) risperidone in a solution of 2 copolymers (triblock copolymer and diblock copolymer) in dimethyl sulfoxide (DMSO). In some embodiments, the copolymer mixture is dissolved in the DMSO.

Example 4 Phase 1 Pilot Pharmacokinetic Study

A two-part clinical study was conducted to (part 1) evaluate the safety, tolerability and pharmacokinetics of the risperidone prolonged-release suspensions disclosed herein for subcutaneous injection (risperidone formulations) and (part 2) evaluate the influence of manipulation of the injection site and the site of administration on the pharmacokinetics (PK) of the risperidone, it metabolite 9-hydroxy-risperidone (9-OH-risperidone, paliperidone), as well as total active moiety (TAM).

This study was performed on 59 healthy volunteers, 53 received the Risperidone formulation and 6 received an injection of vehicle (the formulation vehicle without risperidone).

Part 1 of this study was an open-label, nonrandomized, ascending dose study (5 cohorts), and Part 2 of this study was an open-label, nonrandomized, ascending dose study (2 cohorts).

The study showed that the Risperidone formulation was safe and that the injection sites (upper arm/abdomen) are interchangeable.

Example 5 Phase 1 SAD/MAD Study

A sequential, single ascending dose and multiple ascending dose study was conducted to evaluate the safety, tolerability, and pharmacokinetics of the risperidone extended-release injectable suspension disclosed herein for subcutaneous use, in patients with schizophrenia or schizoaffective disorder.

The study population was 99 patients with schizophrenia, with 88 patients, aged 18-55, included in the safety component of the study. The study design was an open-label, single ascending dose (SAD) study (6 cohorts) and multiple ascending dose (MAD) study (2 cohorts), for a total of 8 cohorts.

The studies of Examples 4 and 5 together demonstrated several points:

- The safety profile of the formulations disclosed herein was consistent with the known risperidone formulations;
- Rubbing didn't affect any of the risperidone formulation attributes;
- No serious adverse reactions linked to the formulations disclosed herein;
- The treatment methods demonstrated a favorable risk/benefit profile;
- No significant change in pharmacokinetic parameters were observed during change of the injection site;
- Validation of doses and target durations: 1-month (once monthly; Q1M) and 2-month (once every two months; Q2M) products.

The results from the studies in Examples 4 and 5 have shown that the formulations disclosed herein have 1-month and 2-month release profiles at the various doses and provide a rapid establishment of clinically-relevant risperidone plasma concentrations which reach a therapeutic level during the first 24 hours and remain in the therapeutic range throughout the dosing interval, thereby avoiding the need for oral supplementation after treatment initiation, and then slowly decrease over one to two months, respectively. Doses were selected based on the comparability of plasma concentrations with those obtained with oral risperidone over a 24-hour dosing interval at steady state, with the aim to ensure adequate exposure throughout the dosing period. Comparable exposure was detected for arm and abdomen administration.

In addition, model-based analysis intended to support the dosing rationale (dose and regimens) in the Phase 3 efficacy study suggested that the median TAM exposure of the Risperidone formulation following 50 mg to 250 mg Q1M and Q2M administrations throughout the dosing interval was within the range of daily oral risperidone 2 mg to 5 mg daily doses.

Safety, including local tolerance at the site of injection, was studied in the two clinical trials of Examples 4 and 5. The results from the two trials, for a total of 147 individuals, showed a safety profile consistent with the known safety profile of risperidone, along with good local tolerability at the site of injection. Two serious adverse events have been reported from cohort 8 of the study of Example 5, both events were assessed by both the investigator and sponsor as not related to the risperidone formulation. There were no other serious adverse events in patients who received the risperidone formulation in this study. The safety analysis for the study described in Example 5 is shown in Table 5.

TABLE 5

| | Analysis of adverse effects observed during the clinical phase | | | | | | | |
|---|---|---|---|---|---|---|---|---|
| | Cohort 1 (50 mg) 1 dose, Abd (N = 12) | Cohort 2 (75 mg) 1 dose, Abd (N = 12) | Cohort 3 (100 mg) 1 dose, Abd (N = 12) | Cohort 4 (150 mg) 1 dose, Abd (N = 12) | Cohort 5 (225 mg) 1 dose, Abd (N = 12) | Cohort 6 (50 mg) 3 doses, Abd (N = 12) | Cohort 7 (75 mg) 3 doses, Abd (N = 12) | Cohort 8 (225 mg) 1 dose, UA (N = 15) |
| Frequency of appearance of treatment-related adverse reactions | 3 patients (25%) | 4 patients (33%) | 5 patients (42%) | 3 patients (25%) | 11 patients (92%) | 3 patients (25%) | 5 patients (42%) | 12 patients (80%) |

TABLE 5-continued

| | Analysis of adverse effects observed during the clinical phase | | | | | | | |
|---|---|---|---|---|---|---|---|---|
| | Cohort 1 (50 mg) 1 dose, Abd (N = 12) | Cohort 2 (75 mg) 1 dose, Abd (N = 12) | Cohort 3 (100 mg) 1 dose, Abd (N = 12) | Cohort 4 (150 mg) 1 dose, Abd (N = 12) | Cohort 5 (225 mg) 1 dose, Abd (N = 12) | Cohort 6 (50 mg) 3 doses, Abd (N = 12) | Cohort 7 (75 mg) 3 doses, Abd (N = 12) | Cohort 8 (225 mg) 1 dose, UA (N = 15) |
| Most commonly observed treatment-related adverse reactions | Weight increase, injection site pain, erythema, swelling, pruritus and induration, blood creatinine phosphokinase increase, headache and sedation. | | | | | | | |
| Characteristics of treatment-related adverse reactions | Mild to moderate<br>All injection site adverse events were transient and resolved. None were serious | | | | | | | |
| Results of laboratory tests, vital signs, ECG, psychiatric assessment scales | Consistent with known safety profile of risperidone and did not reveal any new safety signals for risperidone LAI | | | | | | | |

Abd = abdominal sc injection,
UA = upper arm (back of upper arm) sc injection

The interchangeability of the two injection sites, abdomen, back of upper arm, was proven in the two clinical trials described in Examples 4 and 5. In Example 4, the interchangeability of injection sites was investigated with subtherapeutic doses (25 mg in Cohorts F and D). There was no significant difference in TAM exposure between the injection sites, with ≤10% change in $C_{max}$ and $AUC_{0-t}$. In the study described in Example 5, (225 mg in Cohorts 5 (abd) and 8 (UA)) the most relevant exposure parameters for a single dose injection were $AUC_{0-t}$ and $AUC_{0-28}$, which resulted in comparable values. Table 6 provides a comparison of TAM PK parameters obtained from the two studies by subcutaneous injection site.

TABLE 6

| Study/Dose | PK parameter (unit) | Abdomen (CV %) | Upper-Arm (CV %) | Geometric Mean Ratio |
|---|---|---|---|---|
| Phase 1 Example 4 25 mg | AUC0-∞ (ng · h/mL) | 47100 (21.1) | 54100 (31.2) | 1.15 |
| | AUC0-t (ng · h/mL) | 42000 (24.8) | 46300 (30.6) | 1.10 |
| Phase 1 Example 5 225 mg | AUC0-∞ (ng · h/mL) | 47524.9 (25.4) | 55499 (32.8) | 1.17 |
| | AUC0-t (ng · h/mL) | 45195.1 (28.8) | 42082.5 (44.3) | 0.93 |

Example 6: Phase 1 Relative Bioavailability (BA) Study

Study: The purpose of this Phase 1 study was to assess the relative bioavailability of Risperidone Formulation for subcutaneous administration in PFS compared to vials, in patients with schizophrenia or schizoaffective disorder.

Study Design: Open-label, parallel-design, single dose study comparing 100 mg from vial and 1-mL plastic syringe, sterile 21 gauge, 16 mm needle to 100 mg from single-use 1 mL, luer locked, glass, clear PFS and sterile 21 gauge, 16 mm needle.

A dose of 100 mg was considered representative of the doses intended for clinical practice. A non-compartmental pharmacokinetic analysis demonstrated that a single dose of 100 mg provides comparable exposure to that of daily 4 mg oral risperidone over a 1 month period. Specifically, similar exposure was demonstrated after 100 mg Risperidone formulation Q1M administration and daily oral doses of risperidone 4 mg. Based on the above, and since 4 mg is the therapeutic dose for most schizophrenia patients (Stroup and Marder 2017), the 100 mg Q1M dose, corresponding to the 4-mg oral risperidone dose, was considered the most appropriate dose to efficiently conduct this pharmacokinetic study.

One hundred twenty (120) patients were randomized into the BA study (10148). Upon enrollment, patients were administered with oral risperidone 4 mg daily (qd) for 7 days, followed by a washout period of at least 7 days. Thereafter, patients were randomly assigned into 1 of the following groups:

Group 1: Single-dose of Risperidone formulation 100 mg sc administered from vials (n=60)

Group 2: Single-dose of Risperidone formulation 100 mg sc administered from PFS (n=60)

Results

The mean plasma concentration-time profiles of TAM following treatment with the Risperidone formulation in vial and PFS presentations were qualitatively comparable. Following sc administration, there was an immediate increase in TAM plasma concentrations with each treatment group reaching therapeutic levels (≥10 ng/mL; Eerdekens et al 2004) within 24 hours after dosing. Observed concentration values at 24 hours postdose [C24h] are (geometric mean) 12.1 ng/mL (vial) and 13.4 ng/mL (PFS). The primary PK parameter that was used for comparison between the 2 presentations was AUC0-84d (the area under the plasma concentration-time curve from time 0 to the end of the 84-day dosing interval).

In an ad hoc analysis, a covariate for oral exposure (AUC0-tau, ss), was included in the analysis of covariance (ANCOVA) for the primary endpoint for both datasets since an intrinsic heterogeneity, as demonstrated by an apparent predisposition of patients randomized into the PFS treatment group towards higher TAM exposures upon oral risperidone administration compared to those of patients randomized to the vial treatment group was identified. Upon oral risperidone exposure normalization in the primary and ad-hoc datasets, the bioavailability was similar between the Risperidone formulation vial vs. PFS presentations. The exposure (AUC0-84) of PFS as compared to vial with oral risperidone AUC0-tau,ss as a covariate was 24,295 ng*h/mL (PFS) and 22,411 ng*h/mL (vial).

Furthermore, the safety and tolerability of the PFS presentation was comparable to that of the vial presentation with respect to: pain intensity, local reactions (pruritis, nodules, rash, and swelling), incidence of AEs, changes from baseline in electrocardiogram parameters, selected clinical laboratory values (including prolactin), vital signs, Columbia-Suicide Severity Rating Scale (C SSRS), and Positive and Negative Syndrome Scale (PANSS)—indicating the safety and tolerability of PFS in patients with schizophrenia was comparable to that of vials.

The data, including the primary analysis outcomes, baseline adjustment results, and safety results, shows that both presentations provide comparable exposure and result in a similar clinical profile.

Example 7: Phase 3 Pivotal Efficacy Clinical Study with Risperidone Formulation (30072)

Study: The purpose of the study was to evaluate the efficacy, safety, and tolerability of different dose regimens of the Risperidone formulation described herein administered subcutaneously as compared to placebo during treatment in adult and adolescent patients with schizophrenia.

Study Design: Double-blind, randomized, relapse prevention study comparing once monthly (Q1M) and once bimonthly (once every 2 months, Q2M) Risperidone formulations (50 mg to 250 mg) of the disclosure at a therapeutic dose with placebo sc (once month, Q1M) in a 1:1:1 ratio.

Study Population: Male and female patients, 13 to 65 years of age, who had a confirmed diagnosis of schizophrenia, were clinically stable, and eligible for risperidone treatment. In total, 1267 patients were screened, 863 were enrolled and 544 patients aged between 16 and 65 years, inclusive, were randomized (eITT population); 363 patients of that group were randomized to receive the Q1M (183) or Q2M (180) dosing regimen (remainder received placebo) and all 363 patients were evaluable for pharmacokinetics.

Study Drug: 360 mg/mL risperidone in formulations as disclosed herein. The study drug was presented in glass vial which included an amount of risperidone formulation. The study drug was tested for risperidone exposure upon subcutaneous (sc) administration once monthly (Q4W), once a month or once every 28-31) days (Q1M) or once every two months (Q8W, every 56-62 days) (Q2M). Participants received sc injections into upper arm or abdomen, depending on study site.

Placebo arm: Participants received a sc injection of placebo (polymer vehicle) matched to Risperidone formulation at baseline and every 4 weeks (Q4W) thereafter. Participants continued treatment until they experienced a relapse event; met 1 or more of the study discontinuation or withdrawal criteria; or remained relapse-free during the double-blind phase until the study was terminated.

Q1 M arm: Participants received a sc injection of Risperidone formulation at baseline and Q4W thereafter. The maximal dose administered to adult participants was comparable to an oral risperidone dose of 5 mg/day, and the maximal dose administered to adolescents (aged 13-17) was comparable to an oral risperidone dose of 4 mg/day. Participants continued treatment until they experienced a relapse event; met 1 or more of the study discontinuation or withdrawal criteria; or remained relapse-free during the double-blind phase until the study was terminated.

Q2M arm: Participants received a sc injection of Risperidone formulation at baseline and every 8 weeks (Q8W) thereafter, and a placebo sc injection 4 weeks after baseline and Q8W thereafter. The maximal dose in both arms was equivalent to the same daily oral dose. Participants continued treatment until they experienced a relapse event; met 1 or more of the study discontinuation or withdrawal criteria; or remained relapse-free during the double-blind phase until the study was terminated.

Table 7 shows dosage selection of Risperidone formulation (extended release injectable suspension) compared to oral doses of risperidone. Table 8 shows doses composition.

TABLE 7

Dosage selection guide

| Dosing Regimen | Doses (mg) | | | |
|---|---|---|---|---|
| Once Monthly | 50 | 75 | 100 | 125 |
| Once Every 2 Months | 100 | 150 | 200 | 250 |
| | Comparable Oral Doses | | | |
| Daily Oral Risperidone | 2 | 3 | 4 | 5 |

TABLE 8

Composition of the Risperidone formulation

| Dosage | Risperidone (mg) | mPEG-PDL and PDL-PEG-PDL Copolymers (mg) | Dimethyl Sulfoxide (mg) | Total Volume (mL) |
|---|---|---|---|---|
| 50 mg | 50 | 42 | 75 | 0.14 |
| 75 mg | 75 | 63 | 113 | 0.21 |
| 100 mg | 100 | 83 | 150 | 0.28 |
| 125 mg | 125 | 104 | 188 | 0.35 |
| 150 mg | 150 | 125 | 225 | 0.42 |
| 200 mg | 200 | 167 | 300 | 0.56 |
| 250 mg | 250 | 208 | 375 | 0.70 |

Primary and Secondary Outcome Measures:

Primary Outcome Measure:

1. Time to Impending Relapse [Time Frame: 15 months] Is calculated as the earliest date the patient meets ≥1 of the impending relapse criteria
   Final analyses at 90 relapse events.

Secondary Outcome Measures:

1. Time to impending relapse [Time Frame: 15 months] As defined under the primary objective in the total population (adults and adolescents).
2. Time to impending relapse in adolescent patients with schizophrenia. 3. Impending Relapse Rate [Time Frame: Week 24] This rate will be estimated using the Kaplan-Meier method.
4. Observed Rate of Impending Relapse [Time Frame: 15 months] Calculated as the number of patients who relapsed by endpoint divided by the number of patients in each treatment group.
5. Percentage of Patients Who Maintain Stability [Time Frame: 15 months] Stability is defined as meeting all of the following criteria for at least 4 consecutive weeks: outpatient status; PANSS total score ≤80; minimal presence of specific psychotic symptoms on the PANSS, as measured by a score of ≤4 on each of the following items: conceptual disorganization, suspiciousness, hallucinatory behavior, and unusual thought content; Clinical Global Impression of Severity (CGI-S) score ≤4 (moderately ill); and Clinical Global Impression-Severity of Suicidality (CGI-SS) score ≤2 (mildly suicidal) on Part 1 and ≤5 (minimally worsened) on Part 2. The percentage will be calculated as the number of patients who maintained stability at endpoint divided by the number of patients in the given treatment group.

6. Percentage of Patients Achieving Remission [Time Frame: 15 months] Positive symptom, negative symptom, and overall symptom remission will be examined and are defined by Andreasen et al (Remission in Schizophrenia: Proposed Criteria and Rationale for Consensus, Am J Psychiatry, 162(3): 441. 2005), including severity and duration criteria. All remission criteria can be derived from PANSS items.
7. Percentage of Participants with Adverse Events [Time Frame: 15 months]

Relapse was defined as one or more of the following items:

- Clinical Global Impression-Improvement (CGI-I) of ≥5 AND
- an increase of any of the following PANSS items: conceptual disorganization, hallucinatory behavior, suspiciousness, and unusual thought content to a score of >4 with an absolute increase of ≥2 on that specific item since randomization OR
- an increase in any of the following 4 PANSS items: conceptual disorganization, hallucinatory behavior, suspiciousness, and unusual thought content to a score of >4 and an absolute increase of ≥4 on the combined score of the 4 PANSS items since randomization;
- hospitalization due to worsening of psychotic symptoms Clinical Global Impression-Severity of Suicidality (CGI-SS) of 4 or 5 on Part 1 and/or 6 or 7 on Part 2
- Violent behavior resulting in clinically significant self-injury, injury to another person, or property damage.

Results

Study 30072 was a double-blind, randomized study comparing therapeutic doses of Risperidone formulation administered subcutaneously (sc) Q1M and Q2M with placebo sc Q1M as treatment for schizophrenia following an oral conversion and stabilization stage (Stage 1). This study intended to provide extensive and relevant safety and efficacy information for the Risperidone formulation Q1M and Q2M dosing regimens. The PK data collected during the course of the study was further analyzed in population PK (PopPK) modeling (Example 9, infra). Final analyses were at 90 relapse events.

During the randomized portion of the study (Stage 2), patients received their assigned treatment until they experienced a relapse event or met 1 or more of the study withdrawal criteria. The mean (median) duration of exposure during Stage 2 was 30.9 weeks (24.3 weeks) for patients in the placebo group, 41.9 weeks (40.0 weeks) for patients in the Risperidone formulation Q1M group, and 42.1 weeks (38.1 weeks) for patients in the Risperidone formulation Q2M group. There were 26 (15%) patients who received placebo, 29 (16%) patients who received Risperidone formulation Q1M, and 25 (14%) patients who received Risperidone formulation Q2M for at least 6 months. There were 36 (20%) patients who received placebo, 64 (35%) patients who received Risperidone formulation Q1M, and 65 (36%) patients who received Risperidone formulation Q2M for at least 12 months.

Characteristics of the patient population were balanced across the treatment groups. 90 patients completed the study due to a relapse and 250 patients were relapse-free at study completion. Subgroup analyses by gender, age, and race did not suggest any clear evidence of differential responsiveness to the treatment. All data were processed and summarized by the use of SAS® Version 9.4. Time to events methodologies were used for the primary and some key secondary endpoints. For other continuous endpoints, the Least Squares (LS) means and SAS type III sum of squares for the statistical inference was used for mixed model repeated measures (MMRM). For categorical endpoints, the Cochran-Mantel-Haenszel (CMH) test was used. All statistical tests were 2 tailed at the 0.05 level of significance.

Summary of Results

Long acting injectable Risperidone formulation administered once monthly (Q1M) or once every 2 months (Q2M) demonstrated statistically significant treatment benefit compared with placebo.

- Treatment with the Risperidone formulation resulted in statistically significant prolongation in the time to impending relapse/delaying time to impending relapse compared to placebo for overall and for the Q1M and Q2M regimens. Compared to placebo, Risperidone formulation significantly prolonged the time to impending relapse by 3.5 times overall, by 5 times with Q1 M administration and by 2.7 times with Q2M administration.
- Risperidone formulation significantly decreased the risk to relapse by 80.0% for Q1M and 62.5% for Q2M administration compared to placebo for the entire study duration.
- Proportions of patients with impending relapse at week 24 were significantly lower for the Risperidone formulation-treated groups (overall: 9%; Q1M: 7%; Q2M: 11%) versus placebo (28%; P<0.0001, P<0.0001, P=0.0001, respectively).
- Proportions of patients maintaining stability were significantly higher (overall: 83%, Q1M: 87%, Q2M: 80% vs placebo 61%; P<0.0001, P<0.0001, P=0.0001, respectively).

Primary endpoint for number of participants with impending relapse (in the Intent-to-treat [ITT] analysis set) at 108 weeks is provided in Table 9. Data is presented as distribution of relapsing participants (number of participants with impending relapse). ITT analysis set: adult participants randomized to double-blind maintenance treatment, regardless if they received treatment or not.

TABLE 9

| End point values | Placebo | Q1M | Q2M |
|---|---|---|---|
| Number of subjects analyzed | 181 | 183 | 179 |
| Participants with impending relapse | 53 | 13 | 23 |

Clinical importance was further demonstrated by the key secondary endpoints in a pooled analysis of the Risperidone formulation Q1M and Q2M dosing regimens compared with placebo.

The number of participants with impending relapse (in the extended ITT [eITT] analysis set, including adolescent subjects) at 108 weeks is provided in Table 10. Data is presented as distribution of relapsing participants (adults and adolescents) (number of participants with impending relapse). eITT analysis set included participants randomized to double-blind maintenance treatment, regardless if they received treatment or not.

TABLE 10

| End point values | Placebo | Q1M | Q2M |
|---|---|---|---|
| Number of subjects analyzed | 181 | 183 | 180 |
| Participants with impending relapse | 53 | 13 | 24 |

Impending relapse rate at Week 24 was estimated using the Kaplan-Meier product estimate. ITT analysis set included adult participants randomized to the double-blind maintenance treatment, regardless if they had received treatment or not. The impending relapse rate at week 24 was statistically significantly lower in patients treated with Risperidone formulation (9% overall [7% for Q1 M and 11% for Q2M]) compared to placebo (28%), provided in FIG. 1 and Table 11, below:

TABLE 11

| End point values | Placebo | Q1M | Q2M |
|---|---|---|---|
| Number of subjects analyzed | 181 | 183 | 179 |
| Measure Type: Number | 0.28 | 0.07 | 0.11 |
| (Confidence Interval 95%) | (0.205 to 0.347) | (0.03 to 0.109) | (0.065 to 0.165) |

Furthermore, the percentage of patients who maintained stability at endpoint was statistically significantly higher in patients treated with Risperidone formulation (83% overall [87% for Q1 M and 80% for Q2M]) compared to placebo treatment (61%). Stability is defined as meeting all of the following criteria for at least 4 consecutive weeks: outpatient status; PANSS total score ≤80; minimal presence of specific psychotic symptoms on the PANSS, as measured by a score of ≤4 on each of the following items: conceptual disorganization, suspiciousness, hallucinatory behavior, and unusual thought content; Clinical Global Impression of Severity (CGI-S) score ≤4 (moderately ill); and CGI-SS score ≤2 (mildly suicidal) on Part 1 and ≤5 (minimally worsened) on Part 2. The last valid participant assessment was used as the endpoint. Table 12 shows number of patients stabilized with each treatment:

TABLE 12

| End point values | Placebo | Q1M | Q2M |
|---|---|---|---|
| Number of subjects analyzed | 181 | 183 | 179 |
| Participants stabilized | 110 | 159 | 143 |

The number of patients achieving remission at endpoint (up to 108 weeks) is shown in Table 13. Statistical significance was not reached and this result was not unexpected, given the relatively long mean duration of disease for patients in this study (>18 years) combined with the stringent criteria used to define remission in this study (ie, no relapse during the study and for at least 6 months prior to endpoint must have maintained scores of on each of the 8 specific PANSS items: P1 [delusions], G9 [unusual thought content], P3 [hallucinatory behavior], P2 [conceptual disorganization], G5 [mannerisms/posturing], N1 [blunted affect], N4 [social withdrawal], and N6 [lack of spontaneity]).

TABLE 13

| End point values | Placebo | Q1M | Q2M |
|---|---|---|---|
| Number of subjects analyzed | 181 | 183 | 179 |
| Participants reaching remission | 30 | 39 | 42 |

Psychopathological symptom severity changes were evaluated using the

Positive and Negative Syndrome Scale (PANSS),

Clinical Global Impression-Severity (CGI-S), and

Clinical Global Impression-Improvement (CGI-I) in subjects treated with risperidone formulation compared to placebo.

Changes in CGI-S did not reach statistical significance at end of treatment. However, PANSS scores decreased until the end of treatment (EoT) for Risperidone formulation treated subjects, but increased for placebo. (Least squares mean (LSM) change (standard error, SE): Q1M, −3.46 (0.69); Q2M, −4.88 (0.73); placebo, 1.11 (0.86); P<0.0001 vs placebo for both). When assessed by CGI-I, greater symptom improvement was observed from week 12/randomization (study baseline) to end of treatment with Risperidone formulation compared with placebo (LSM (SE): Q1M, 3.30 (0.08); Q2M, 3.15 (0.08); placebo, 3.85 (0.10); P<0.0001 vs placebo for both).

Patient centered outcomes assessed throughout the study were

Drug Attitude Inventory 10-item version (DAI-10), the DAI-10 scale demonstrates correlation with medication compliance and treatment outcome, Schizophrenia Quality of Life Scale (SQLS), EuroQol's 5-level European Quality of Life 5 level EQ-5D (EQ-5D-5L) visual analog scale (VAS) and descriptive items, Personal and Social Performance scale (PSP).

After substantial improvements during the oral stabilization phase:

SQLS and EQ-5D-5L VAS scores continued to improve significantly from randomization to end of treatment (EOT, 108 weeks) for all Risperidone formulation treated groups, while the scores remained similar in the placebo group. An improvement in quality of life (QoL) is represented as a decrease in score for SQLS and an increase in score for EQ-5D-5L.

The key secondary efficacy variable of changes from baseline in SQLS total score showed some differences from placebo in favor of study drug (Q1M and Q2M) at ET (LS mean [SE]: −3.99 [1.74] and −1.58 [1.78], respectively, compared to 3.20 [1.58] with placebo) and at EoT (LS mean [SE]: −5.40 [1.12] and −4.54 [1.16], respectively, compared to 1.14 [1.32] with placebo). The exploratory efficacy variable of change from baseline in EQ-5D-5L score showed differences from placebo in favor of study drug (pooled Q1M and Q2M) at ET (LS mean [SE]: −0.99 [1.41] compared to −4.74 [1.76] with placebo) and at EoT (LS mean [SE]: 2.28 [0.83] compared to −2.46 [1.32] with placebo).

Higher PSP total scores represent better personal and social functioning. Mean PSP scores did not continue to significantly improve from randomization in any treatment group. However, the exploratory efficacy variable of change from baseline in PSP total score showed differences favoring study drug (pooled Q1M and Q2M) over placebo in investigator-assessed personal and social functioning at ET (LS mean [SE]: −2.65 [0.82] with the pooled Q1M and Q2M group compared to −5.29 [0.97] with the placebo group) and at EoT (LS mean [SE]: 1.56 [0.52] with the pooled Q1M and Q2M group compared to 0.11 [0.84] with placebo group.

Data from the efficacy trial showed a high correlation with medication compliance and treatment outcome, as measured by the DAI-10 scale. Mean DAI-10 scores improved significantly (P<0.01) from randomization in the Risperidone formulation treated overall and Q1M treatment groups. A positive total score indicates a positive attitude toward psychiatric medications and thus corresponds to a compliant response, and vice versa. The key secondary efficacy variable of change from baseline in DAM 0 total score showed some differences from placebo in the patient's attitude toward their medication in favor of study drug (Q1M and Q2M) at ET (LS mean [SE]: 0.25 [0.42] and −0.40 [0.41], respectively, compared to −0.55 [0.38] with placebo) and at EoT (LS mean [SE]: 0.57 [0.28] and 0.10 [0.29], respectively, compared to −0.59 [0.31] with placebo).

After little improvement during the oral stabilization phase EQ-5D-5L descriptive item scores improved significantly (P<0.05) between randomization and EOT for mobility (overall and Q1M groups only), pain/discomfort, and anxiety/depression (all Risperidone formulation treated groups).

Patients who received Risperidone formulation showed ongoing improvement compared to placebo with regard to their attitude toward their medication (DAI-10 total score) and investigator-assessed psychopathology (PANSS total score) with ongoing treatment.

Figure 2:
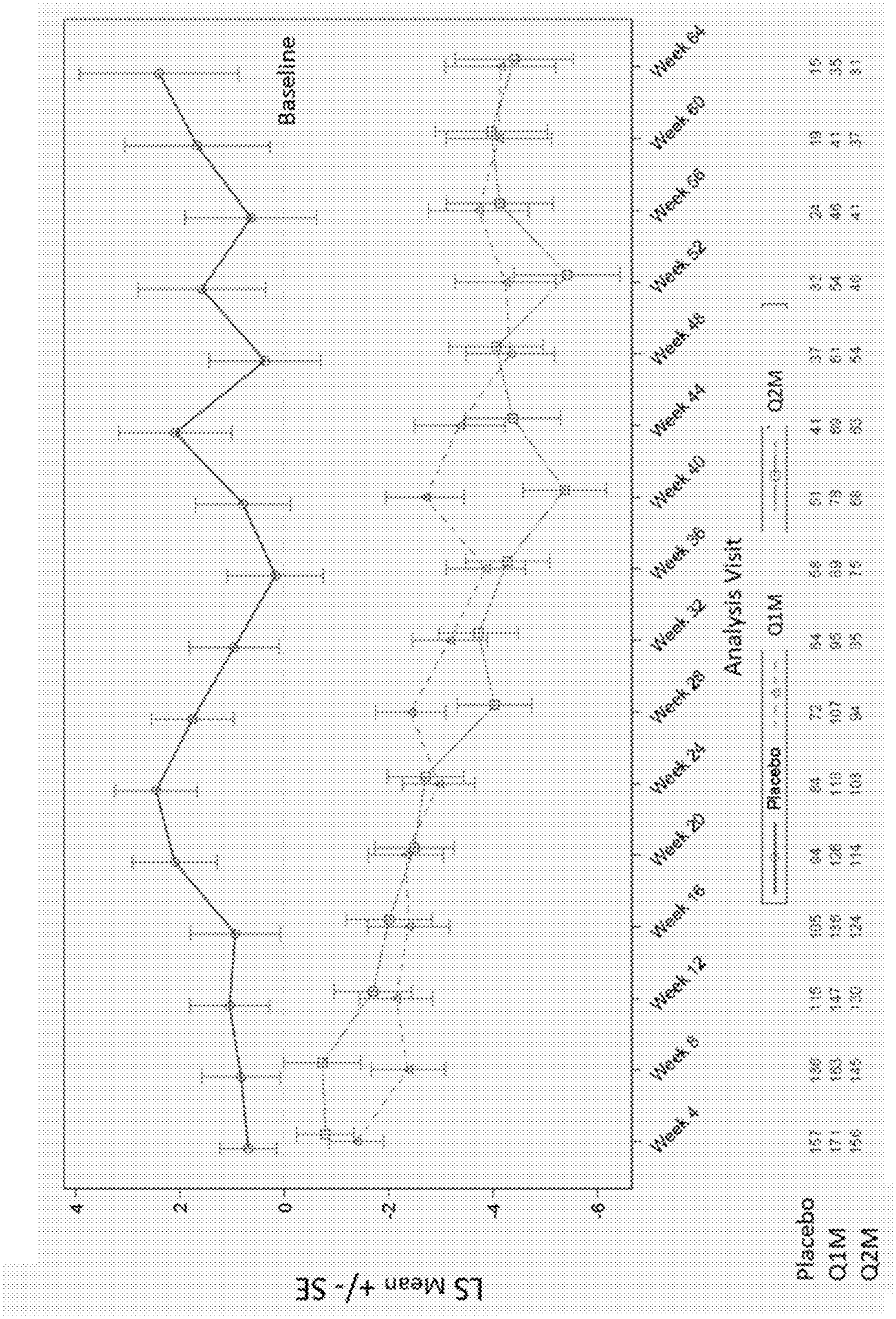
FIG. 2: Decrease in total PANSS score post stabilization. Q1M (short dashed line with triangles) and Q2M (long dashed line with squares) respectively, compared to placebo (solid line with circles)
Figure 3A:
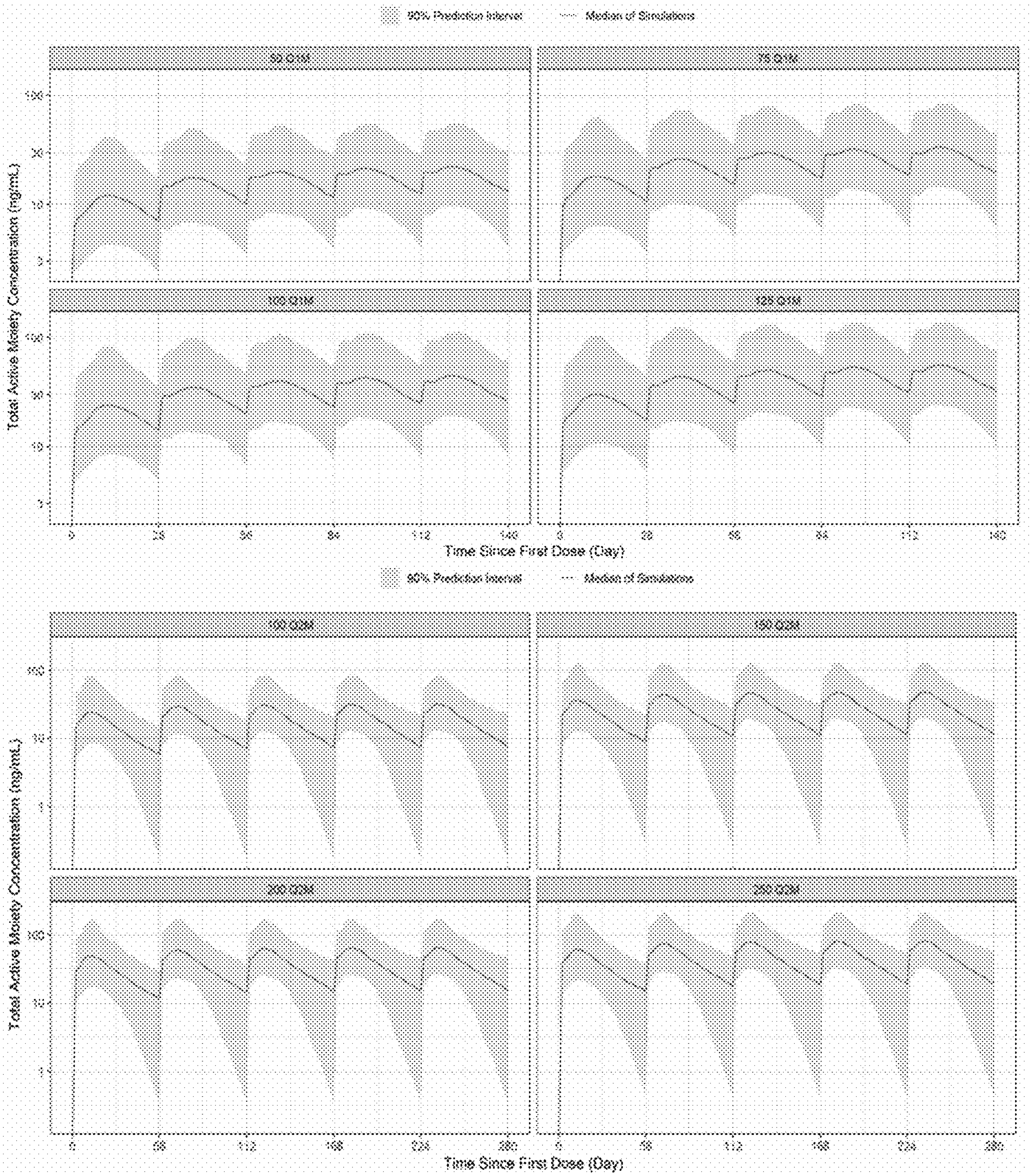
FIGS. 3A and 3B: Absorption profile of risperidone formulation administered subcutaneously (sc) disclosed herein, compared to absorption profile of PERSERIS® administered subcutaneously (sc). After a single subcutaneous injection of the risperidone formulation described herein, a single absorption peak of risperidone and its metabolite, 9-OH risperidone, was observed (3A. Q1M upper panel (50 mg, 75 mg, 100 mg, 125 mg) and Q2M lower panel (100 mg, 150 mg, 200 mg, 250 mg)). After single subcutaneous injection, PERSERIS® shows two absorption peaks for risperidone in plasma. The first peak of risperidone occurs with a Tmax of 4 to 6 hours and is due to an initial release of the drug during the depot formation process. A second peak of risperidone is observed at 10 to 14 days post-dose and is associated with the slow release of risperidone from the subcutaneous depot. The first and second peaks of risperidone are of similar magnitude. For both 9-hydroxy risperidone and total active moiety, the median Tmax of the first peak ranges from 4 to 48 hours and the second peak ranges from 7 to 11 days. (3B) (Ivaturi et al, Exposure-response analysis after subcutaneous administration of RBP-7000, a once-a-month long-acting Atrigel formulation of risperidone. Br J Clin Pharmacol. 2017 July; 83(7): 1476-1498; PERSERIS PI 07/2018. https://www.accessdata.fda.gov/drugsatfda_docs/label/2018/210655s000lbl.pdf)
Figure 3B:
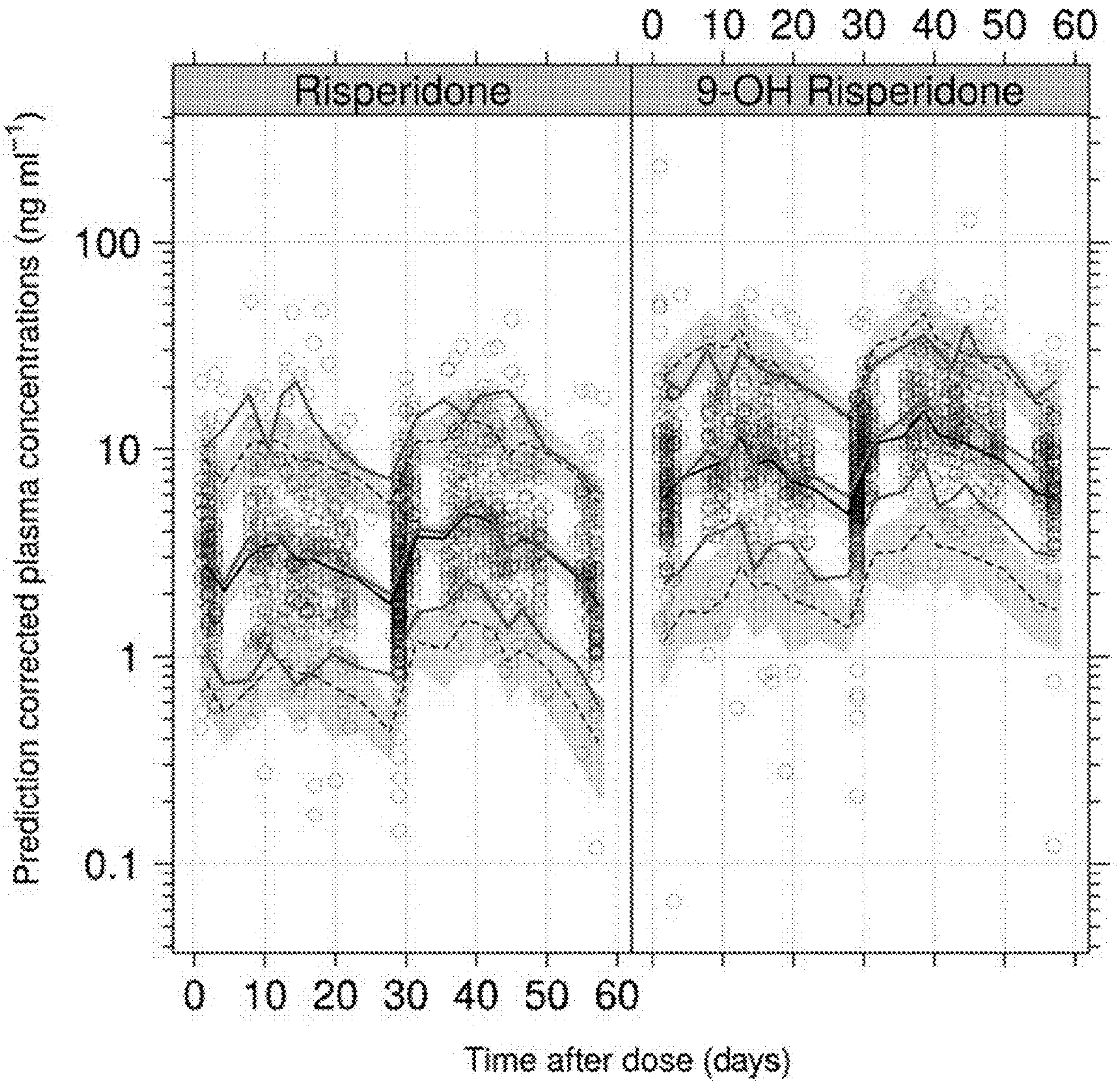

The PANSS total score was assessed over time. Unexpectedly, a post stabilization decrease in the PANSS score was observed over time, at least through week 64 (FIG. 2). This was surprising taking into consideration that the study participants were clinically stable at enrollment and had a long history of disease (average 10 years). The proportion of patients maintaining stability and/or showing post stabilization improvement was significant in the Risperidone formulation treatment groups.

CONCLUSIONS

The study met the primary efficacy endpoint for the long acting injectable Risperidone formulation Q1M compared to placebo (p<0.0001).

The study met the primary efficacy endpoint for Risperidone formulation Q2M compared to placebo (p<0.0001).

Risperidone formulation decreased the risk to relapse by 80.0% and 62.5% for Q1 M and Q2M respectively, compared to placebo for the entire study duration.

Risperidone formulation prolonged the time to relapse by 5 and 2.7 times compared to placebo in Q1M and Q2M respectively. The proportion of patients with impending relapse was lower in the treatment group (13 [7%] patients in the Q1M group and 23 [13%] patients in the Q2M group) compared to the placebo group (53 [29%] patients).

Patients on Risperidone formulation exhibited a beneficial and lasting post stabilization decrease in the PANSS score over time.

Sensitivity analysis showed that the statistical significance was maintained even using extreme conservative assumptions regarding early termination.

The safety profile was favorable, with no unexpected findings.

The safety, PK parameters and efficacy of both injection sites, upper arm and abdomen, are similar and can be used to administer Risperidone formulation, interchangeably.

The average exposure values (Cavg,ss) over the dosing period were comparable for Risperidone formulation administered once monthly and once every 2 months at corresponding doses. Following both once monthly (50 mg to 125 mg) and once every 2 months dosing (100 mg to 250 mg), the mean exposure of the TAM (AUC0-tau) corresponded to that of daily oral risperidone (2 mg to 5 mg/day) administered over an equivalent dosing period.

Efficacy and safety results of this study support the benefit of Risperidone formulation Q1M and Q2M products for treatment of patients with schizophrenia. Treatment with Risperidone formulation significantly reduced the impending time to relapse and significantly decreased the risk of relapse compared to placebo, and the reduction in the risk of relapse was sustained throughout the study. Compared to placebo, Risperidone formulation prolonged the time to relapse by 5 times with Q1M administration and by 2.7 times with Q2M administration.

The safety profile of the active ingredient, risperidone, given orally or as a long-acting parenteral formulation has been well characterized. The study data demonstrated that Risperidone formulation administered subcutaneously once monthly (Q1M) and once every two months (Q2M) indicated a safety profile consistent with other formulations of risperidone and the patient population, including common adverse events.

Availability of both a Q1M and a Q2M dosing regimen, with several dosing options (comparable to a 2-5 mg/day oral treatment) has the potential to improve patient outcome by delaying relapse and reducing the time to relapse, and maintaining a decrease in PANSS total score. These features may also improve compliance and acceptance, both of which are critical for maintaining patients on the required therapeutic doses, thereby improving disease outcomes. These dose selections provide a longer dosing interval and greater flexibility for the clinician to vary the doses (50 mg −250 mg comparable to 2-5 mg/day oral) and dose intervals between once monthly and once every 2 months regimens, based on clinical need and suitability.

A person with skill in the art is able to determine the appropriate dose and dosing regimen for a particular subject.

Example 8: Phase 3 Safety Clinical Trial with Risperidone Formulation

Study: The primary objective of the study was to evaluate the long-term safety and tolerability of Risperidone formulation. All subjects were treated with Risperidone formulation in prefilled syringe (PFS) which is a 1 ml glass syringe with a ⅝ inch long (16 mm), 21 gauge sterile safety needle. The primary safety and tolerability endpoint was frequency of all adverse events (AE), including serious adverse events (SAE). For new patients, the total duration of patient participation in the study was up to 80 weeks (including a screening period of up to 4 weeks, a 12-week oral conversion/stabilization stage [Stage 1], a 56-week double-blind stage [Stage 2], and a follow-up period [8 weeks]). For roll-over patients (from Efficacy Study 30072, Example 7), the total duration of patient participation in the study was planned to be up to 64 weeks (including up to 56 weeks in the Stage 2 and a follow-up period [8 weeks]). Patients who started Stage 2 or relapse or meet 1 or more of the withdrawal criteria were invited to the Early Termination visit as soon as possible within 4 weeks of the last injection. Patients who withdrew from the study before completing the 56-week stage 2 had follow-up procedures and assessments performed at their follow-up visits. During the follow-up period, patients were treated according to the investigator's judgment.

Study Design:

Allocation: Randomized

Intervention Model: Parallel Assignment

Masking: Quadruple (Participant, Care Provider, Investigator, Outcomes Assessor)

Primary Purpose: Treatment

Study Endpoints

Primary Outcome Measures: 1. Number of AE including SAE [Time Frame: Week 56]

Other Outcome Measures: 1. Number of participants who withdraw due to AE [Time Frame: Week 56]

Ages: 13 Years to 65 Years (Adolescent (13-17 years old); adult (18-65 years old)

Inclusion Criteria:

Patients Rolling Over from the Pivotal Efficacy Study 30072:

1. The patient must have participated in the Study 30072 without experiencing relapse events and without important protocol deviations.
2. If the patient was taking antidepressants or mood stabilizers in Study 30072, no dose changes or initiation of treatment with these medications will be permitted.
3. The patient, in the investigator's judgment, requires chronic treatment with an antipsychotic medication.

New Patients (Not Rolling Over from the Study 30072):

1. The patient has a diagnosis of schizophrenia
2. The patient has been responsive to an antipsychotic treatment (other than clozapine) in the past year based on investigator judgment (and discussions with family members, caregivers, or healthcare professionals as applicable).
3. The patient, in the investigator's judgment, requires chronic treatment with an antipsychotic medication.

Exclusion Criteria:

Patients Rolling Over from Study 30072:

1. The patient has a finding in the baseline 12-lead ECG that is considered clinically significant in the judgment of the investigator.
2. Poor compliance with study procedures (in the opinion of the investigator or sponsor) during the pivotal efficacy study. To be discussed on a case-by-case basis.

New Patients (Not Rolling Over from Study 30072) and Roll-Over Patients:

1. The patient is currently on clozapine or has received electroconvulsive therapy in the last 12 months.
2. The patient has a history of epilepsy or seizures, neuroleptic malignant syndrome, tardive dyskinesia, or other medical condition that would expose the patient to undue risk.
3. The patient has a positive serology for human immunodeficiency virus (HIV)-1, HIV-2, hepatitis B surface antigen, and/or hepatitis C.
4. The patient has current or a history of known hypersensitivity to risperidone or any of the excipients of Risperidone formulation or the oral formulation of risperidone used in the stabilization phase.
5. The patient has a substance use disorder, including alcohol and benzodiazepines but excluding nicotine and caffeine.
6. The patient is a pregnant or lactating female.

7. The patient has used an investigational drug other than Risperidone formulation within 3 months prior to screening or has participated in a non-drug clinical trial within 30 days prior to screening.
8. Vulnerable patients (eg, people kept in detention).

Example 9: Population Pharmacokinetics (PopPK) Modeling

The five clinical studies disclosed supra contributed to the characterization of the pharmacokinetics (PK) and exposure-response (ER) relationships of the Risperidone Formulation following subcutaneous administration.

A PopPK validated model was created using data from the Phase 1 studies and the Phase 3 efficacy and safety studies, disclosed above: PopPK of the parent molecule (risperidone), and its main active metabolite (9-hydroxy risperidone, 9-OH-risperidone), and total active moiety (TAM). The TAM of risperidone was calculated as the sum of risperidone and 9-OH-risperidone plasma concentrations, corrected by molecular weight, according to the following formula:

[Active Moiety](ng/mL)=[risperidone](ng/mL)+[9-OH-risperidone](ng/m L) 410/426).

Phase 1 studies included extensive PK sampling and Phase 3 studies included plasma samples for PK measures in both studies were collected at each in-clinic visit during the oral risperidone stabilization and treatment periods.

The general procedures that were followed for PopPK model development are outlined below:

1. Exploratory data analysis
2. Base structural model development
3. Evaluation of covariate effects
4. Model refinement
5. Model evaluation An initial PK model was developed based on the data from two Phase 1 studies (Examples, 4 and 5). The model was able to adequately capture the complex release and absorption of risperidone. It was used to support the in-study dose escalation decisions during Phase 1 SAD/MAD study in patients with schizophrenia or schizoaffective disorder (Example 5) and support the design of the subsequent studies (Examples 6, 7, and 8).

The second PK model was a sequential parent-metabolite model: first, a model was developed to describe the risperidone (parent) PK based on the data from the all clinical studies (Examples 4 to 8). This was a one compartment model, with a first order and transit compartment absorption routes and a first-order elimination.

Then, a sequential model was developed to describe 9-OH-risperidone (metabolite) PK. The PK of 9-OH-risperidone was described by a one compartment model, with first order input from the risperidone compartment, and first order elimination. Predicted risperidone concentration from the parent model was used as input into the metabolite central compartment. No covariates were identified that were deemed statistically significant and clinically relevant.

Finally, model estimated parent and metabolite levels were used to calculate TAM exposure, which was used for PK evaluation and simulations as well as for exposure-response evaluation of safety and efficacy.

PopPK simulations conducted using the final model suggest that during treatment with Risperidone formulation in the various dosing regimens, TAM exposure was generally sustained over time and comparable with established oral risperidone regimens.

The PopPK simulations demonstrated that the selected doses and dosing regimens provide adequate TAM exposures, comparable to those of the corresponding daily oral doses (2 mg, 3 mg, 4 mg, 5 mg) throughout the dosing interval (at least 28 days and up to two months).

The Risperidone formulation demonstrated dual absorption with a rapid initial absorption phase, and a slower secondary absorption phase. After a single-dose sc administration, median Tmax for TAM ranged from days 8-14 and 9-15 days for multiple dose administration. Therapeutic plasma risperidone concentrations were reached rapidly, within 6 to 24 hours following sc injection, depending on the dose. Therefore, neither loading dose nor supplemental oral risperidone is required. Similarly, the PopPK of risperidone (parent) was also best described by 2 absorption rate processes (1 fast and 1 slow) to account for the rapid initial appearance of risperidone in the systemic circulation and the sustained concentration in plasma governed by the slow release of risperidone from the depot.

Median accumulation ratios for AUC at steady-state were approximately 2.0 and 1.5 for the Q1M and Q2M regimens, respectively; the median accumulation ratios for $C_{max}$ at steady-state were approximately 1.9 and 1.4 for the Q1M and Q2M, respectively; the median accumulation ratios for $C_{trough}$ at steady-state were approximately 2.4 and 1.5 for the Q1M and Q2M, respectively.

For all doses, steady-state plasma levels of risperidone and 9-OH-risperidone were reached within 2 months of initiation for both the Q1M and Q2M dose regimens. Steady-state plasma exposure values of risperidone, 9-OH-risperidone, and TAM following once monthly administration were approximately 2- to 2.5-fold higher than single dose exposure, while the values for Risperidone formulation administered once every 2 months were about 1.5-fold higher than the respective single dose exposure. After administration, plasma levels of risperidone, 9-OH-risperidone, and TAM (AUC0-tau and Cmax) increased in a dose-proportional manner.

Risperidone formulation administered in the abdomen or upper arm resulted in similar pharmacokinetic profiles for all doses, permitting either injection site to be used interchangeably. In the Phase 3 studies, the Risperidone formulation was administered to majority of the patients in the abdomen by sc injection. Approximately 20% of the centers injected the formulation into the patients back of the upper arm. In Study 30072, 32% of patients received the Risperidone formulation in the upper arm, and in Study 30078, 11% of patients received Risperidone formulation in the upper arm. Comparability of the 2 injection sites was also evaluated in the final PopPK model which included pooled pharmacokinetic data from the Phase 1 and Phase 3 clinical studies. The dataset included injection data from 2251 and 1035 injections administered to the abdomen and arm, respectively. Simulations showed similar exposure following administration in different injection sites. Overall exposure (AUC,ss; and Cmax,ss) and the 90% prediction interval of each exposure metric of both injection sites were overlapping The PopPK model based covariate analysis suggested that in the adolescent population (ages 13-17), age and weight do not have an impact on exposure of Risperidone formulation which is expected to be comparable to adults.

The final PopPK model estimates for clearance (CL) of risperidone and 9-OH-risperidone were 14.3 L/h and 5.78 L/h, respectively. The final PopPK model determined that poor CYP2D6 metabolizer status is associated with relatively lower risperidone clearance and the clearance for metabolite (CLMO) for 9-OH-risperidone is typically higher in poor CYP2D6 metabolizers. These findings are in line with the mechanism of CYP2D6 mediated 9-hydroxylation of risperidone. In poor CYP2D6 metabolizers, risperidone clearance is lower than in subjects with normal CYP2D6 metabolism, and the fraction of risperidone metabolized to 9-OH-risperidone is lower, resulting in higher apparent CLMO. Since the overall pharmacologic activity of risperidone is governed by TAM, the effect of the above demographic factors on the CL of risperidone and CLMO for 9-OH-risperidone was not considered to be clinically meaningful and therefore CYP2D6 metabolizer status requires no dose adjustment.

Exposure-Response (E-R) Analysis

Data from the Phase 3 studies in patients with schizophrenia (Examples 7 and 8) were pooled for development of E-R models describing the relationships between Risperidone formulation exposure (TAM) and measures of efficacy and safety. The endpoints that were evaluated in the E-R analysis are as follows:

Efficacy endpoint: Time to relapse (which is defined by CGI-I, PANSS, and CGI-SS scores, hospitalization due to worsening of psychotic symptoms, or violent behavior.) The criteria for impending relapse are disclosed above, Example 7.

Occurrence of certain adverse events (AEs)

The exposure parameters that were used in the exposure-efficacy analysis were taken from the final PopPK dataset and included: Cavg,ss, Cmax,ss and Ctrough,ss.

The exposure parameters (Cavg,ss, Cmax,ss and Ctrough, ss) combined for all doses and dosing regimens of TV 46000 were divided into 4 equally sized quantiles to allow better visualization in the Kaplan Meier plots, with the calculation of bins based on the distribution of the parameter.

The quartiles were defined as below:

Q1=min 25th percentile, N=107

Q2=25th percentile 50th percentile, N=106

Q3=50th percentile 75th percentile, N=106

Q4=75th percentile max), N=106

Time-to-event analysis of impending relapse was explored by Kaplan-Meier evaluation. Kaplan-Meier curves of impending relapse were stratified by groups based on dosing frequency, cohort and TAM exposure. Kaplan-Meier evaluations were also conducted for systemic AEs and stratified by TAM exposure. Logistic regression was conducted for AEs.

Results:

The exposure metrics were divided in four equally sized quartiles based on the distribution of the metric. Table 14 provides predicted TAM PK values for Cavg, Cmax and Ctrough at steady state (ss).

TABLE 14

| | Predicted TAM PK parameters Quartiles Median [min, max] | | | |
|---|---|---|---|---|
| | N | Cavg, ss (ng/mL) | Cmax, ss (ng/mL) | Ctrough, ss (ng/mL) |
| Q1M (N = 215) | | | | |
| Quartile 1 | 54 | 15.8 [4.19-21.5] | 18.3 [5.27-25.4] | 11 [2.99-14.6] |
| Quartile 2 | 54 | 26.2 (21.6-33.1] | 31.7 (25.5-38.1] | 19.2 (14.7-23.6] |
| Quartile 3 | 53 | 39.7 (33.4-47.8] | 47.6 (38.2-55.7] | 29 (24.2-34.5] |
| Quartile 4 | 54 | 66.5 (48.3-168] | 75.9 (55.7-224] | 46.8 (34.6-140] |
| Q2M (N = 210) | | | | |
| Quartile 1 | 53 | 15.2 [3.55-19.2] | 21 [4.99-30] | 3.15 [0.318-6.25] |
| Quartile 2 | 52 | 23.9 (19.6-28.9] | 37.1 (30.4-43.7] | 9.05 (6.41-12] |
| Quartile 3 | 52 | 35.6 (29-42.9] | 55.7 (44.3-72.7] | 14.9 (12.1-19.8] |
| Quartile 4 | 53 | 60.5 (43.1-126] | 102 (72.8-308] | 30.9 (19.8-72.2] |

Cavg, ss = average plasma drug concentration at steady-state;
Cmax, ss = maximum plasma drug concentration at steady state;
Ctrough, ss = trough plasma drug concentrations at steady-state The exposure-response analysis for impending relapse indicated no trend, suggesting similar treatment benefit for Q1M and Q2M regimens, across all doses and exposure groups in the phase 3 studies. Low TAM Ctrough,ss concentrations were not associated with an increased risk of impending relapse.

Safety analysis: An exposure-response correlation was found between the TAM levels and occurrence of Extrapyramidal Symptom (EPS) adverse events (AE) and further investigated using logistic regression and Kaplan-Meier plots. The incidence of EPS was higher in a subgroup of patients with high TAM Cmax,ss concentrations. However, the severity grade of all EPS events that occurred during the Phase 3 studies following risperidone formulation administration for all doses and dose regimens was mild or moderate in severity, with no severe EPS events observed. Upon stratifying EPS AEs based on moderate severity only, no significant difference was observed between placebo and treatment (p=0.26 for Cmax,ss), implying no clear E-R relationship between the TAM Cmax,ss range and moderate EPS AEs.

Example 10: Risperidone Formulation Storage and Stability Testing

The Risperidone formulations in vials and PFS were tested for stability over time. The Risperidone formulations were tested as follows:

a) Long term at 5° C. for 0, 3, 6, 9, 12, 18, 24 and 36 months;
b) Accelerated at 25° C./60% RH for 0, 3, and 6 months;
c) Photostability—the drug product was exposed to artificial daylight fluorescent lamp with an overall illumination of 1.2 million lux hours and to an integrated near ultraviolet energy of not less than 200 watt hours/square meter, at 25° C./60% RH. Eleven (11) primary batches were tested. The study was performed for the drug product in primary (PFS) and in secondary packaging (PFS in closed carton) to evaluate protection from light for both;
d) Freeze-thaw cycling test—the drug product was stored for 2 days at −20° C. and then for 2 days at 25° C./60% RH. Eleven (11) primary batches were tested. Three (3) such cycles were repeated before testing. The test was performed to evaluate the drug product sensitivity on thermal cycling that can occur during storage and distribution;
e) Freezing—the drug product was stored for 2 weeks at −20° C. followed by 2 weeks at 5° C. Eleven (11) primary batches were tested. The test was performed to evaluate the drug product sensitivity to freezing conditions that can occur during distribution.
f) Thermal excursion—study effect of prolonged (1 month) storage at 25° C./60% RH on the stability of the drug product throughout shelf life was tested. Study was performed at the beginning and was repeated at the end of shelf life (24 months and 36 months) on eleven (11) batches to simulate temperature excursions that may occur during storage and distribution of the drug product. The impact of prolonged storage at 25° C./60% RH for up to 3 months was checked at the end of shelf life (36 months) to evaluate longer temperature excursions that may occur during storage and distribution of the drug product. During the study the drug product was stored horizontally.
g) Cumulative temperature effects to study cumulative exposure of the drug product to 25° C./60% RH during the shelf life in intervals of 7, 14, 21 and 28 days. For 28 days of cumulative exposure, the drug product was exposed to 25° C./60% RH at 4 intervals of 7 days throughout the shelf life of 0, 6, 12 and 24 months. The study was performed on eleven (11) batches to simulate the product being repeatedly removed from the refrigeration and returned if not used throughout its shelf life.

Batches of PFS with 50 mg, 75 mg, 100 mg, 125 mg, 150 mg, 200 mg and 250 mg risperidone formulation were tested.

Long term and accelerated storage studies were performed with PFS in horizontal, vertical and inverted positions to assess the features: appearance at storage condition and room temperature, particulate matter, assay, related compounds, copolymer molecular weight, in vitro drug release and particle size distribution; viscosity and water content; and or Bacterial Endotoxins and sterility.

Long term and accelerated storage studies were performed with PFS in the tray in horizontal, vertical and inverted positions to assess Initiating Force; Sustaining Force; Container Closure Integrity, Delivered dose and Delivered volume.

Results: After up to 24 months of storage at 5° C. and up to 6 months of storage at 25° C./60% RH no significant change in any of the features described above was observed in all batches for all parameters tested.

Change in the parameter appearance occurred during the Photostability Study for all batches of the drug product in the primary packaging (PFS). No such change occurred for the drug product when placed in the secondary packaging. Secondary packaging provides adequate protection of the drug product from light. Examples of secondary packaging include a carton, a box, an envelope, a pouch, an aluminum foil covering, and the like.

No significant change in quality of the drug product occurred during Freezing and Cycling Tests; the product tolerates freezing and short term temperature cycling.

No significant change in quality occurred during Thermal Excursion Study at the beginning of the shelf life; product can be used within three months after thawing (from refrigerator) when stored at room temperature.

The PFS may be stored at 2-8° C. for at least 12 months, 24 months, or 30 months or 36 months. The Risperidone formulations may be stored at room temperature 68 to 77° F. (20-25° C.) unopened for up to 90 days (for example up to 30 days, up to 60 days or 90 days) and may be returned to refrigerated storage within 90 days as long as unopened. In some embodiments, the kit is stored in refrigerator at 36 to 46° F. (2 to 8° C.) in the original carton to protect from light. Prior to use, the kit may sit in its packaging at room temperature for at least 30 minutes prior to administration. The kit may be stored unopened in its original packaging at room temperature for up to 90 days. If unopened, the kit may be returned to refrigerated storage within 90 days. The risperidone formulation may be refrigerated and "defrosted" i.e., at room temperature, multiple times before use and continue to retain stability for use in a human subject. Once the carton is opened, the risperidone formulation may be administered subcutaneously.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied without departing from the spirit and scope of the invention. All patents, patent applications, and publications disclosed herein are herein incorporated by reference to the same extent as if each individual publication was specifically and individually indicated to be incorporated by reference. It should be understood that although the formulations, methods and kits have been specifically disclosed by preferred embodiments and optional features, modification and variation of the concepts herein disclosed may be resorted to by those skilled in the art, and that such modifications and variations are considered to be within the scope of this invention as defined by the appended claims.

The invention is described in further detail with reference to the following clauses:

1. A method of treating a psychiatric disease or disorder in a subject, comprising subcutaneously administering to the subject 1 mL or less of a long acting injectable risperidone formulation comprising
   (a) risperidone, or a pharmaceutically acceptable salt thereof, at a concentration of about 250-400 mg/mL, equivalent to risperidone;
   (b) a biodegradable triblock copolymer having the formula:
   poly(lactic acid)v-poly(ethylene glycol)w-poly(lactic acid)x,
   wherein v and x are the number of repeat units ranging from 24 to 682 and w is the number of repeat units ranging from 4 to 273 and v=x or v #x;
   (c) a biodegradable diblock copolymer having the formula:
   methoxy poly(ethylene glycol)y-poly(lactic acid)z,
   wherein y and z are the number of repeat units, wherein y is the number of repeat units ranging from 3 to 50 and z is the number of units ranging from 7 to 327; and
   wherein the ratio of the biodegradable triblock copolymer of (b) and the biodegradable diblock copolymer of (c) is 1:3 to 1:8 or 1:1 to 1:19 or 3:2 to 1:19, in said formulation, which is insoluble in an aqueous environment;
   wherein said formulation is subcutaneously administered at a frequency of no greater than once monthly, and wherein said formulation provides a therapeutically effective amount of risperidone for at least one month.
2. The method of clause 1, wherein said formulation is subcutaneously administered at a frequency of no greater than once every two months, and wherein said formulation provides a therapeutically effective amount of risperidone for at least two months.
3. The method of clause 1 or clause 2, wherein the subject is not administered a loading dose of oral risperidone.
4. The method of clause 1 or clause 3, wherein said formulation comprises from about 50 mg to about 125 mg risperidone.
5. The method of clause 2 or clause 3, wherein said formulation comprises from about 100 mg to about 250 mg risperidone.
6. The method of any one of clauses 1-5, wherein the psychiatric disease or disorder is schizophrenia.
7. The method of clause 6, wherein said method results in a reduction in the risk to relapse compared to placebo in subjects having schizophrenia.
8. The method of clause 7, wherein said risk to relapse is reduced by at least 50%.
9. The method of clause 7, wherein said risk to relapse is reduced by 60-80%.
10. The method of clause 6, wherein said method results in a lower rate of relapse compared to placebo in subjects having schizophrenia.
11. The method of clause 6, wherein said method extends the time to relapse compared to placebo in subjects having schizophrenia.
12. The method of clause 11, wherein the time to relapse is extended by at least 2-fold compared to placebo in subjects having schizophrenia.
13. The method of clause 11, wherein the time to relapse is extended 2.5 to 5-fold compared to placebo in subjects having schizophrenia.
14. A method of switching a subject from a daily oral risperidone therapy to a long acting injectable risperidone therapy, said method comprising:
   i. orally administering a final administration of the daily oral risperidone therapy, after which no further oral risperidone therapy is administered; and
   ii. the next day subcutaneously administering to the subject a long acting injectable risperidone formulation comprising
   (a) risperidone, or a pharmaceutically acceptable salt thereof, at a concentration of about 250-400 mg/mL, equivalent to risperidone;
   (b) a biodegradable triblock copolymer having the formula:
   poly(lactic acid)v-poly(ethylene glycol)w-poly(lactic acid)x, wherein v and x are the number of repeat units ranging from 24 to 682 and w is the number of repeat units ranging from 4 to 273 and v=x or v≠x;

(c) a biodegradable diblock copolymer having the formula:

methoxy poly(ethylene glycol)$_y$-poly(lactic acid)$_z$, wherein y and z are the number of repeat units, wherein y is the number of repeat units ranging from 3 to 50 and z is the number of units ranging from 7 to 327; and wherein the ratio of the biodegradable triblock copolymer of (b) and the biodegradable diblock copolymer of (c) is 1:3 to 1:8 or 1:1 to 1:19 or 3:2 to 1:19, in said formulation, which is insoluble in an aqueous environment;

thereby switching the subject from a daily oral risperidone therapy to a long acting injectable risperidone therapy.

15. The method of clause 14, wherein the long acting injectable risperidone therapy comprises a once monthly administration of the long acting injectable risperidone formulation.

16. The method of clause 14, wherein the long acting injectable risperidone therapy comprises a once bimonthly (i.e., once every two months) administration of the long acting injectable risperidone formulation.

17. The method of clause 15 wherein said long acting injectable risperidone formulation comprises from about 50 mg to about 125 mg risperidone.

18. The method of clause 16 wherein said long acting injectable risperidone formulation comprises from about 100 mg to about 250 mg risperidone.

19. A method of switching a subject from a once monthly long acting injectable risperidone therapy to a once bimonthly (i.e., once every two months) long acting injectable risperidone therapy without the need for supplemental oral risperidone therapy, said method comprising:

i. subcutaneously administering a final dose of the once monthly long acting injectable risperidone therapy; and ii. one month later subcutaneously administering the once bimonthly (i.e., once every two months) long acting injectable risperidone therapy;

wherein the once monthly and once bimonthly (i.e., once every two months) long acting injectable risperidone therapies are formulations that comprise (a) risperidone, or a pharmaceutically acceptable salt thereof, at a concentration of about 250-400 mg/mL, equivalent to risperidone;

(b) a biodegradable triblock copolymer having the formula: poly(lactic acid)v-poly(ethylene glycol)w-poly(lactic acid)x, wherein v and x are the number of repeat units ranging from 24 to 682 and w is the number of repeat units ranging from 4 to 273 and v=x or v≠x;

(c) a biodegradable diblock copolymer having the formula: methoxy poly(ethylene glycol)y-poly(lactic acid)z, wherein y and z are the number of repeat units, wherein y is the number of repeat units ranging from 3 to 50 and z is the number of units ranging from 7 to 327; and wherein the ratio of the biodegradable triblock copolymer of (b) and the biodegradable diblock copolymer of (c) is 1:3 to 1:8 or 1:1 to 1:19 or 3:2 to 1:19, in said formulation, which is insoluble in an aqueous environment;

and wherein said method is performed without administering to the subject a supplemental oral risperidone therapy.

20. A method of switching a subject from a once bimonthly (i.e., once every two months) long acting injectable risperidone therapy to a once monthly long acting injectable risperidone therapy without the need for supplemental oral risperidone therapy, said method comprising:

i. subcutaneously administering a final dose of the once bimonthly (i.e., once every two months) long acting injectable risperidone therapy; and ii. two months later subcutaneously administering the once monthly long acting injectable risperidone therapy;

wherein the once monthly and once bimonthly (i.e., once every two months) long acting injectable risperidone therapies are formulations that comprise (a) risperidone, or a pharmaceutically acceptable salt thereof, at a concentration of about 250-400 mg/mL, equivalent to risperidone;

(b) a biodegradable triblock copolymer having the formula: poly(lactic acid)v-poly(ethylene glycol)w-poly(lactic acid)x, wherein v and x are the number of repeat units ranging from 24 to 682 and w is the number of repeat units ranging from 4 to 273 and v=x or v≠x;

(c) a biodegradable diblock copolymer having the formula: methoxy poly(ethylene glycol)y-poly(lactic acid)z, wherein y and z are the number of repeat units, wherein y is the number of repeat units ranging from 3 to 50 and z is the number of units ranging from 7 to 327; and wherein the ratio of the biodegradable triblock copolymer of (b) and the biodegradable diblock copolymer of (c) is 1:3 to 1:8 or 1:1 to 1:19 or 3:2 to 1:19, in said formulation, which is insoluble in an aqueous environment;

and wherein said method is performed without administering to the subject a supplemental oral risperidone therapy.

21. A method of changing the risperidone dose administered to a subject undergoing once monthly or once bimonthly (i.e., once every two months) long acting injectable risperidone therapy from an initial dose of a long acting injectable risperidone formulation to a subsequent dose of a long acting injectable risperidone formulation, without the need for supplemental oral risperidone therapy, said method comprising:

i. subcutaneously administering a final administration of the initial dose of the long acting injectable risperidone formulation; and ii. after a period of time subcutaneously administering the subsequent dose of the long acting injectable risperidone formulation;

wherein the initial dose and the subsequent dose of the long acting injectable risperidone formulations are different doses of a long acting injectable risperidone formulation that comprises (a) risperidone, or a pharmaceutically acceptable salt thereof, at a concentration of about 250-400 mg/mL, equivalent to risperidone;

(b) a biodegradable triblock copolymer having the formula:

poly(lactic acid)v-poly(ethylene glycol)w-poly(lactic acid)x, wherein v and x are the number of repeat units ranging from 24 to 682 and w is the number of repeat units ranging from 4 to 273 and v=x or v≠x;

(c) a biodegradable diblock copolymer having the formula:

methoxy poly(ethylene glycol)y-poly(lactic acid)z, wherein y and z are the number of repeat units, wherein y is the number of repeat units ranging from 3 to 50 and z is the number of units ranging from 7 to 327; and wherein the ratio of the biodegradable triblock copolymer of (b) and the biodegradable diblock copolymer of (c) is 1:3 to 1:8 or 1:1 to 1:19 or 3:2 to 1:19, in said formulation, which is insoluble in an aqueous environment;

and wherein said method is performed without administering to the patient any supplemental oral risperidone therapy.

22. The method of clause 21, wherein the initial dose of the long acting injectable risperidone formulation comprises a higher dose of risperidone than the subsequent dose of long acting injectable risperidone formulation.

23. The method of clause 21, wherein the initial dose of the long acting injectable risperidone formulation comprises a lower dose of risperidone than the subsequent dose of long acting injectable risperidone formulation.

24. The method of any one of clauses 21 to 23, wherein the subsequent dose of the long acting injectable risperidone formulation is administered one month after administration of the initial dose of the long acting injectable risperidone formulation.

25. The method of any one of clauses 21 to 23, wherein the subsequent dose of the long acting injectable risperidone formulation is administered two months after administration of the initial dose of the long acting injectable risperidone formulation.

26. The method of any one of the preceding clauses, wherein the subcutaneous administration is into the upper arm of the subject or the abdomen of the subject.

27. The method of clause 26, wherein the subcutaneous administration is into the upper arm of the subject.

28. The method or clause 26, wherein the subcutaneous administration is into the abdomen of the subject.

29. The method of any one of the preceding clauses, wherein the long acting injectable risperidone formulation is administered from a prefilled syringe fitted with a needle having a gauge number equal to or greater than 21 and/or a length equal to or shorter than ⅝ inch.

30. A method of administering risperidone to a subject undergoing long acting injectable risperidone therapy wherein said subject has missed a dose of the long acting injectable risperidone therapy, said method comprising subcutaneously administering a dose of a once monthly or once bimonthly (i.e., once every two months) long acting injectable risperidone therapy;

wherein the long acting injectable risperidone therapy comprises (a) risperidone, or a pharmaceutically acceptable salt thereof, at a concentration of about 250-400 mg/mL, equivalent to risperidone;

(b) a biodegradable triblock copolymer having the formula: poly(lactic acid)v-poly(ethylene glycol)w-poly(lactic acid)x, wherein v and x are the number of repeat units ranging from 24 to 682 and w is the number of repeat units ranging from 4 to 273 and v=x or v≠x;

(c) a biodegradable diblock copolymer having the formula: methoxy poly(ethylene glycol)y-poly(lactic acid)z, wherein y and z are the number of repeat units, wherein y is the number of repeat units ranging from 3 to 50 and z is the number of units ranging from 7 to 327; and wherein the ratio of the biodegradable triblock copolymer of (b) and the biodegradable diblock copolymer of (c) is 1:3 to 1:8 or 1:1 to 1:19 or 3:2 to 1:19, in said formulation, which is insoluble in an aqueous environment;

and wherein said method is performed without administering to the subject any supplemental oral risperidone therapy.

31. The method of any one of clauses 1-30, wherein the subcutaneous administration of the long acting injectable risperidone formulation results in a post stabilization decrease in the PANSS total score.

32. The method of any one of clauses 1-31, wherein the subcutaneous administration of the long acting injectable risperidone formulation results in a single absorption peak.

33. A prefilled syringe (PFS) for subcutaneously administering a long acting injectable risperidone formulation, said prefilled syringe comprising i. a long acting injectable risperidone formulation wherein said formulation comprises (a) risperidone, or a pharmaceutically acceptable salt thereof, at a concentration of about 250-400 mg/mL, equivalent to risperidone;

(b) a biodegradable triblock copolymer having the formula: poly(lactic acid)v-poly(ethylene glycol)w-poly(lactic acid)x, wherein v and x are the number of repeat units ranging from 24 to 682 and w is the number of repeat units ranging from 4 to 273 and v=x or v≠x;

(c) a biodegradable diblock copolymer having the formula: methoxy poly(ethylene glycol)y-poly(lactic acid)z, wherein y and z are the number of repeat units, wherein y is the number of repeat units ranging from 3 to 50 and z is the number of units ranging from 7 to 327; and wherein the ratio of the biodegradable triblock copolymer of (b) and the biodegradable diblock copolymer of (c) is 1:3 to 1:8 or 1:1 to 1:19 or 3:2 to 1:19, in said formulation, which is insoluble in an aqueous environment;

ii. a needle having a gauge number equal to or greater than 21 and/or a length equal to or shorter than ⅝ inch.

34. The prefilled syringe of clause 33, wherein the long acting injectable risperidone formulation is stable at room temperature for at least 30 days.

35. The prefilled syringe of clauses 33 or clause 34, wherein the long acting injectable risperidone formulation is stable at 2° to 8° C. for at least 36 months.

36. A kit comprising i. a prefilled syringe comprising a long acting injectable risperidone formulation wherein said formulation comprises a) risperidone, or a pharmaceutically acceptable salt thereof, at a concentration of about 250-400 mg/mL, equivalent to risperidone;

b) a biodegradable triblock copolymer having the formula:

poly(lactic acid)v-poly(ethylene glycol)w,-poly(lactic acid)x wherein v and x are the number of repeat units ranging from 24 to 682 and w is the number of repeat units ranging from 4 to 273 and v=x or v≠x;

c) a biodegradable diblock copolymer having the formula:

methoxy poly(ethylene glycol)y-poly(lactic acid)z, wherein y and z are the number of repeat units, wherein y is the number of repeat units ranging from 3 to 50 and z is the number of units ranging from 7 to 327; and wherein the ratio of the biodegradable triblock copolymer of (b) and the biodegradable diblock copolymer of (c) is 1:3 to 1:8 or 1:1 to 1:19 or 3:2 to 1:19, in said formulation, which is insoluble in an aqueous environment, ii. a needle having a gauge number equal to or greater than 21 and/or a length equal to or shorter than ⅝ inch, and iii. instructions for use.

37. The method of any one of clauses 1-32, the prefilled syringe of any one of clauses 33-35 or the kit of clause 36, wherein the long acting injectable risperidone formulation comprises 10% (w/w) triblock copolymer and 15% (w/w) diblock copolymer of the total weight percentage of the formulation.

38. The method, the prefilled syringe or the kit of clause 37 wherein the long acting injectable risperidone formulation comprises 45% DMSO of the total weight percentage of the formulation.

39. The method, the prefilled syringe or the kit of clause 37 or clause 38 wherein the long acting injectable risperidone formulation comprises 360 mg/mL risperidone base of the total weight percentage of the formulation.

The invention claimed is:

1. A method of switching a subject from a daily oral risperidone therapy to a long acting injectable risperidone formulation, said method comprising:

i. orally administering a final dose, i.e. a last dose, of the daily oral risperidone therapy, after which no further oral risperidone therapy is administered; and ii. the next day following the final dose of the daily oral risperidone therapy subcutaneously administering to the subject a first injectable dose of a long acting injectable risperidone formulation comprising:

(a) risperidone, or a pharmaceutically acceptable salt thereof, at a concentration of about 250-400 mg/mL, equivalent to risperidone;

(b) a biodegradable triblock copolymer having a formula:

poly(lactic acid)$_v$-poly(ethylene glycol)$_w$-poly(lactic acid)$_x$, wherein v and x are numbers of repeat units ranging from 24 to 682 and w is a number of repeat units ranging from 4 to 273 and v=x or v≠x; and, (c) a biodegradable diblock copolymer having the formula:

methoxy-poly(ethylene glycol)$_y$-poly(lactic acid)$_z$, wherein y and z are numbers of repeat units, wherein y is a number of repeat units ranging from 3 to 50 and z is a number of units ranging from 7 to 327; and wherein a ratio of the biodegradable triblock copolymer of (b) and the biodegradable diblock copolymer of (c) is 1:3 to 1:8 or 1:1 to 1:19 or 3:2 to 1:19, in said formulation, which is insoluble in an aqueous environment;

wherein the subcutaneous administration of the long acting injectable risperidone formulation results in a mean exposure of TAM (AUC0-tau) that is equivalent to that of oral risperidone (2 mg/day to 5 mg/day) administered over an equivalent dosing period; and wherein the long acting injectable risperidone formulation is administered once every two months and the method is implemented in the absence of a loading dose or supplemental oral risperidone or other antipsychotic drug;

thereby switching the subject from a daily oral risperidone therapy to a long acting injectable risperidone formulation.

2. The method of claim 1, wherein said long acting injectable risperidone formulation comprises from about 100 mg to about 250 mg risperidone in a volume of from about 0.2 mL to about 1.0 mL.

3. The method of claim 1, wherein the subcutaneous administration is into the upper arm of the subject or the abdomen of the subject.

4. The method of claim 3, wherein the subcutaneous administration into the upper arm is into the back of the upper arm of the subject.

5. The method or claim 3, wherein the subcutaneous administration is into the abdomen of the subject.

6. The method of claim 1, wherein the long acting injectable risperidone formulation is administered from a syringe fitted with a needle having a gauge number equal to or greater than 21 and/or a length equal to or shorter than ⅝ inch, optionally wherein the syringe is a pre-filled syringe.

7. The method of claim 1, wherein the subject is suffering from a psychiatric disease selected from schizophrenia, bipolar disorder and irritability associated with autism (IAA).

8. The method of claim 7, wherein the subject is suffering from schizophrenia.

9. The method of claim 8, wherein the subcutaneous administration of the long acting injectable risperidone formulation results in a post-stabilization decrease in a PANSS total score.

10. The method of claim 1, wherein the subject is an adult from an age of 18 to 65 years old or an adolescent from an age of 13 to 17 years old.

11. The method of claim 1, wherein the long acting injectable risperidone formulation comprises 10% (w/w %) triblock copolymer and 15% (w/w %) diblock copolymer of the total weight percentage of the formulation.

12. The method of claim 11, wherein the long acting injectable risperidone formulation further comprises DMSO.

13. The method of claim 11, wherein the long acting injectable risperidone formulation comprises 360 mg/mL risperidone base.

14. The method of claim 1, wherein:

a subcutaneous administration of the long acting injectable risperidone formulation to an upper arm is followed by, at the next dosing, a subcutaneous administration of the long acting injectable risperidone formulation to an abdomen; or a subcutaneous administration of the long acting injectable risperidone formulation to the abdomen is followed by, at the next dosing, a subcutaneous administration of the long acting injectable risperidone formulation to the upper arm.

* * * * *